United States Patent
Wang et al.

(10) Patent No.: US 9,255,107 B2
(45) Date of Patent: Feb. 9, 2016

(54) HETEROARYL ALKYNE COMPOUND AND USE THEREOF

(71) Applicant: NANJING SANHOME PHARMACEUTICAL CO., LTD., Nanjing, Jiangsu (CN)

(72) Inventors: Yong Wang, Jiangsu (CN); Liwen Zhao, Jiangsu (CN); Di Zhang, Jiangsu (CN); Feng Wu, Jiangsu (CN); Sheng Bi, Jiangsu (CN); Yiping Gao, Jiangsu (CN); Hongbin Chen, Jiangsu (CN); Hongyan Chen, Jiangsu (CN); Cang Zhang, Jiangsu (CN); Yang Nan, Jiangsu (CN); Yang Liu, Jiangsu (CN)

(73) Assignee: NANJING SANHOME PHARMACEUTICAL CO., LTD., Jiangsu (CN)

( * ) Notice: Subject to any disclaimer, the term of this patent is extended or adjusted under 35 U.S.C. 154(b) by 0 days.

(21) Appl. No.: 14/441,190

(22) PCT Filed: Nov. 27, 2013

(86) PCT No.: PCT/CN2013/087944
§ 371 (c)(1),
(2) Date: May 7, 2015

(87) PCT Pub. No.: WO2014/082578
PCT Pub. Date: Jun. 5, 2014

(65) Prior Publication Data
US 2015/0299202 A1 Oct. 22, 2015

(30) Foreign Application Priority Data
Nov. 28, 2012 (CN) .......................... 2012 1 0493364

(51) Int. Cl.
| | |
|---|---|
| *C07D 401/14* | (2006.01) |
| *C07D 403/14* | (2006.01) |
| *C07D 471/04* | (2006.01) |
| *C07D 487/04* | (2006.01) |
| *C07D 233/92* | (2006.01) |
| *A61K 31/4196* | (2006.01) |
| *A61K 31/496* | (2006.01) |
| *C07D 401/04* | (2006.01) |
| *C07D 403/04* | (2006.01) |
| *A61K 31/4178* | (2006.01) |
| *A61K 31/4439* | (2006.01) |
| *A61K 31/4985* | (2006.01) |
| *C07D 233/64* | (2006.01) |

(52) U.S. Cl.
CPC .......... *C07D 487/04* (2013.01); *A61K 31/4178* (2013.01); *A61K 31/4196* (2013.01); *A61K 31/4439* (2013.01); *A61K 31/496* (2013.01); *A61K 31/4985* (2013.01); *C07D 233/64* (2013.01); *C07D 233/92* (2013.01); *C07D 401/04* (2013.01); *C07D 401/14* (2013.01); *C07D 403/04* (2013.01); *C07D 403/14* (2013.01); *C07D 471/04* (2013.01)

(58) Field of Classification Search
CPC .. C07D 401/14; C07D 403/14; C07D 471/04; C07D 487/04; C07D 233/92; A61K 31/4196; A61K 31/496
See application file for complete search history.

(56) References Cited

U.S. PATENT DOCUMENTS

| | | | |
|---|---|---|---|
| 8,114,874 B2 | 2/2012 | Zou et al. | |
| 8,278,307 B2 | 10/2012 | Shakespeare et al. | |
| 8,470,851 B2 | 6/2013 | Zou et al. | |
| 8,846,671 B2 * | 9/2014 | Ding et al. | 514/233.2 |
| 2007/0191376 A1 | 8/2007 | Zou et al. | |
| 2009/0149471 A1 | 6/2009 | Shakespeare et al. | |
| 2009/0176781 A1 | 7/2009 | Wang et al. | |
| 2010/0261730 A1 | 10/2010 | Hartung et al. | |
| 2012/0135986 A1 | 5/2012 | Zou et al. | |
| 2013/0018046 A1 | 1/2013 | Wang et al. | |
| 2013/0196979 A1 | 8/2013 | Zou et al. | |
| 2013/0196985 A1 | 8/2013 | Ding et al. | |

FOREIGN PATENT DOCUMENTS

| | | |
|---|---|---|
| CN | 101389338 A | 3/2009 |
| CN | 101489558 A | 7/2009 |

(Continued)

OTHER PUBLICATIONS

Ding et al., caplus an 2013:1151986.*
Desai et al., caplus an 2013:304709.*
Ren et al., caplus an 2013:66763.*
Tumor, 2015, http://www.cancer.org/cancer/wilmstumor/detailedguide/wilms-tumor-prevention.*
Mar. 6, 2014 International Search Report issued in International Patent Application No. PCT/CN2013/087944.

(Continued)

*Primary Examiner* — Sun Jae Yoo
(74) *Attorney, Agent, or Firm* — Oliff PLC

(57) ABSTRACT

In the field of pharmaceutical chemistry compounds of general formula I having heteroaryl alkynyl moiety or pharmaceutically acceptable salts, isomers, solvates, crystals or prodrugs thereof, and pharmaceutical compositions including these compounds, as well as uses of these compounds and compositions thereof in the manufacture of a medicament. The compounds have a strong inhibitory effect on BCR-ABL tyrosine kinase and are useful for treating diseases, such as tumors.

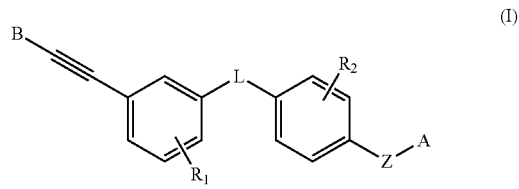

(I)

18 Claims, No Drawings

(56) References Cited

FOREIGN PATENT DOCUMENTS

| | | |
|---|---|---|
| CN | 101490053 A | 7/2009 |
| CN | 101885722 A | 11/2010 |
| CN | 103214480 A | 7/2013 |
| WO | 2009/074260 A1 | 6/2009 |

* cited by examiner

HETEROARYL ALKYNE COMPOUND AND USE THEREOF

TECHNICAL FIELD

The present invention belongs to the field of pharmaceutical chemistry. Specifically, the invention relates to compounds having heteroaryl alkynyl moiety and salts, stereoisomers, N-oxides, solvates, or prodrugs thereof, and pharmaceutical compositions comprising these compounds, as well as uses of these compounds and compositions thereof in the manufacture of a medicament.

BACKGROUND

Protein tyrosine kinases (PTKs) are a class of proteases capable of catalyzing the phosphorylation of the phenolic hydroxyl groups of tyrosine residues in various proteins and thus activating functions of functional proteins. Protein tyrosine kinases (PTKs) play very important roles in the intracellular signal transduction pathways, and regulate a series of biochemical processes, such as cell growth, differentiation and death. Abnormal expression of protein tyrosine kinases can cause disorder of cell proliferation regulation, and further result in tumorigenesis. In addition, abnormal expression of protein tyrosine kinases is also closely associated with invasion and metastasis of tumors, angiogenesis in tumors and chemotherapy resistance of tumors.

Tyrosine kinase inhibitors can be used as a competitive inhibitor of adenosine triphosphate (ATP) binding to tyrosine kinase, and can competitively bind to tyrosine kinases, block the activity of tyrosine kinase and inhibit cell proliferation. Several protein tyrosine kinase inhibitors have been successfully developed.

Imatinib mesylate, as a protein tyrosine kinase inhibitor, is the first molecular targeted agent. It competitively inhibits the binding sites of adenosine triphosphate (ATP) to thymidine kinase (TK) receptors such as KIT, and prevents phosphorylation of TK, thereby inhibiting the signal transduction. Imatinib can inhibit the KIT mutation associated with kinase activity and the wild type KIT, and has therapeutic effect on various types of cancers. Imatinib can inhibit Bcr-Abl tyrosine kinases at the cellular level in vivo and in vitro, and selectively inhibit proliferation and induce apoptosis in cells of Bcr-Abl positive cell lines as well as leukemic cells from patients with Philadelphia chromosome-positive (Ph+) chronic myeloid leukemia (CML) and acute lymphoblastic leukemia. In addition, Imatinib can also inhibit receptor tyrosine kinases for platelet-derived growth factor (PDGF) and stem cell factor (SCF), c-Kit, thereby inhibiting PDGF and stem cell factor-mediated cellular events. Clinically, Imatinib is mainly used in treatment of patients with chronic myeloid leukemia (CML) in accelerated phase, blast crisis or chronic phase after failure of α-interferon therapy, and patients with unresectable or metastatic malignant gastrointestinal stromal tumor (GIST). Also, Imatinib is used for treating CD 117-positive gastrointestinal stromal tumors (GIST).

Development and clinical use of Imatinib opens a new era of molecular targeted tumor therapy. Long-term use of Imatinib, however, may cause drug resistance, and lead to tumor recurrence. With wide clinical use of Imatinib, problem of drug resistance has become increasingly prominent. The acquired drug resistance was mainly due to Bcr-Abl point mutations, which render Imatinib unable to bind to Bcr-Abl. Also, it has been found that hundreds of Bcr-Abl point mutations are associated with imatinib resistance, of which 15 to 20% of imatinib-resistant patients have T315I mutation. Emergence of imatinib resistance arouses the research upsurge of a new generation of tyrosine kinase inhibitors.

AP24534 developed by Ariad Pharmaceuticals, Inc. (as shown in Formula A) well addresses this problem. Research shows that AP24534 is effective for CML patients having T315I mutation and resistant to second-generation TKIs, and is a multi-targeted kinase inhibitor against Bcr-Abl and SRC. AP24534 may act on the wild type cells and T315I-mutated cells, and inhibit Bcr-Abl and all mutants thereof including the T315I variants resistant to various therapeutic drugs, and is a broad spectrum inhibitor of Bcr-Abl.

Formula A Structure of AP24534

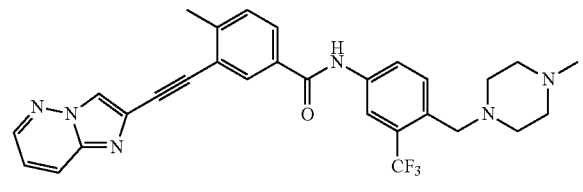

AP24534

SUMMARY

An objective of the present invention is to develop a class of novel protein kinase inhibitors having a heteroaryl alkynyl structure, which are capable of inhibiting multiple targets, such as Bcr-Abl and SRC, and having good activity against drug resistant enzymes resulted from T315I mutations.

To achieve the above objective, the present invention provides a compound of general formula I or a pharmaceutically acceptable salt, isomer, N-oxide, solvate, crystal, or prodrug thereof,

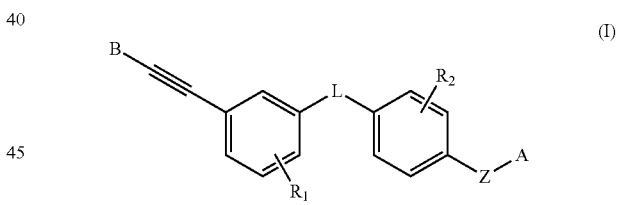

(I)

Another objective of the present invention is to provide a method for preparing the compound of general formula I or a pharmaceutically acceptable salt, isomer, N-oxide, solvate, crystal, or prodrug thereof.

A further objective of the present invention is to provide a composition comprising the compound of general formula I or a pharmaceutically acceptable salt, isomer, N-oxide, solvate, crystal, or prodrug thereof, and a pharmaceutically acceptable carrier.

A still further objective of the present invention is to provide a method of treating and/or preventing tumor using the compound of general formula I or a pharmaceutically acceptable salt, isomer, N-oxide, solvate or prodrug thereof, and a use of the compound of general formula I or a pharmaceutically acceptable salt, isomer, N-oxide, solvate or prodrug thereof in the manufacture of a medicament for treating and/or preventing tumors.

To achieve the above objectives, the following technical solutions are provided according to the present invention.

In a first aspect, the present invention provides a compound of general formula I or a pharmaceutically acceptable salt, isomer, N-oxide, solvate, crystal, or prodrug thereof,

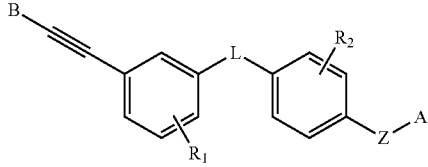
(I)

wherein

L is selected from —C(O)NH—, —NHC(O)NH—, and —NHC(O)—;

Z is selected from (CH$_2$)$_n$ or O, wherein n is selected from 0, 1, 2, 3, and 4;

A is selected from 5-, 6-, 7- and 8-membered nitrogen-containing heterocyclic groups;

R$_1$ is selected from H, alkyl, alkoxy, halo-substituted alkyl, halo-substituted alkoxy, —OH, —NH$_2$, halogen and —CN;

R$_2$ is selected from H, alkyl, alkoxy, halo-substituted alkyl, halo-substituted alkoxy, —OH, —NH$_2$, halogen and —CN;

B is selected from the following structures:

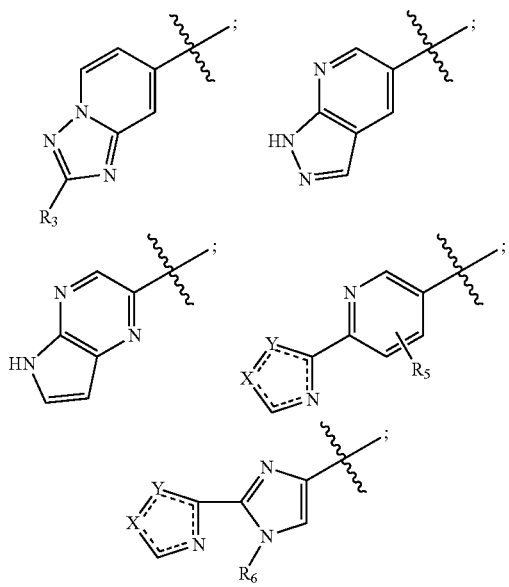

wherein R$_3$ is selected from H, amino, mono-alkylamino and di-alkylamino;

X is selected from C(R$_4$) and NH, and Y is selected from N and NH, wherein when X is C(R$_4$), Y is NH and

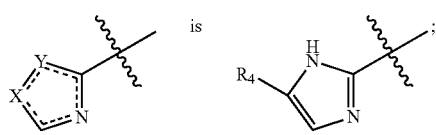

when X is NH, Y is N and

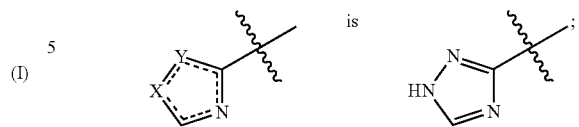

wherein R$_4$ is selected from H, NO$_2$, halogen, alkyl, halo-substituted alkyl and —CN;

R$_5$ is selected from H, alkyl, alkoxy, halo-substituted alkyl, halo-substituted alkoxy, —OH, —NH$_2$, halogen and —CN; and R$_6$ is selected from H and alkyl.

In some preferred embodiments, the compound of the present invention is a compound of general formula I or a pharmaceutically acceptable salt, isomer, N-oxide, solvate, crystal, or prodrug thereof, wherein L is selected from —C(O)NH—, —NHC(O)NH—, and —NHC(O)—;

Z is selected from (CH$_2$)$_n$, wherein n is selected from 0, 1, 2, and 3;

A is selected from 5- and 6-membered nitrogen-containing heterocyclic groups, and preferably selected from piperazinyl, tetrahydropyrrolyl, or substituted piperazinyl and tetrahydropyrrolyl, wherein the substituent(s) is(are) selected from alkyl, hydroxy, hydroxyalkyl, alkoxy, amino, mono-alkylamino, di-alkylamino, aminoacyl, alkylaminoacyl, arylaminoacyl, heteroarylaminoacyl, halogen, halo-substituted alkyl, and halo-substituted alkoxy;

R$_1$ is selected from H, C$_{1-6}$ alkyl, C$_{1-6}$ alkoxy, halo-substituted C$_{1-6}$ alkyl, halo-substituted C$_{1-6}$ alkoxy, —OH, —NH$_2$, halogen, and —CN; preferably selected from H, C$_{1-3}$ alkyl, C$_{1-3}$ alkoxy, halo-substituted C$_{1-3}$ alkyl, halo-substituted C$_{1-3}$ alkoxy, —OH, —NH$_2$, halogen, and —CN; and more preferably selected from H, methyl, ethyl, propyl, isopropyl, trifluoromethyl, fluoro, and chloro;

R$_2$ is selected from H, C$_{1-6}$ alkyl, C$_{1-6}$ alkoxy, halo-substituted C$_{1-6}$ alkyl, halo-substituted C$_{1-6}$ alkoxy, —OH, —NH$_2$, halogen, and —CN; preferably selected from H, C$_{1-3}$ alkyl, C$_{1-3}$ alkoxy, halo-substituted C$_{1-3}$ alkyl, halo-substituted C$_{1-3}$ alkoxy, —OH, —NH$_2$, halogen, and —CN; and more preferably selected from H, methyl, ethyl, propyl, isopropyl, trifluoromethyl, fluoro, and chloro;

B is selected from

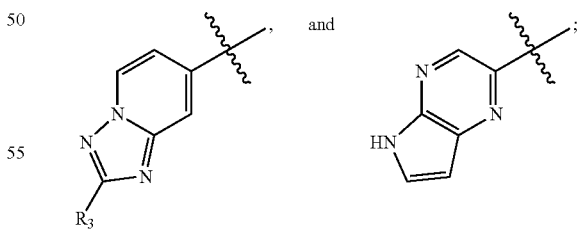

wherein R$_3$ is selected from H, amino, mono-alkylamino, and di-alkylamino; selected from H, amino, mono-C$_{1-6}$ alkylamino, and bi-C$_{1-6}$ alkylamino; more preferably selected from H, amino, mono-C$_{1-3}$ alkylamino, and bi-C$_{1-3}$ alkylamino; and even more preferably selected from H, amino, methylamino, and dimethylamino In some preferred embodiments, the compound of the present invention is a compound of general formula I or a pharmaceutically acceptable salt, isomer, N-oxide, solvate, crystal, or prodrug thereof, wherein L is —NHC(O)NH—;

Z is selected from $(CH_2)_n$, wherein n is selected from 0, 1, 2 and 3;

A is selected from 5- and 6-membered nitrogen-containing heterocyclic groups, and preferably selected from piperazinyl, tetrahydropyrrolyl, or substituted piperazinyl and tetrahydropyrrolyl, wherein the substituent(s) is(are) selected from alkyl, hydroxy, hydroxyalkyl, alkoxy, amino, mono-alkylamino, di-alkylamino, aminoacyl, alkylaminoacyl, arylaminoacyl, heteroarylaminoacyl, halogen, halo-substituted alkyl, and halo-substituted alkoxy;

$R_1$ is selected from H, $C_{1-6}$ alkyl, $C_{1-6}$ alkoxy, halo-substituted $C_{1-6}$ alkyl, halo-substituted $C_{1-6}$ alkoxy, —OH, —NH$_2$, halogen, and —CN; preferably selected from H, $C_{1-3}$ alkyl, $C_{1-3}$ alkoxy, halo-substituted $C_{1-3}$ alkyl, halo-substituted $C_{1-3}$ alkoxy, —OH, —NH$_2$, halogen, and —CN; and more preferably selected from H, methyl, ethyl, propyl, isopropyl, trifluoromethyl, fluoro, and chloro;

$R_2$ is selected from H, $C_{1-6}$ alkyl, $C_{1-6}$ alkoxy, halo-substituted $C_{1-6}$ alkyl, halo-substituted $C_{1-6}$ alkoxy, —OH, —NH$_2$, halogen, and —CN; preferably selected from H, $C_{1-3}$ alkyl, $C_{1-3}$ alkoxy, halo-substituted $C_{1-3}$ alkyl, halo-substituted $C_{1-3}$ alkoxy, —OH, —NH$_2$, halogen, and —CN; and more preferably selected from H, methyl, ethyl, propyl, isopropyl, trifluoromethyl, fluoro, and chloro; and B is

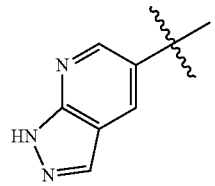

In some preferred embodiments, the compound of the present invention is a compound of general formula I or a pharmaceutically acceptable salt, isomer, N-oxide, solvate, crystal, or prodrug thereof, wherein L is selected from —C(O)NH—, —NHC(O)NH—, and —NHC(O)—;

Z is selected from $(CH_2)_n$ or O, wherein n is selected from 0, 1, 2 and 3;

A is selected from 5- and 6-membered nitrogen-containing heterocyclic groups, and preferably selected from piperazinyl, tetrahydropyrrolyl, pyrrolyl, imidazolyl, pyridinyl, or substituted piperazinyl, tetrahydropyrrolyl, pyrrolyl, imidazolyl and pyridinyl, wherein the substituent(s) is(are) selected from alkyl, hydroxy, hydroxyalkyl, alkoxy, amino, mono-alkylamino, di-alkylamino, aminoacyl, alkylaminoacyl, arylaminoacyl, heteroarylaminoacyl, halogen, halo-substituted alkyl, and halo-substituted alkoxy;

$R_1$ is selected from H, $C_{1-6}$ alkyl, $C_{1-6}$ alkoxy, halo-substituted $C_{1-6}$ alkyl, halo-substituted $C_{1-6}$ alkoxy, —OH, —NH$_2$, halogen, and —CN; preferably selected from H, $C_{1-3}$ alkyl, $C_{1-3}$ alkoxy, halo-substituted $C_{1-3}$ alkyl, halo-substituted $C_{1-3}$ alkoxy, —OH, —NH$_2$, halogen, and —CN; and more preferably selected from H, methyl, ethyl, propyl, isopropyl, trifluoromethyl, fluoro, and chloro;

$R_2$ is selected from H, $C_{1-6}$ alkyl, $C_{1-6}$ alkoxy, halo-substituted $C_{1-6}$ alkyl, halo-substituted $C_{1-6}$ alkoxy, —OH, —NH$_2$, halogen, and —CN; preferably selected from H, $C_{1-3}$ alkyl, $C_{1-3}$ alkoxy, halo-substituted $C_{1-3}$ alkyl, halo-substituted $C_{1-3}$ alkoxy, —OH, —NH$_2$, halogen, and —CN; and more preferably selected from H, methyl, ethyl, propyl, isopropyl, trifluoromethyl, fluoro, and chloro; and B is

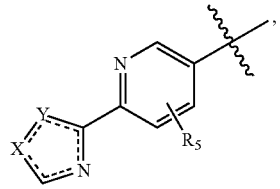

wherein X is selected from $C(R_4)$ and NH, and Y is selected from N and NH, wherein when X is $C(R_4)$, Y is NH and

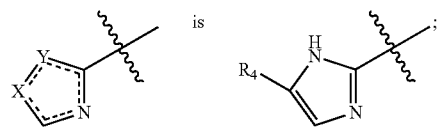

when X is NH,

Y is N and

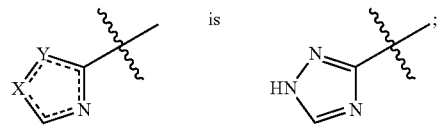

wherein $R_4$ is selected from H, NO$_2$, halogen, $C_{1-6}$ alkyl, halo-substituted $C_{1-6}$ alkyl, and —CN; preferably selected from H, NO$_2$, halogen, $C_{1-3}$ alkyl, halo-substituted $C_{1-3}$ alkyl, and —CN; and more preferably selected from H, NO$_2$, fluoro, chloro, methyl, ethyl, trifluoromethyl, trifluoroethyl, and —CN; and $R_5$ is selected from H, $C_{1-6}$ alkyl, $C_{1-6}$ alkoxy, halo-substituted $C_{1-6}$ alkyl, halo-substituted $C_{1-6}$ alkoxy, —OH, —NH$_2$, halogen, and —CN; preferably selected from H, $C_{1-3}$ alkyl, $C_{1-3}$ alkoxy, halo-substituted $C_{1-3}$ alkyl, halo-substituted $C_{1-3}$ alkoxy, —OH, —NH$_2$, halogen, and —CN; and more preferably selected from H, methyl, ethyl, methoxy, ethoxy, trifluoromethyl, trichloromethyl, trifluoroethyl, trichloroethyl, —OH, —NH$_2$, fluoro, and —CN.

In some preferred embodiments, the compound of the present invention is a compound of general formula I or a pharmaceutically acceptable salt, isomer, N-oxide, solvate, crystal, or prodrug thereof, wherein L is selected from —C(O)NH—, —NHC(O)NH—, and —NHC(O)—;

Z is selected from $(CH_2)_n$ or O, wherein n is selected from 0, 1, 2 and 3;

A is selected from 5- and 6-membered nitrogen-containing heterocyclic groups, and preferably selected from piperazinyl, tetrahydropyrrolyl, pyrrolyl, imidazolyl, pyridinyl, or substituted piperazinyl, tetrahydropyrrolyl, pyrrolyl, imidazolyl and pyridinyl, wherein the substituent(s) is(are) selected from alkyl, hydroxy, hydroxyalkyl, alkoxy, amino, mono-alkylamino, di-alkylamino, aminoacyl, alkylaminoacyl, arylaminoacyl, heteroarylaminoacyl, halogen, halo-substituted alkyl, and halo-substituted alkoxy;

$R_1$ is selected from H, $C_{1-6}$ alkyl, $C_{1-6}$ alkoxy, halo-substituted $C_{1-6}$ alkyl, halo-substituted $C_{1-6}$ alkoxy, —OH, —NH$_2$, halogen, and —CN; preferably selected from H, $C_{1-3}$ alkyl, $C_{1-3}$ alkoxy, halo-substituted $C_{1-3}$ alkyl, halo-substituted $C_{1-3}$ alkoxy, —OH, —NH$_2$, halogen, and —CN; and more preferably selected from H, methyl, ethyl, propyl, isopropyl, trifluoromethyl, fluoro, and chloro;

$R_2$ is selected from H, $C_{1-6}$ alkyl, $C_{1-6}$ alkoxy, halo-substituted $C_{1-6}$ alkyl, halo-substituted $C_{1-6}$ alkoxy, —OH, —NH$_2$, halogen, and —CN; preferably selected from H, $C_{1-3}$ alkyl, $C_{1-3}$ alkoxy, halo-substituted $C_{1-3}$ alkyl, halo-substituted $C_{1-3}$ alkoxy, —OH, —NH$_2$, halogen, and —CN; and more preferably selected from H, methyl, ethyl, propyl, isopropyl, trifluoromethyl, fluoro, and chloro; and B is

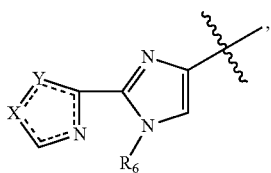

wherein X is selected from C($R_4$) and NH, and Y is selected from N and NH, wherein when X is C($R_4$), Y is NH and

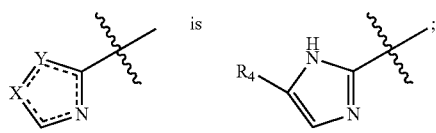

when X is NH,

Y is N and

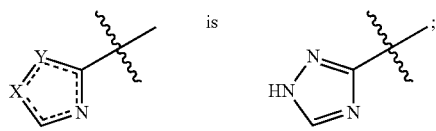

wherein $R_4$ is selected from H, NO$_2$, halogen, $C_{1-6}$ alkyl, halo-substituted $C_{1-6}$ alkyl, and —CN; preferably selected from H, NO$_2$, halogen, $C_{1-3}$ alkyl, halo-substituted $C_{1-3}$ alkyl, and —CN; and more preferably selected from H, NO$_2$, fluoro, chloro, methyl, ethyl, trifluoromethyl, trifluoroethyl, and —CN; and $R_6$ is selected from H, $C_{1-6}$ alkyl, preferably selected from H, $C_{1-3}$ alkyl, and more preferably selected from H, methyl, ethyl.

Preferably, the present invention provides a compound of general formula Ia or a pharmaceutically acceptable salt, isomer, N-oxide, solvate, crystal, or prodrug thereof,

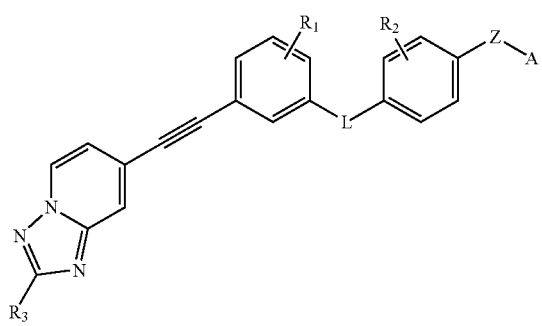

wherein

L is selected from —C(O)NH—, —NHC(O)NH—, and —NHC(O)—;

Z is selected from (CH$_2$)$_n$ or O, wherein n is selected from 0, 1, 2, 3, and 4;

A is selected from 5-, 6-, 7- and 8-membered nitrogen-containing heterocyclic groups;

$R_1$ is selected from H, alkyl, alkoxy, halo-substituted alkyl, halo-substituted alkoxy, —OH, —NH$_2$, halogen, and —CN;

$R_2$ is selected from H, alkyl, alkoxy, halo-substituted alkyl, halo-substituted alkoxy, —OH, —NH$_2$, halogen, and —CN; and $R_3$ is selected from H, amino, mono-alkylamino, di-alkylamino.

In some preferred embodiments, the present invention provides a compound of general formula Ia or a pharmaceutically acceptable salt, isomer, N-oxide, solvate, crystal, or prodrug thereof, wherein L is selected from —C(O)NH—, —NHC(O)NH—, and —NHC(O)—;

Z is selected from (CH$_2$)$_n$ or O, wherein n is selected from 0, 1 and 2;

A is selected from 5- and 6-membered nitrogen-containing heterocyclic groups, and preferably selected from piperazinyl, tetrahydropyrrolyl, pyridinyl, azabicycloalkyl, imidazolyl, pyrazolyl, pyrrolyl, triazolyl, pyridazinyl, pyrimidinyl, pyrazinyl, piperidinyl, triazinyl, or substituted piperazinyl, tetrahydropyrrolyl, pyridinyl, azabicycloalkyl, imidazolyl, pyrazolyl, pyrrolyl, triazolyl, pyridazinyl, pyrimidinyl, pyrazinyl, piperidinyl and triazinyl, wherein the substituent(s) is(are) selected from alkyl, hydroxy, hydroxyalkyl, alkoxy, amino, mono-alkylamino, di-alkylamino, aminoacyl, alkylaminoacyl, arylaminoacyl, heteroarylaminoacyl, halogen, halo-substituted alkyl, and halo-substituted alkoxy;

$R_1$ is selected from H, $C_{1-6}$ alkyl, $C_{1-6}$ alkoxy, halo-substituted $C_{1-6}$ alkyl, halo-substituted $C_{1-6}$ alkoxy, —OH, —NH$_2$, halogen, and —CN;

$R_2$ is selected from H, $C_{1-6}$ alkyl, $C_{1-6}$ alkoxy, halo-substituted $C_{1-6}$ alkyl, halo-substituted $C_{1-6}$ alkoxy, —OH, —NH$_2$, halogen, and —CN; and $R_3$ is selected from H, amino, mono-$C_{1-6}$ alkylamino, and bi-$C_{1-6}$ alkylamino.

In some more preferred embodiments, the compound of the present invention is a compound of general formula Ia or a pharmaceutically acceptable salt, isomer, N-oxide, solvate, crystal, or prodrug thereof, wherein L is selected from —C(O)NH—, —NHC(O)NH—, and —NHC(O)—;

Z is selected from (CH$_2$)$_n$ or O, wherein n is selected from 0 and 1;

A is selected from piperazinyl, tetrahydropyrrolyl, pyridinyl, azabicycloalkyl, imidazolyl, pyrazolyl, pyrrolyl, triazolyl, pyridazinyl, pyrimidinyl, pyrazinyl, piperidinyl, triazinyl, or substituted piperazinyl, tetrahydropyrrolyl, pyridinyl, azabicycloalkyl, imidazolyl, pyrazolyl, pyrrolyl, triazolyl, pyridazinyl, pyrimidinyl, pyrazinyl, piperidinyl and triazinyl, wherein the substituent(s) is(are) selected from $C_{1-6}$ alkyl, hydroxy, hydroxy $C_{1-6}$ alkyl, $C_{1-6}$ alkoxy, amino, mono-$C_{1-6}$ alkylamino, bi-$C_{1-6}$ alkylamino, aminoacyl, $C_{1-6}$ alkylaminoacyl, arylaminoacyl, heteroarylaminoacyl, halogen, halo-substituted $C_{1-6}$ alkyl, and halo-substituted $C_{1-6}$ alkoxy;

$R_1$ is selected from H, $C_{1-3}$ alkyl, $C_{1-3}$ alkoxy, halo-substituted $C_{1-3}$ alkyl, halo-substituted $C_{1-3}$ alkoxy, —OH, —NH$_2$, halogen, and —CN;

$R_2$ is selected from H, $C_{1-3}$ alkyl, $C_{1-3}$ alkoxy, halo-substituted $C_{1-3}$ alkyl, halo-substituted $C_{1-3}$ alkoxy, —OH, —NH$_2$, halogen, and —CN; and $R_3$ is selected from H, amino, mono-$C_{1-3}$ alkylamino, and bi-$C_{1-3}$ alkylamino.

In some more preferred embodiments, the compound of the present invention is a compound of general formula Ia or a pharmaceutically acceptable salt, isomer, N-oxide, solvate, crystal, or prodrug thereof, wherein L is selected from —C(O)NH—, —NHC(O)NH—, and —NHC(O)—;

Z is CH$_2$;

A is selected from piperazinyl, 4-methylpiperazin-1-yl, and 1-methylpyridin-4-yl;

$R_1$ is selected from H, methyl, ethyl, propyl, isopropyl, trifluoromethyl, fluoro, and chloro;

$R_2$ is selected from H, methyl, ethyl, propyl, isopropyl, trifluoromethyl, fluoro, and chloro; and $R_3$ is selected from H, amino, methylamino, ethylamino, propylamino, isopropylamino, dimethylamino, diethylamino, dipropylamino, diisopropylamino, N-methyl-N-ethylamino, N-methyl-N-propylamino, N-methyl-N-isopropylamino, N-ethyl-N-propylamino, N-ethyl-N-isopropylamino, N-propyl-N-isopropylamino.

Preferably, the present invention provides a compound of general formula Ib or a pharmaceutically acceptable salt, isomer, N-oxide, solvate, crystal, or prodrug thereof,

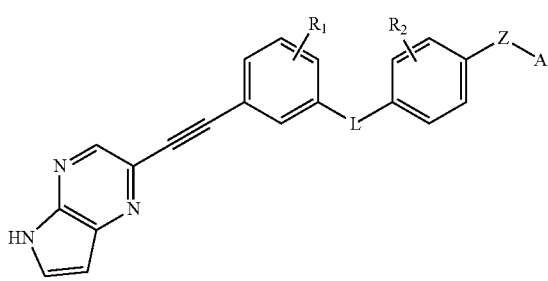

(Ib)

wherein

L is selected from —C(O)NH—, —NHC(O)NH—, and —NHC(O)—;

Z is selected from (CH$_2$)$_n$ or O, wherein n is selected from 0, 1, 2, 3, and 4;

A is selected from 5-, 6-, 7- and 8-membered nitrogen-containing heterocyclic groups;

$R_1$ is selected from H, alkyl, alkoxy, halo-substituted alkyl, halo-substituted alkoxy, —OH, —NH$_2$, halogen, and —CN; and $R_2$ is selected from H, alkyl, alkoxy, halo-substituted alkyl, halo-substituted alkoxy, —OH, —NH$_2$, halogen, and —CN.

In some preferred embodiments, the compound of the present invention is a compound of general formula Ib or a pharmaceutically acceptable salt, isomer, N-oxide, solvate, crystal, or prodrug thereof, wherein L is selected from —C(O)NH—, —NHC(O)NH—, and —NHC(O)—;

Z is selected from (CH$_2$)$_n$ or O, wherein n is selected from 0, 1 and 2;

A is selected from is selected from piperazinyl, tetrahydropyrrolyl, pyridinyl, azabicycloalkyl, imidazolyl, pyrazolyl, pyrrolyl, triazolyl, pyridazinyl, pyrimidinyl, pyrazinyl, piperidinyl, triazinyl, or substituted piperazinyl, tetrahydropyrrolyl, pyridinyl, azabicycloalkyl, imidazolyl, pyrazolyl, pyrrolyl, triazolyl, pyridazinyl, pyrimidinyl, pyrazinyl, piperidinyl and triazinyl, wherein the substituent(s) is(are) selected from alkyl, hydroxy, hydroxyalkyl, alkoxy, amino, mono-alkylamino, di-alkylamino, aminoacyl, alkylaminoacyl, arylaminoacyl, heteroarylaminoacyl, halogen, halo-substituted alkyl, and halo-substituted alkoxy;

$R_1$ is selected from H, $C_{1-6}$ alkyl, $C_{1-6}$ alkoxy, halo-substituted $C_{1-6}$ alkyl, halo-substituted $C_{1-6}$ alkoxy, —OH, —NH$_2$, halogen, and —CN; and $R_2$ is selected from H, $C_{1-6}$ alkyl, $C_{1-6}$ alkoxy, halo-substituted $C_{1-6}$ alkyl, halo-substituted $C_{1-6}$ alkoxy, —OH, —NH$_2$, halogen, and —CN.

In some more preferred embodiments, the compound of the present invention is a compound of general formula Ib or a pharmaceutically acceptable salt, isomer, N-oxide, solvate, crystal, or prodrug thereof, wherein L is selected from —C(O)NH—, —NHC(O)NH—, and —NHC(O)—;

Z is selected from (CH$_2$)$_n$ or O, wherein n is selected from 0 and 1;

A is selected from piperazinyl, tetrahydropyrrolyl, pyridinyl, azabicycloalkyl, imidazolyl, pyrazolyl, pyrrolyl, triazolyl, pyridazinyl, pyrimidinyl, pyrazinyl, piperidinyl, triazinyl, or substituted piperazinyl, tetrahydropyrrolyl, pyridinyl, azabicycloalkyl, imidazolyl, pyrazolyl, pyrrolyl, triazolyl, pyridazinyl, pyrimidinyl, pyrazinyl, piperidinyl and triazinyl, wherein the substituent(s) is(are) selected from $C_{1-6}$ alkyl, hydroxy, hydroxy $C_{1-6}$ alkyl, $C_{1-6}$ alkoxy, amino, mono-$C_{1-6}$ alkylamino, bi-$C_{1-6}$ alkylamino, aminoacyl, $C_{1-6}$ alkylaminoacyl, arylaminoacyl, heteroarylaminoacyl, halogen, halo-substituted $C_{1-6}$ alkyl, and halo-substituted $C_{1-6}$ alkoxy;

$R_1$ is selected from H, $C_{1-3}$ alkyl, $C_{1-3}$ alkoxy, halo-substituted $C_{1-3}$ alkyl, halo-substituted $C_{1-3}$ alkoxy, —OH, —NH$_2$, halogen, and —CN; and $R_2$ is selected from H, $C_{1-3}$ alkyl, $C_{1-3}$ alkoxy, halo-substituted $C_{1-3}$ alkyl, halo-substituted $C_{1-3}$ alkoxy, —OH, —NH$_2$, halogen, and —CN.

In some still more preferred embodiments, the compound of the present invention is a compound of general formula Ib or a pharmaceutically acceptable salt, isomer, N-oxide, solvate, crystal, or prodrug thereof, wherein L is selected from —C(O)NH—, —NHC(O)NH—, and —NHC(O)—;

Z is CH$_2$;

A is selected from piperazinyl, 4-methylpiperazin-1-yl, and 1-methylpyridin-4-yl;

$R_1$ is selected from H, methyl, ethyl, propyl, isopropyl, trifluoromethyl, fluoro, and chloro; and $R_2$ is selected from H, methyl, ethyl, propyl, isopropyl, trifluoromethyl, fluoro, and chloro.

Preferably, the present invention provides a compound of general formula Ic or a pharmaceutically acceptable salt, isomer, N-oxide, solvate, crystal, or prodrug thereof,

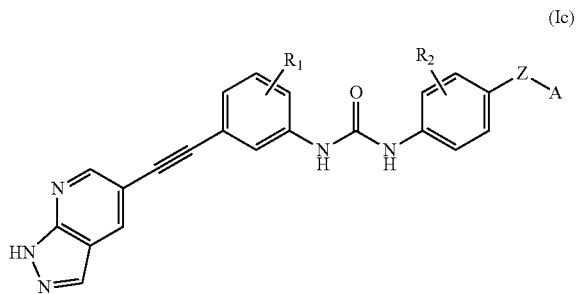

(Ic)

wherein
Z is selected from (CH$_2$) or O, wherein n is selected from 0, 1, 2, 3, and 4;
A is selected from 5-, 6-, 7- and 8-membered nitrogen-containing heterocyclic groups;
R$_1$ is selected from H, alkyl, alkoxy, halo-substituted alkyl, halo-substituted alkoxy, —OH, —NH$_2$, halogen, and —CN; and
R$_2$ is selected from H, alkyl, alkoxy, halo-substituted alkyl, halo-substituted alkoxy, —OH, —NH$_2$, halogen, and —CN.

In some preferred embodiments, the compound of the present invention is a compound of general formula Ic or a pharmaceutically acceptable salt, isomer, N-oxide, solvate, crystal, or prodrug thereof, wherein
Z is selected from (CH$_2$)$_n$ or O, wherein n is selected from 0, 1 and 2;
A is selected from piperazinyl, tetrahydropyrrolyl, pyridinyl, azabicycloalkyl, imidazolyl, pyrazolyl, pyrrolyl, triazolyl, pyridazinyl, pyrimidinyl, pyrazinyl, piperidinyl, triazinyl, or substituted piperazinyl, tetrahydropyrrolyl, pyridinyl, azabicycloalkyl, imidazolyl, pyrazolyl, pyrrolyl, triazolyl, pyridazinyl, pyrimidinyl, pyrazinyl, piperidinyl and triazinyl, wherein the substituent(s) is(are) selected from alkyl, hydroxy, hydroxyalkyl, alkoxy, amino, mono-alkylamino, di-alkylamino, aminoacyl, alkylaminoacyl, arylaminoacyl, heteroarylaminoacyl, halogen, halo-substituted alkyl, and halo-substituted alkoxy;
R$_1$ is selected from H, C$_{1-6}$ alkyl, C$_{1-6}$ alkoxy, halo-substituted C$_{1-6}$ alkyl, halo-substituted C$_{1-6}$ alkoxy, —OH, —NH$_2$, halogen, and —CN; and
R$_2$ is selected from H, C$_{1-6}$ alkyl, C$_{1-6}$ alkoxy, halo-substituted C$_{1-6}$ alkyl, halo-substituted C$_{1-6}$ alkoxy, —OH, —NH$_2$, halogen, and —CN.

In some more preferred embodiments, the compound of the present invention is a compound of general formula Ic or a pharmaceutically acceptable salt, isomer, N-oxide, solvate, crystal, or prodrug thereof, wherein
Z is selected from (CH$_2$)$_n$ or O, wherein n is selected from 0 and 1;
A is selected from piperazinyl, tetrahydropyrrolyl, pyridinyl, azabicycloalkyl, imidazolyl, pyrazolyl, pyrrolyl, triazolyl, pyridazinyl, pyrimidinyl, pyrazinyl, piperidinyl, triazinyl, or substituted piperazinyl, tetrahydropyrrolyl, pyridinyl, azabicycloalkyl, imidazolyl, pyrazolyl, pyrrolyl, triazolyl, pyridazinyl, pyrimidinyl, pyrazinyl, piperidinyl and triazinyl, wherein the substituent(s) is(are) selected from C$_{1-6}$ alkyl, hydroxy, hydroxy C$_{1-6}$ alkyl, C$_{1-6}$ alkoxy, amino, mono-C$_{1-6}$ alkylamino, bi-C$_{1-6}$ alkylamino, aminoacyl, C$_{1-6}$ alkylaminoacyl, arylaminoacyl, heteroarylaminoacyl, halogen, halo-substituted C$_{1-6}$ alkyl, and halo-substituted C$_{1-6}$ alkoxy;

R$_1$ is selected from H, C$_{1-3}$ alkyl, C$_{1-3}$ alkoxy, halo-substituted C$_{1-3}$ alkyl, halo-substituted C$_{1-3}$ alkoxy, —OH, —NH$_2$, halogen, and —CN; and
R$_2$ is selected from H, C$_{1-3}$ alkyl, C$_{1-3}$ alkoxy, halo-substituted C$_{1-3}$ alkyl, halo-substituted C$_{1-3}$ alkoxy, —OH, —NH$_2$, halogen, and —CN.

In some still more preferred embodiments, the compound of the present invention is a compound of general formula Ic or a pharmaceutically acceptable salt, isomer, N-oxide, solvate, crystal, or prodrug thereof, wherein
Z is CH$_2$;
A is selected from piperazinyl, 4-methylpiperazin-1-yl, and 1-methylpyridin-4-yl;
R$_1$ is selected from H, methyl, ethyl, propyl, isopropyl, trifluoromethyl, fluoro, and chloro;
R$_2$ is selected from H, methyl, ethyl, propyl, isopropyl, trifluoromethyl, fluoro, and chloro.

Preferably, the present invention provides a compound of general formula Id or a pharmaceutically acceptable salt, isomer, N-oxide, solvate, crystal, or prodrug thereof,

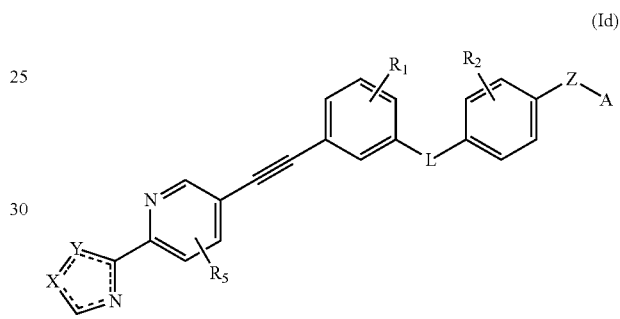

(Id)

wherein
L is selected from —C(O)NH—, —NHC(O)NH—, and —NHC(O)—;
Z is selected from (CH$_2$)$_n$ or O, wherein n is selected from 0, 1, 2, 3, and 4;
A is selected from 5-, 6-, 7- and 8-membered nitrogen-containing heterocyclic groups;
R$_1$ is selected from H, alkyl, alkoxy, halo-substituted alkyl, halo-substituted alkoxy, —OH, —NH$_2$, halogen, and —CN;
R$_2$ is selected from H, alkyl, alkoxy, halo-substituted alkyl, halo-substituted alkoxy, —OH, —NH$_2$, halogen, and —CN;
X is selected from C(R$_4$) and NH, and Y is selected from N and NH, wherein when X is C(R$_4$), Y is NH and

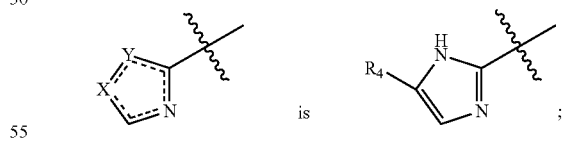

is when X is NH, Y is N and

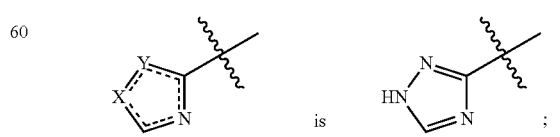

is wherein R$_4$ is selected from H, NO$_2$, halogen, alkyl, halo-substituted alkyl, and —CN; and $R_5$ is selected from H, alkyl, alkoxy, halo-substituted alkyl, halo-substituted alkoxy, —OH, —NH$_2$, halogen, and —CN.

In some preferred embodiments, the compound of the present invention is a compound of general formula Id or a pharmaceutically acceptable salt, isomer, N-oxide, solvate, crystal, or prodrug thereof, wherein L is selected from —C(O)NH—, —NHC(O)NH—, and —NHC(O)—;

Z is selected from (CH$_2$)$_n$ or O, wherein n is selected from 0, 1 and 2;

A is selected from piperazinyl, tetrahydropyrrolyl, pyridinyl, azabicycloalkyl, imidazolyl, pyrazolyl, pyrrolyl, triazolyl, pyridazinyl, pyrimidinyl, pyrazinyl, piperidinyl, triazinyl, or substituted piperazinyl, tetrahydropyrrolyl, pyridinyl, azabicycloalkyl, imidazolyl, pyrazolyl, pyrrolyl, triazolyl, pyridazinyl, pyrimidinyl, pyrazinyl, piperidinyl and triazinyl, wherein the substituent(s) is(are) selected from alkyl, hydroxy, hydroxyalkyl, alkoxy, amino, mono-alkylamino, di-alkylamino, aminoacyl, alkylaminoacyl, arylaminoacyl, heteroarylaminoacyl, halogen, halo-substituted alkyl, and halo-substituted alkoxy;

$R_1$ is selected from H, $C_{1-6}$ alkyl, $C_{1-6}$ alkoxy, halo-substituted $C_{1-6}$ alkyl, halo-substituted $C_{1-6}$ alkoxy, —OH, —NH$_2$, halogen, and —CN;

$R_2$ is selected from H, $C_{1-6}$ alkyl, $C_{1-6}$ alkoxy, halo-substituted $C_{1-6}$ alkyl, halo-substituted $C_{1-6}$ alkoxy, —OH, —NH$_2$, halogen, and —CN;

X is selected from C($R_4$) and NH, and Y is selected from N and NH, wherein when X is C($R_4$), Y is NH and

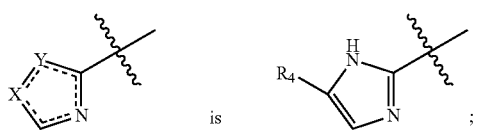

is when X is NH, Y is N and

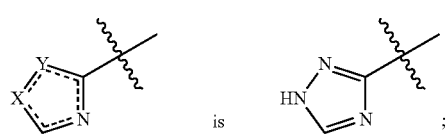

is wherein $R_4$ is selected from H, NO$_2$, halogen, $C_{1-6}$ alkyl, halo-substituted $C_{1-6}$ alkyl, and —CN; and $R_5$ is selected from H, $C_{1-6}$ alkyl, $C_{1-6}$ alkoxy, halo-substituted $C_{1-6}$ alkyl, halo-substituted $C_{1-6}$ alkoxy, —OH, —NH$_2$, halogen, and —CN.

In some more preferred embodiments, the compound of the present invention is a compound of general formula Id or a pharmaceutically acceptable salt, isomer, N-oxide, solvate, crystal, or prodrug thereof, wherein L is selected from —C(O)NH—, —NHC(O)NH—, and —NHC(O)—;

Z is selected from (CH$_2$)$_n$ or O, wherein n is selected from 0 and 1;

A is selected from piperazinyl, tetrahydropyrrolyl, pyridinyl, azabicycloalkyl, imidazolyl, pyrazolyl, pyrrolyl, triazolyl, pyridazinyl, pyrimidinyl, pyrazinyl, piperidinyl, triazinyl, or substituted piperazinyl, tetrahydropyrrolyl, pyridinyl, azabicycloalkyl, imidazolyl, pyrazolyl, pyrrolyl, triazolyl, pyridazinyl, pyrimidinyl, pyrazinyl, piperidinyl and triazinyl, wherein the substituent(s) is(are) selected from $C_{1-6}$ alkyl, hydroxy, hydroxy $C_{1-6}$ alkyl, $C_{1-6}$ alkoxy, amino, mono-$C_{1-6}$ alkylamino, bi-$C_{1-6}$ alkylamino, aminoacyl, $C_{1-6}$ alkylaminoacyl, arylaminoacyl, heteroarylaminoacyl, halogen, halo-substituted $C_{1-6}$ alkyl, and halo-substituted $C_{1-6}$ alkoxy;

$R_1$ is selected from H, $C_{1-3}$ alkyl, $C_{1-3}$ alkoxy, halo-substituted $C_{1-3}$ alkyl, halo-substituted $C_{1-3}$ alkoxy, —OH, —NH$_2$, halogen, and —CN;

$R_2$ is selected from H, $C_{1-3}$ alkyl, $C_{1-3}$ alkoxy, halo-substituted $C_{1-3}$ alkyl, halo-substituted $C_{1-3}$ alkoxy, —OH, —NH$_2$, halogen, and —CN;

X is selected from C($R_4$) and NH, and Y is selected from N and NH, wherein when X is C($R_4$), Y is NH and

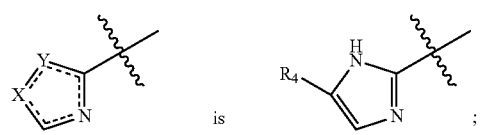

is when X is NH, Y is N and

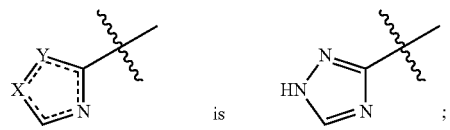

is wherein $R_4$ is selected from H, NO$_2$, halogen, $C_{1-3}$ alkyl, halo-substituted $C_{1-3}$ alkyl, and —CN; and $R_5$ is selected from H, $C_{1-3}$ alkyl, $C_{1-3}$ alkoxy, halo-substituted $C_{1-3}$ alkyl, halo-substituted $C_{1-3}$ alkoxy, —OH, —NH$_2$, halogen, and —CN.

In some still more preferred embodiments, the compound of the present invention is a compound of general formula Id or a pharmaceutically acceptable salt, isomer, N-oxide, solvate, crystal, or prodrug thereof, wherein L is selected from —C(O)NH—, —NHC(O)NH—, and —NHC(O)—;

Z is CH$_2$;

A is selected from piperazinyl, 4-methylpiperazin-1-yl, and 1-methylpyridin-4-yl;

$R_1$ is selected from H, methyl, ethyl, propyl, isopropyl, trifluoromethyl, fluoro, and chloro;

$R_2$ is selected from H, methyl, ethyl, propyl, isopropyl, trifluoromethyl, fluoro, and chloro;

X is selected from C($R_4$) and NH, and Y is selected from N and NH, wherein when X is C($R_4$), Y is NH and

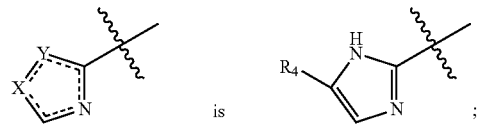

is when X is NH, Y is N and

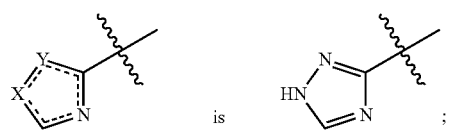

is wherein R₄ is selected from H, NO₂, fluoro, chloro, methyl, ethyl, trifluoromethyl, trifluoroethyl, and —CN; and R₅ is selected from H, methyl, ethyl, propyl, isopropyl, trifluoromethyl, fluoro, and chloro.

Preferably, the present invention provides a compound of general formula Ie or a pharmaceutically acceptable salt, isomer, N-oxide, solvate, crystal, or prodrug thereof,

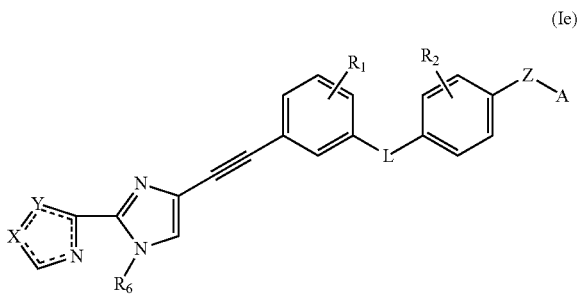
(Ie)

wherein
L is selected from —C(O)NH—, —NHC(O)NH—, and —NHC(O)—;

Z is selected from (CH₂)ₙ or O, wherein n is selected from 0, 1, 2, 3, and 4;

A is selected from 5-, 6-, 7- and 8-membered nitrogen-containing heterocyclic groups;

R₁ is selected from H, alkyl, alkoxy, halo-substituted alkyl, halo-substituted alkoxy, —OH, —NH₂, halogen, and —CN;

R₂ is selected from H, alkyl, alkoxy, halo-substituted alkyl, halo-substituted alkoxy, —OH, —NH₂, halogen, and —CN;

X is selected from C(R₄) and NH, and Y is selected from N and NH, wherein when X is C(R₄), Y is NH and

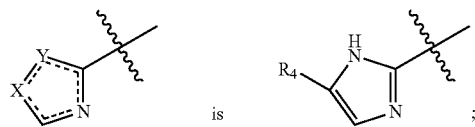
is ;

when X is NH, Y is N and

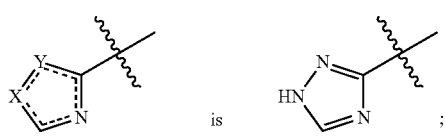
is ;

wherein R₄ is selected from H, NO₂, halogen, alkyl, halo-substituted alkyl, and —CN; and R₆ is selected from H, and alkyl.

In some preferred embodiments, the compound of the present invention is a compound of general formula Ie or a pharmaceutically acceptable salt, isomer, N-oxide, solvate, crystal, or prodrug thereof, wherein L is selected from —C(O)NH—, —NHC(O)NH—, and —NHC(O)—;

Z is selected from (CH₂)ₙ or O, wherein n is selected from 0, 1 and 2;

A is selected from piperazinyl, tetrahydropyrrolyl, pyridinyl, azabicycloalkyl, imidazolyl, pyrazolyl, pyrrolyl, triazolyl, pyridazinyl, pyrimidinyl, pyrazinyl, piperidinyl, triazinyl, or substituted piperazinyl, tetrahydropyrrolyl, pyridinyl, azabicycloalkyl, imidazolyl, pyrazolyl, pyrrolyl, triazolyl, pyridazinyl, pyrimidinyl, pyrazinyl, piperidinyl and triazinyl, wherein the substituent(s) is(are) selected from alkyl, hydroxy, hydroxyalkyl, alkoxy, amino, mono-alkylamino, di-alkylamino, aminoacyl, alkylaminoacyl, arylaminoacyl, heteroarylaminoacyl, halogen, halo-substituted alkyl, and halo-substituted alkoxy;

R₁ is selected from H, C₁₋₆ alkyl, C₁₋₆ alkoxy, halo-substituted C₁₋₆ alkyl, halo-substituted C₁₋₆ alkoxy, —OH, —NH₂, halogen, and —CN;

R₂ is selected from H, C₁₋₆ alkyl, C₁₋₆ alkoxy, halo-substituted C₁₋₆ alkyl, halo-substituted C₁₋₆ alkoxy, —OH, —NH₂, halogen, and —CN;

X is selected from C(R₄) and NH, and Y is selected from N and NH, wherein when X is C(R₄),

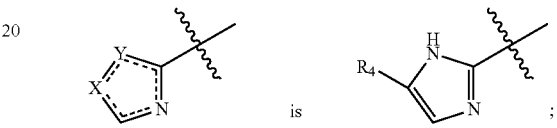
is ;

Y is NH and when X is NH, Y is N and

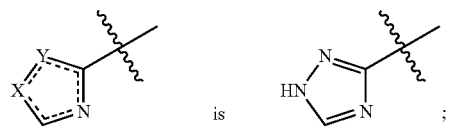
is ;

wherein R₄ is selected from H, NO₂, halogen, C₁₋₆ alkyl, halo-substituted C₁₋₆ alkyl, and —CN; and R₆ is selected from H, and C₁₋₆ alkyl.

In some more preferred embodiments, the compound of the present invention is a compound of general formula Ie or a pharmaceutically acceptable salt, isomer, N-oxide, solvate, crystal, or prodrug thereof, wherein L is selected from —C(O)NH—, —NHC(O)NH—, and —NHC(O)—;

Z is selected from (CH₂)ₙ or O, wherein n is selected from 0 and 1;

A is selected from piperazinyl, tetrahydropyrrolyl, pyridinyl, azabicycloalkyl, imidazolyl, pyrazolyl, pyrrolyl, triazolyl, pyridazinyl, pyrimidinyl, pyrazinyl, piperidinyl, triazinyl, or substituted piperazinyl, tetrahydropyrrolyl, pyridinyl, azabicycloalkyl, imidazolyl, pyrazolyl, pyrrolyl, triazolyl, pyridazinyl, pyrimidinyl, pyrazinyl, piperidinyl and triazinyl, wherein the substituent(s) is(are) selected from C₁₋₆ alkyl, hydroxy, hydroxy C₁₋₆ alkyl, C₁₋₆ alkoxy, amino, mono-C₁₋₆ alkylamino, bi-C₁₋₆ alkylamino, aminoacyl, C₁₋₆ alkylaminoacyl, arylaminoacyl, heteroarylaminoacyl, halogen, halo-substituted C₁₋₆ alkyl, and halo-substituted C₁₋₆ alkoxy;

R₁ is selected from H, C₁₋₃ alkyl, C₁₋₃ alkoxy, halo-substituted C₁₋₃ alkyl, halo-substituted C₁₋₃ alkoxy, —OH, —NH₂, halogen, and —CN;

R₂ is selected from H, C₁₋₃ alkyl, C₁₋₃ alkoxy, halo-substituted C₁₋₃ alkyl, halo-substituted C₁₋₃ alkoxy, —OH, —NH₂, halogen, and —CN;

X is selected from C(R₄) and NH, and Y is selected from N and NH, wherein when X is C(R₄), Y is NH and

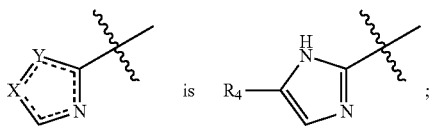 is 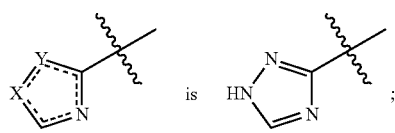 ;

when X is NH, Y is N and

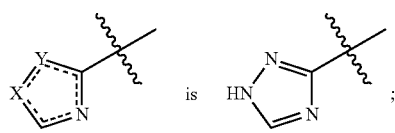 is ... ;

wherein $R_4$ is selected from H, $NO_2$, halogen, $C_{1-3}$ alkyl, halo-substituted $C_{1-3}$ alkyl, and —CN; and $R_6$ is selected from H, and $C_{1-3}$ alkyl.

In some still more preferred embodiments, the compound of the present invention is a compound of general formula Ie or a pharmaceutically acceptable salt, isomer, N-oxide, solvate, crystal, or prodrug thereof, wherein L is selected from —C(O)NH—, —NHC(O)NH—, and —NHC(O)—;

Z is $CH_2$;

A is selected from piperazinyl, 4-methylpiperazin-1-yl, and 1-methylpyridin-4-yl;

$R_1$ is selected from H, methyl, ethyl, propyl, isopropyl, trifluoromethyl, fluoro, and chloro;

$R_2$ is selected from H, methyl, ethyl, propyl, isopropyl, trifluoromethyl, fluoro, chloro, X is selected from $C(R_4)$ and NH, and Y is selected from N and NH, wherein when X is $C(R_4)$, Y is NH and

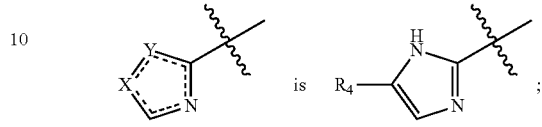 ;

when X is NH, Y is N and

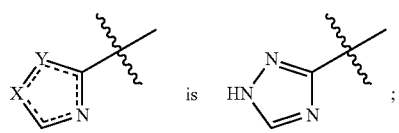 ;

wherein $R_4$ is selected from H, $NO_2$, fluoro, chloro, methyl, ethyl, trifluoromethyl, trifluoroethyl, and —CN; and $R_6$ is selected from H, methyl, and ethyl.

The present invention provides the following specific compounds:

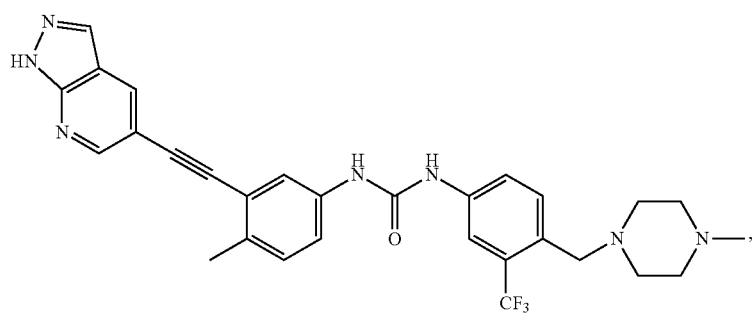

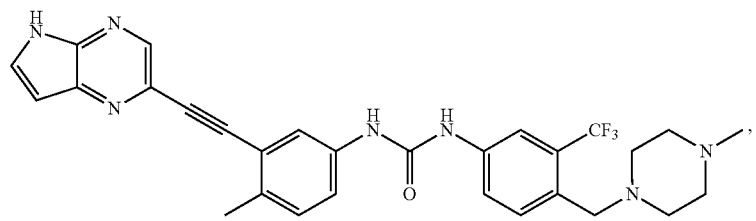

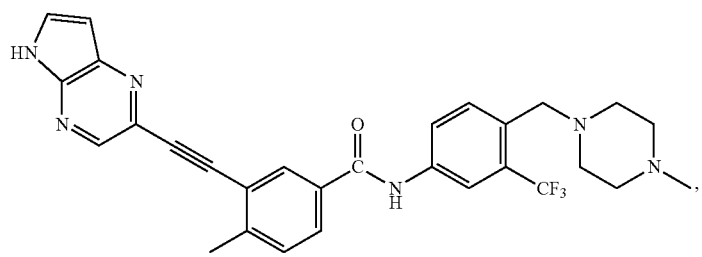

-continued
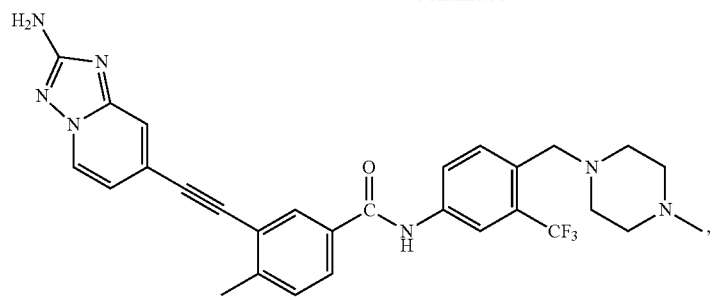
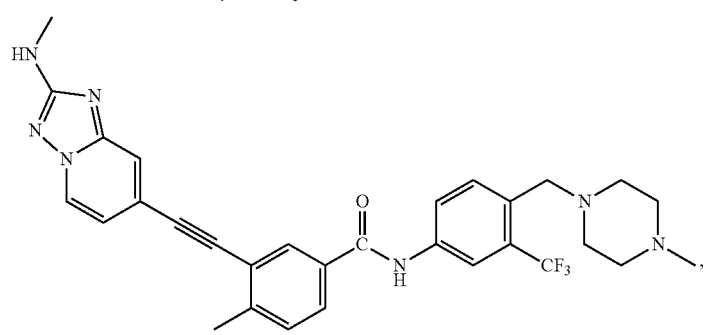
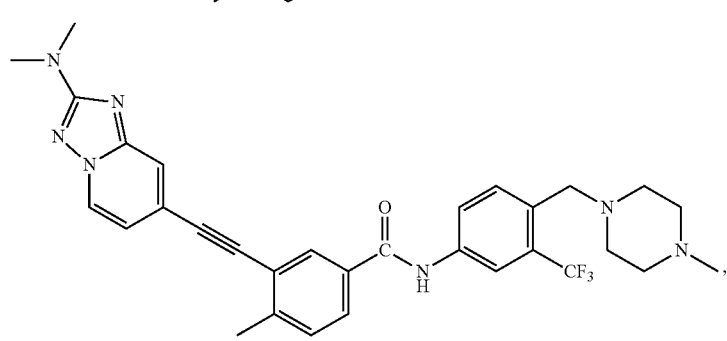
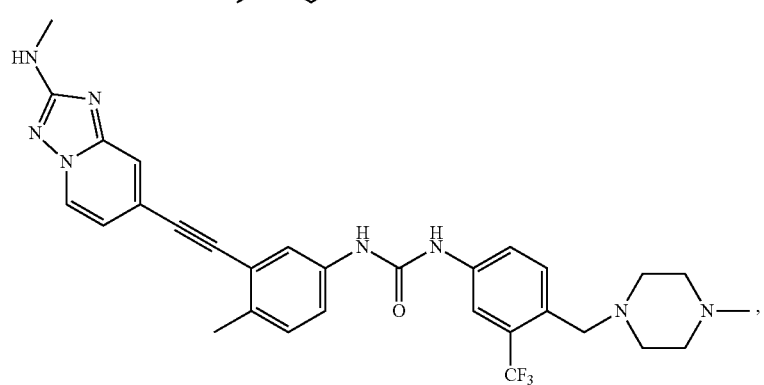
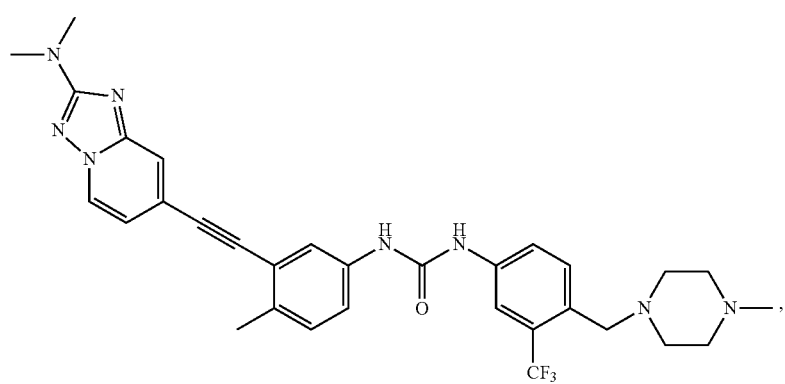

-continued
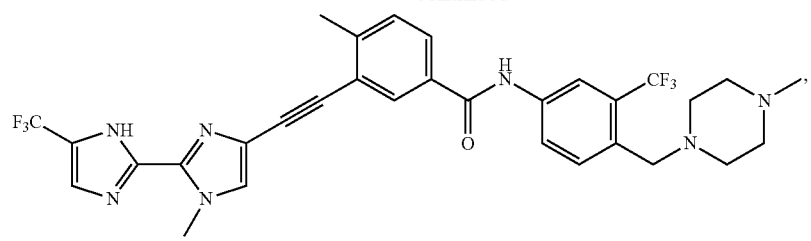
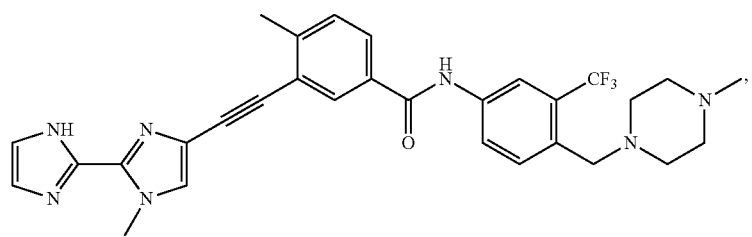
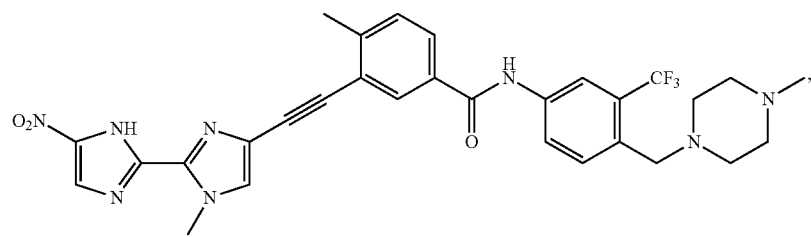
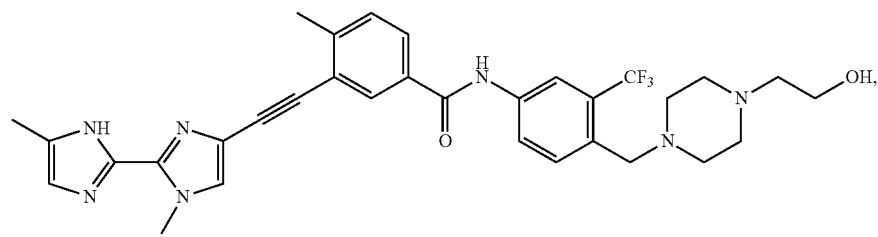
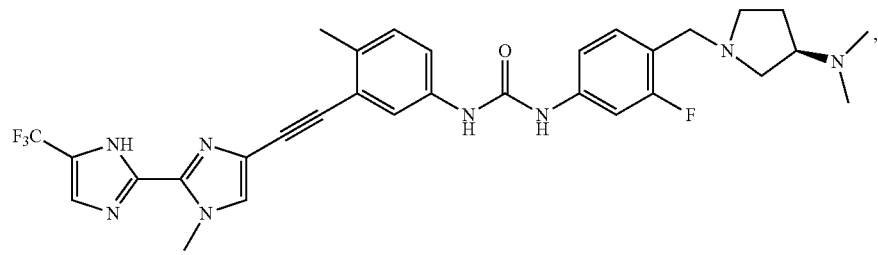
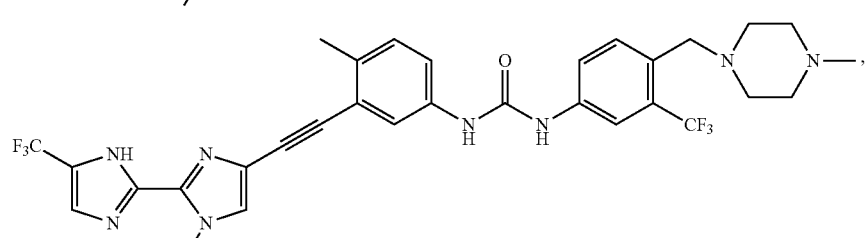
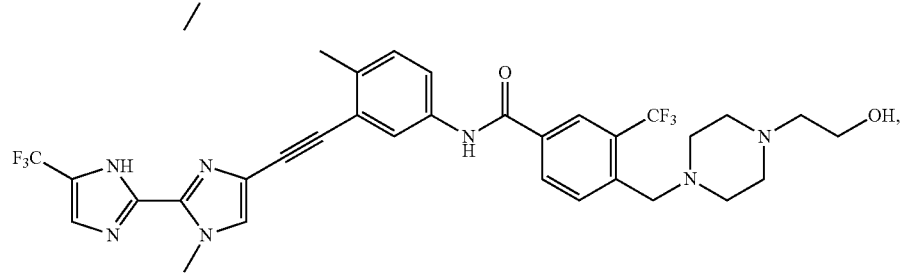

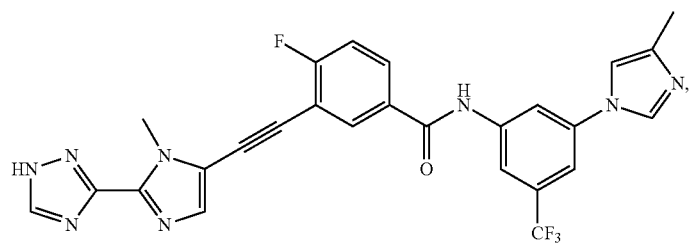
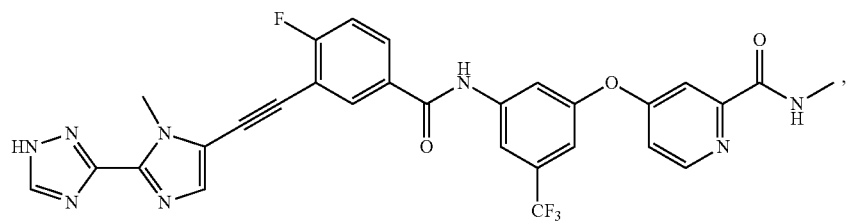
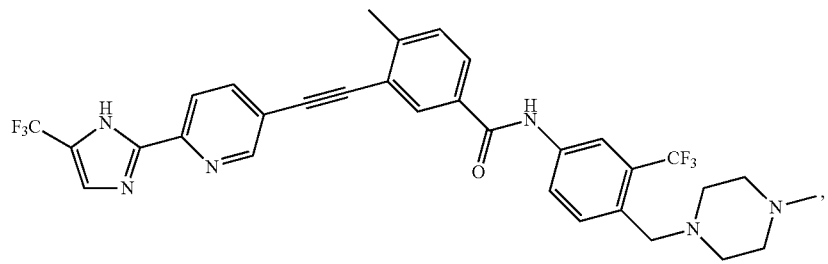
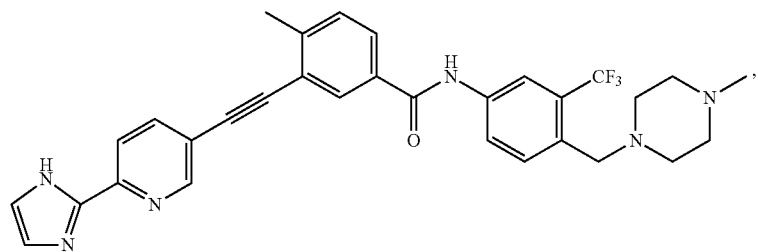
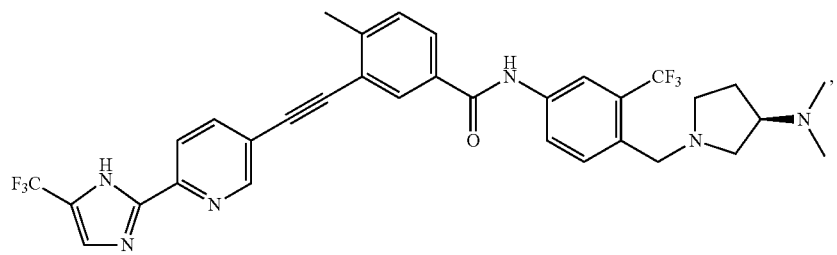
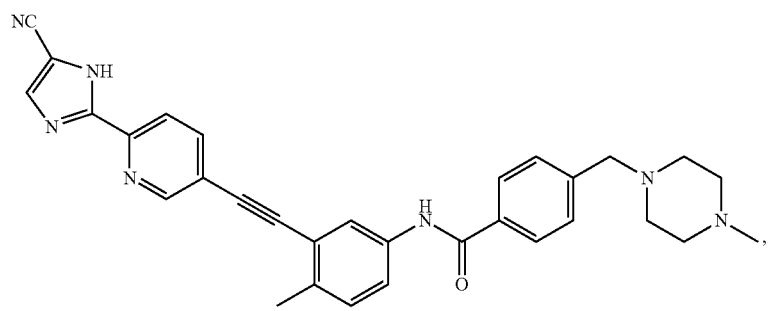

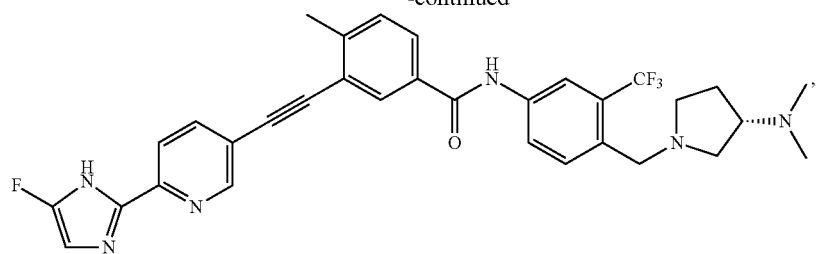
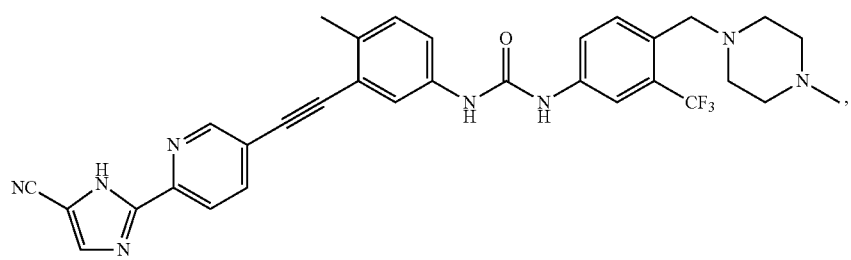
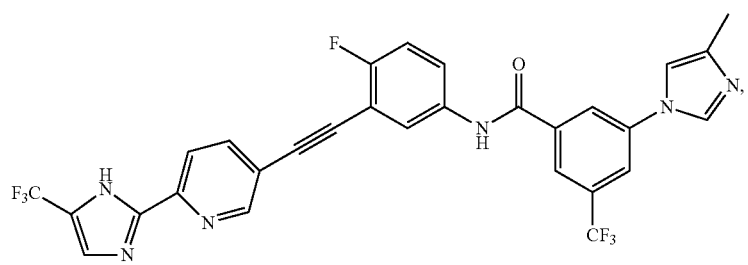
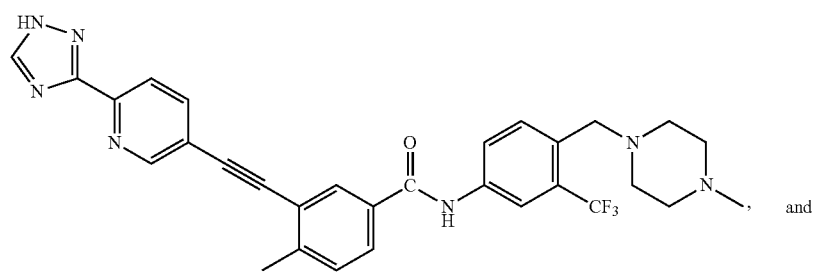
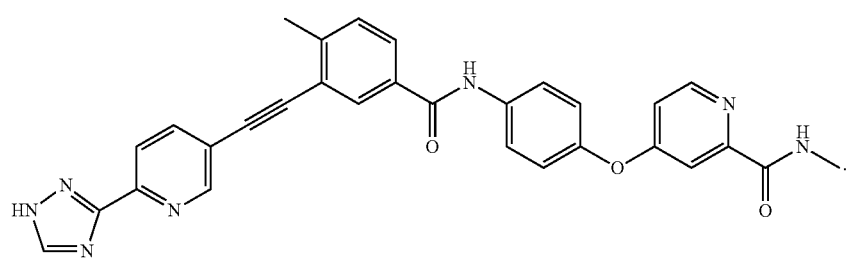

In a second aspect, the present invention provides a method of preparing the compounds of the general formulas according to the present invention. A method of preparing the compound of general formula I comprises the following steps:

1. Synthetic route of the compound of general formula I wherein L is —C(O)NH—:

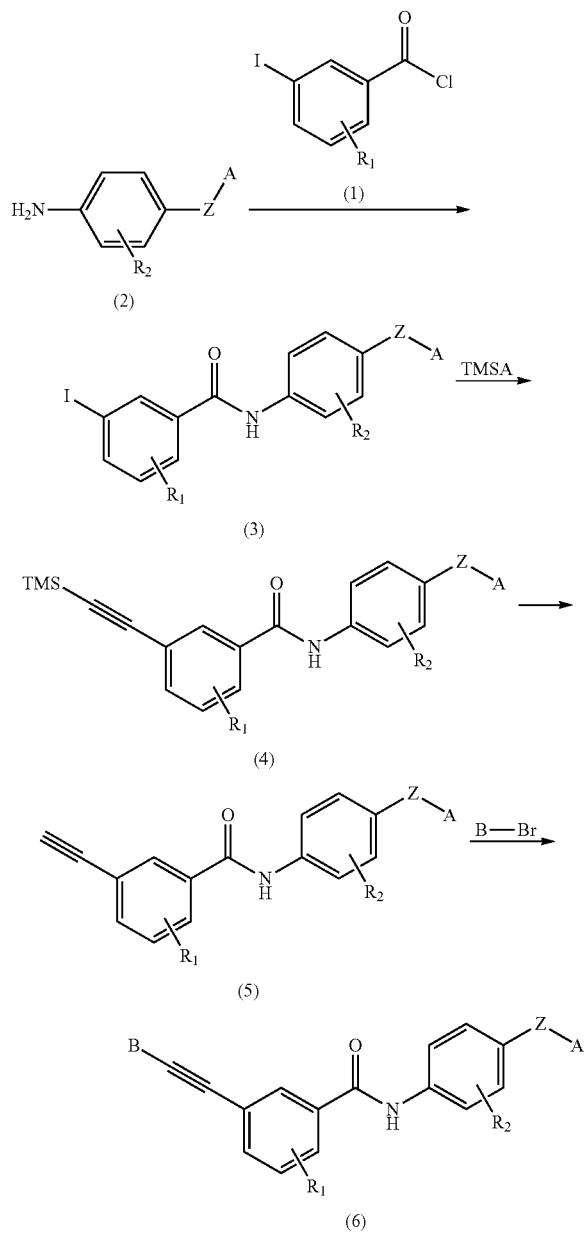

wherein TMSA is trimethylsilylacetylene, and $R_1$, $R_2$, Z, A and B are defined as above.

The synthetic process is summarized below:

Step 1: Preparation of Compound (3)

Compound (2) is reacted with Compound (1) at room temperature under alkaline condition, for example, in the presence of triethylamine, to give compound (3).

Step 2: Preparation of Compound (4)

Compound (3), $Pd(PPh_3)_2Cl_2$ and CuI are subjected to Sonogashira reaction with trimethylsilylacetylene under alkaline condition and the protection of an inert gas atmosphere, to give compound (4).

Step 3: Preparation of Compound (5)

Compound (4) is deprotected in the presence of potassium carbonate, to give compound (5).

Step 4: Preparation of Compound (6)

Compound (5), B—Br, $Pd(PPh_3)_2Cl_2$, CuI, $Cs_2CO_3$ and N,N-diisopropylethylamine are subjected to Sonogashira reaction under the protection of an inert gas atmosphere, to obtain the title compound, that is, Compound (6).

2. Synthetic route of the compound of general formula I wherein L is —NHC(O)—

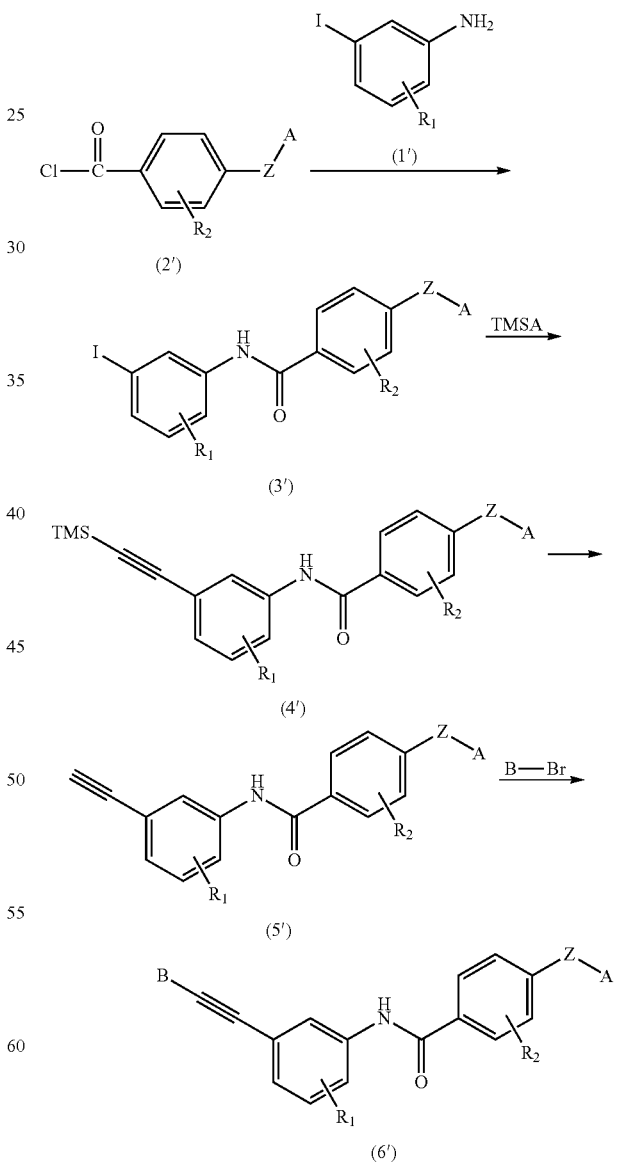

wherein TMSA is trimethylsilylacetylene, and $R_1$, $R_2$, Z, A and B are defined as above.

The preparation process is the same as the synthetic route of the compound of general formula I wherein L is —C(O)NH—.

3. Synthetic route of the compound of general formula I wherein L is —NHC(O)NH—:

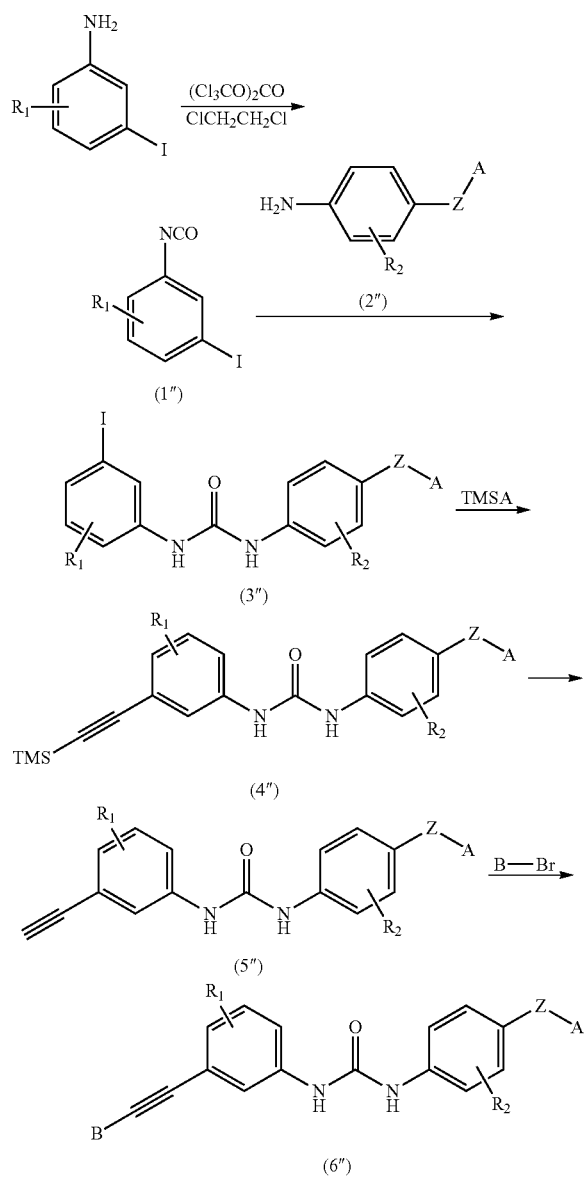

Step 1: Preparation of Compound (3")

R₁ substituted 3-iodoaniline is reacted with triphosgene in ClCH₂CH₂Cl, to give Compound (1"). The obtained Compound (1") is reacted with Compound (2") at room temperature under alkaline condition, for example, in the presence of triethylamine, to give Compound (3").

Step 2: Preparation of Compound (4")

Compound (3"), Pd(PPh₃)₂Cl₂ and CuI are subjected to Sonogashira reaction with trimethylsilylacetylene under alkaline condition and the protection of an inert gas atmosphere, to give compound (4").

Step 3: Preparation of Compound (5")

Compound (4") is deprotected in the presence of potassium carbonate, to give compound (5").

Step 4: Preparation of Compound (6")

Compound (5"), B—Br, Pd(PPh₃)₂Cl₂, CuI, Cs₂CO₃ and N,N-diisopropylethylamine are subjected to Sonogashira reaction under the protection of an inert gas atmosphere, to obtain the title compound, that is, Compound (6").

In a third aspect, the present invention provides a pharmaceutical composition comprising the compound according to the present invention or a pharmaceutically acceptable salt, isomer, N-oxide, solvate, crystal, or prodrug thereof.

In some embodiments, the present invention provides a pharmaceutical composition comprising the compound according to the present invention or an isomer, N-oxide, solvate, crystal, or prodrug thereof, and further comprising one or more agents selected from a group consisting of tyrosine protease inhibitor, EGFR inhibitors, VEGFR inhibitors, Bcr-Abl inhibitors, c-kit inhibitors, c-Met inhibitors, Raf inhibitors, MEK inhibitors, Histone deacetylase inhibitors, VEGF antibodies, EGF antibodies, HIV protein kinase inhibitors, HMG-CoA reductase inhibitors and the like.

The compound of the present invention or an isomer, N-oxide, solvate, crystalline or prodrug thereof can be mixed with a pharmaceutically acceptable carrier, diluent or excipient to prepare a pharmaceutical formulation, which is suitable for oral or parenteral administration. Methods of administration include, but are not limited to intradermal, intramuscular, intraperitoneal, intravenous, subcutaneous, intranasal, and oral routes. The formulations may be administered by any route, for example by infusion or bolus injection, or by absorption through epithelial or mucocutaneous linings (for example, oral mucosa or rectal mucosa, etc.). Administration can be systemic or local. Examples of the formulations for oral administration can be solid or liquid dosage forms, and include, in particular, tablets, pills, granules, powders, capsules, syrups, emulsions, suspensions, etc. The formulations may be prepared by methods known in the art and include diluents or excipients conventionally used in the field of pharmaceutical formulation.

In a fourth aspect, the present invention provides a method of treating or preventing tumor using the compound of the present invention or the isomer, N-oxide, solvate, crystal, or prodrug thereof, and their use in the manufacture of a medicament for preventing or treating tumors, comprising administering to a tumor-prone subject or tumor patient a compound of the present invention or the isomer, N-oxide, solvate, crystal or prodrug thereof, or the pharmaceutical composition comprising the compound of the present invention or the isomer, solvate, crystal or prodrug thereof, to effectively reduce tumor incidence and prolong the life of tumor patients.

DEFINITION OF TERMS

The term "alkyl" in the present invention refers to a straight-chain or branched-chain saturated hydrocarbon radical, preferably is $C_{1-6}$ alkyl, and more preferably is $C_{1-3}$ alkyl. A suitable $C_{1-3}$ alkyl is methyl, ethyl, propyl or isopropyl.

The term "alkoxy" in the present invention refers to an alkyl-O— group, preferably is $C_{1-6}$ alkyl-O— groups, and more preferably is $C_{1-3}$ alkyl-O— group. A suitable $C_{1-3}$ alkoxy is methoxy, ethoxy, propoxy, or isopropoxy.

The term "halogen" in the present invention refers to a fluoro, chloro, or bromo group, and preferably is fluoro, or chloro group.

The term "halo-substituted alkyl" in the present invention refers to an alkyl group substituted by at least one halogen, preferably is halo-substituted $C_{1-6}$ alkyl, and more preferably is halo-substituted $C_{1-3}$ alkyl. A suitable halo-substituted $C_{1-3}$ alkyl is chloromethyl, fluoromethyl, dichloromethyl, difluoromethyl, trichloromethyl, trifluoromethyl, chloroethyl, fluoroethyl, dichloroethyl, difluoroethyl, trichloroethyl, or trifluoroethyl.

The term "halo-substituted alkoxy" in the present invention refers to an alkoxy group substituted by at least one halogen, preferably is $C_{1-6}$ alkoxy substituted by at least one halogen, and more preferably is halo-substituted $C_{1-3}$ alkoxy. A suitable halo-substituted $C_{1-3}$ alkoxy is chloromethoxy, fluoromethoxy, dichloromethoxy, difluoromethoxy, trichloromethoxy, trifluoromethoxy, dichloroethoxy, difluoroethoxy, trichloroethoxy, or trifluoroethoxy.

The term "5-, 6-, 7- and 8-membered nitrogen-containing heterocyclic group" in the present invention refers to a substituted or unsubstituted heterocyclic groups that is saturated, partially saturated and fully unsaturated and has at least one ring and the total number of five, six, seven or eight ring atoms wherein at least one ring atom is nitrogen atom. Preferably, the "5-, 6-, 7- and 8-membered nitrogen-containing heterocyclic group" is piperazinyl, pyridinyl, azabicycloalkyl, imidazolyl, pyrazolyl, pyrrolyl, triazolyl, pyridazinyl, pyrimidinyl, pyrazinyl, piperidinyl, triazinyl, or substituted piperazinyl, pyridinyl, azabicycloalkyl, imidazolyl, pyrazolyl, pyrrolyl, triazolyl, pyridazinyl, pyrimidinyl, pyrazinyl, piperidinyl, or triazinyl, wherein the substituent(s) is(are) selected from alkyl, hydroxy, hydroxyalkyl, alkoxy, amino, mono-alkylamino, di-alkylamino, aminoacyl, alkylaminoacyl, arylaminoacyl, heteroarylaminoacyl, halogen, halo-substituted alkyl, and halo-substituted alkoxy, and preferably the substituent(s) is(are) selected from $C_{1-6}$ alkyl, hydroxy, hydroxy $C_{1-6}$ alkyl, $C_{1-6}$ alkoxy, amino, mono-$C_{1-6}$ alkylamino, bi-$C_{1-6}$ alkylamino, aminoacyl, $C_{1-6}$ alkylaminoacyl, arylaminoacyl, heteroarylaminoacyl, halogen, halo-substituted $C_{1-6}$ alkyl, and halo-substituted $C_{1-6}$ alkoxy.

The term "solvate" in the present invention in the conventional sense refers to a complex formed by coordination of a solute (e.g., an active compound or a salt of the active compound) with solvent (e.g., water). The solvent means a solvent known or readily determined by a person skilled in the art. When the solvent is water, the solvate is usually referred to as a hydrate, e.g., monohydrate, dihydrate or trihydrate.

The term "crystal" in the present invention refers to various solid forms of the compound of the present invention formed, including crystal forms and amorphous forms.

The term "isomer" in the present invention includes configurational isomers, conformational isomers and enantiomers of the compounds. A configurational isomer refers to a cis or trans-isomer having cis- or trans-form. A conformational isomer refers to a stereoisomer generated by rotation about single bond.

The term "prodrug" in the present invention refers to a compound which is converted into the compound of the present invention by reacting with enzymes, gastric acid and the like in the physiological condition in the living body, that is, a compound which is converted into the compound of the present invention via enzymatic oxidation, reduction, or hydrolysis, and/or a compound which is converted to the compound of the present invention via hydrolysis in gastric acid and the like.

The term "pharmaceutically acceptable salt" refers to a pharmaceutically acceptable salt formed by reaction of the compound of the present invention with an acid. Said acids include, but are not limited to, phosphoric acid, sulfuric acid, hydrochloric acid, hydrobromic acid, citric acid, maleic acid, malonic acid, mandelic acid, succinic acid, fumaric acid, acetic acid, lactic acid, nitric acid and the like.

The term "pharmaceutical composition" in the present invention refers to a mixture comprising any one of the compounds described herein comprising an isomer, N-oxide, prodrug, solvate, pharmaceutically acceptable salt or chemically protected form thereof and one or more pharmaceutically acceptable carriers and/or excipients. Also, said pharmaceutical composition includes a combination comprising the compound described herein comprising an isomer, N-oxide, prodrug, solvate, pharmaceutically acceptable salt or chemically protected form thereof and one or more other active agents.

The term "pharmaceutically acceptable carrier" in the present invention refers to a carrier which does not cause significant irritation to an organism and does not interfere with the biological activity and properties of the administered compound, including solvents, diluents or other excipients, dispersants, surfactants, isotonic agents, thickening agents, emulsifying agents, preservatives, solid binders, lubricants and the like, except for any conventional carrier medium which is incompatible with the compound of the present invention. Examples of the pharmaceutically acceptable carrier include, but are not limited to, saccharides such as lactose, glucose and sucrose; starches, such as corn starch and potato starch; cellulose and its derivatives such as sodium carboxymethyl cellulose as well as cellulose and cellulose acetate; malt, gelatin and the like.

The term "excipient" in the present invention refers to an inert substance which is added to the pharmaceutical composition of the present invention to further promote the administration of the compound. The excipients may include calcium carbonate, calcium phosphate, various sugars and various types of starch, cellulose derivatives, gelatin, vegetable oils and polyethylene glycols.

The expression "use in the manufacture of a medicament for treating or preventing tumors" in the present invention refers to inhibiting the growth, development and/or metastasis of cancers, mainly administering a therapeutically effective amount of the compound of the present invention to a human or animal in need thereof to inhibit, slow or reverse the growth, development or spread of the tumors in the subject.

The compound of the present invention refers to the compounds of all the general formulas according to the present invention, including the compounds of any one of general formula I, general formula Ia, general formula Ib, general formula Ic, general formula Id and general formula Ie according to the present invention, and the corresponding specific compounds.

DETAILED DESCRIPTION OF THE INVENTION

The following representative embodiments are meant to better illustrate the present invention, and are not intended to limit the scope of the invention.

Example 1

Preparation of N-[3-((1H-pyrazolo[3,4-b]pyridin-5-yl) ethynyl)-4-methylphenyl]-N'-[4-((4-methylpiperazin-1-yl)methyl)-3-trifluoromethylphenyl]urea

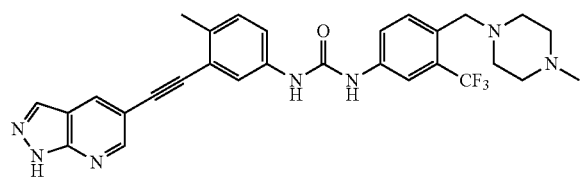 [SMILES: Cc1ccc(NC(=O)Nc2ccc(CN3CCN(C)CC3)c(C(F)(F)F)c2)cc1C#Cc1cnc2[nH]ncc2c1]

Step 1: Preparation of N-(3-iodo-4-methylphenyl)-N'-[4-((4-methylpiperazin-1-yl)methyl)-3-trifluoromethylphenyl]urea Triphosgene (1.04 g, 3.5 mmol) and ClCH$_2$CH$_2$Cl (20 ml) were added into a 100 ml round-bottomed flask, and stirred at room temperature until triphosgene was completely dissolved and the system appears colorless and transparent. The reaction system was placed in an ice-salt bath and stirred, 3-iodo-4-methylaniline (1.64 g, 7 mmol) in ClCH$_2$CH$_2$Cl solution (20 ml) was slowly added dropwise, and the system appears yellow milky. After the addition was complete, the mixture was stirred at room temperature for 4 hours. Et$_3$N (1.43 g, 14 mmol) was added and stirred at room temperature for 0.5 hour. 4-(4-methylpiperazin-1-ylmethyl)-3-trifluoromethylaniline (1.87 g, 7 mmol) was added and stirred at room temperature for 16 hours. The volatiles were removed by distillation under reduced pressure, and the residue was extracted with ethyl acetate (30 ml×3) and H$_2$O (30 ml). The organic phases were combined, dried over anhydrous Na$_2$SO$_4$, concentrated, and purified by column chromatography, to give a yellow solid.

ESI-MS m/z: [M+H]$^+$=533.2, calculated: 533.3.

Step 2: Preparation of N-[4-methyl-3-((trimethylsilyl)ethynyl)phenyl]-N'-[4-((4-methylpiperazin-1-yl)methyl)-3-trifluoromethylphenyl]urea The product (1.06 g, 2.0 mmol) obtained from Step 1, CuI (0.19 g, 0.1 mmol), Pd(PPh$_3$)Cl$_2$ (0.35 g, 0.5 mmol) and DMF (10 ml) were added into a 100 ml three-necked flask, and Et$_3$N (0.52 g, 4.0 mmol) and trimethylsilylacetylene (0.98 g, 10 mmol) were added under the protection of an inert gas atmosphere. The mixture was reacted at 80° C. for 16 hours with stirring, and the system was cooled to room temperature, filtered, and extracted with ethyl acetate (50 ml×3) and H$_2$O (50 ml). The organic phases were back-extracted with saturated brine, and the organic phases were combined, dried over anhydrous Na$_2$SO$_4$, and purified by column chromatography, to give a milky white solid.

ESI-MS m/z: [M+H]$^+$=503.5, calculated: 503.6.

Step 3: Preparation of N-(3-ethynyl-4-methylphenyl)-N'-(4-((4-methylpiperazin-1-yl)methyl)-3-trifluoromethylphenylurea The product (0.836 g, 1.7 mmol) obtained from Step 2, K$_2$CO$_3$ (0.704 g, 5.1 mmol) and MeOH (20 ml) were added into a 50 ml round-bottomed flask, and stirred at room temperature for 4 hours. The volatiles were distilled off under reduced pressure, and the residue was extracted with ethyl acetate (50 ml×3) and H$_2$O (50 ml). The organic phases were combined, dried over anhydrous Na$_2$SO$_4$, and concentrated, to give a yellow solid.

ESI-MS m/z: [M+H]$^+$=431.4, calculated: 431.4.

Step 4: Preparation of N-[3-41H-pyrazolo[3,4-b]pyridin-5-yl)ethynyl)-4-methylphenyl]-N'-[4-((4-methylpiperazin-1-yl)methyl)-3-trifluoromethylphenyl]urea The product (108 mg, 0.25 mmol) obtained from Step 3,5-bromo-1H-pyrazolo[3,4-b]pyridine (62 mg, 0.31 mmol), Pd(PPh$_3$)$_2$Cl$_2$ (1.4 mg, 0.02 mmol), tricyclohexylphosphine (10 mg, 0.04 mmol), Cs$_2$CO$_3$ (49 mg, 0.15 mmol) and DBU (6d) and DMF (5 ml) were added into a 50 ml sealed tube, and stirred at 80° C. for 48 hours under the protection of argon gas. The system was cooled to room temperature, filtered, and extracted with ethyl acetate (30 ml×3) and H$_2$O (30 ml). The organic phases were combined, dried over anhydrous Na$_2$SO$_4$, concentrated, and purified by column chromatography, to give the title compound as a white viscous matter.

$^1$H NMR (500 MHz, d$^6$-DMSO) δ: 12.29 (s, 1H, N—H), 9.85 (s, 1H, Ar—H), 9.64 (s, 1H, Ar—H), 8.52 (s, 1H, Ar—H), 7.98-7.96 (t, 2H, Ar—H), 7.79-7.78 (d, 1H, Ar—H), 7.60 (s, 2H, N—H), 7.41-7.39 (m, 1H, Ar—H), 7.26-7.25 (d, 1H, Ar—H), 6.67-6.66 (d, 1H, Ar—H), 3.34 (s, 2H, NCH$_2$), 2.45 (s, 3H, CH$_3$), 2.38-2.33 (m, 8H, NCH$_2$CH$_2$N), 2.16 (s, 3H, CH$_3$).

ESI-MS m/z: [M+H]$^+$=548.2, calculated: 548.2.

Example 2

Preparation of N-[3-((1H-pyrrolo[2,3-b]pyrazin-5-yl) ethynyl)-4-methylphenyl]-N'-[4-((4-methylpiperazin-1-yl)methyl)-3-trifluoromethylphenyl]urea

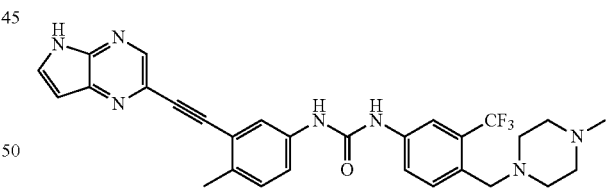

The title compound was prepared using 5-bromo-1H-pyrrolo[2,3-b]pyrazine and N-(3-ethynyl-4-methylphenyl)-N'-[4-((4-methylpiperazin-1-yl)methyl)-3-trifluoromethylphenyl]urea as raw materials, according to the method described in Step 4 of Example 1.

$^1$H NMR (500 MHz, CDCl$_3$) δ: 8.75 (s, 1H, N—H), 8.50 (s, 1H, Ar—H), 7.71 (s, 1H, Ar—H), 7.64 (s, 1H, Ar—H), 7.61-7.60 (d, 3H, Ar—H), 7.46 (s, 1H, Ar—H), 7.38-7.36 (d, 2H, Ar—H), 6.75-6.62 (s, 1H, N—H), 6.47 (s, 1H, N—H), 3.61 (s, 2H, NCH$_2$), 2.56-2.51 (m, 11H, CH$_3$, NCH$_2$CH$_2$N), 2.295 (s, 3H, CH$_3$).

ESI-MS m/z: [M+H]$^+$=548.2, calculated: 548.2.

Example 3

Preparation of 3-01H-pyrrolo[2,3-b]pyrazin-5-yl) ethynyl)-4-methyl-N-[4-((4-methylpiperazin-1-yl) methyl)-3-trifluoromethylphenyl]benzamide

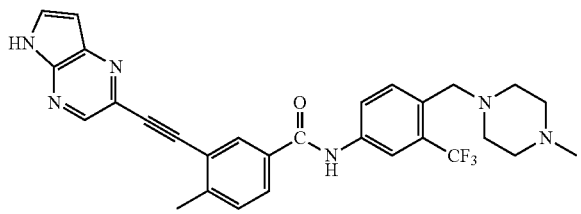 [SMILES: Cc1ccc(C(=O)Nc2ccc(CN3CCN(C)CC3)c(C(F)(F)F)c2)cc1C#Cc1cnc2[nH]ccc2n1]

Step 1: Preparation of 3-iodo-4-methyl-N-[4-(4-methylpiperazin-1-yl)methyl)-3-trifluoromethylphenyl]benzamide 4-(4-methylpiperazin-1-ylmethyl)-3-trifluoromethylaniline (2.27 g, 8.3 mmol), 3-iodo-4-methyl-benzoyl chloride (10 mmol), 15 ml tetrahydrofuran and 10 ml triethylamine were added into a reactor, and stirred for 4 hours at room temperature. The resultant was washed with saturated NaHCO$_3$ solution, extracted with ethyl acetate and water, washed with a saturated NaCl solution, and dried over anhydrous Na$_2$SO$_4$. The solvent was removed by distillation under reduced pressure. The residue was purified by silica gel column chromatography, to give a yellow oil matter.

$^1$H NMR (500 MHz, CDCl$_3$) δ: 8.39 (s, 1H, N—H), 8.29 (s, 1H, Ar—H), 7.88 (d, 1H, Ar—H), 7.86 (s, 1H, Ar—H), 7.75 (d, 1H, Ar—H), 7.73 (d, 1H, Ar—H), 7.28 (d, 1H, Ar—H), 3.62 (s, 2H, PhCH$_2$), 2.60 (b, 8H, 4×—CH$_2$), 2.47 (s, 3H, —CH$_3$), 2.31 (s, 3H, —CH$_3$).

Step 2: Preparation of 3-trimethylsilylethynyl-4-methyl-N-[4-((4-methylpiperazin-1-yl)methyl)-3-trifluoromethylphenyl]benzamide The product (3.1 g, 6.1 mmol) obtained from Step 1, Pd(PPh$_3$)$_2$Cl$_2$ (426 mg, 0.61 mmol) and CuI (231 mg, 1.21 mmol) were added into a reactor, and 1 ml triethylamine was added for maintaining an alkaline environment. Under the protection of an inert gas atmosphere, trimethylsilylacetylene (3.0 g, 30.3 mmol) was added into the mixture, and stirred at 58° C. for 24 hours. After completion of the reaction, the reaction mixture was extracted with ethyl acetate and water. The organic layers were combined, washed with a saturated NaCl solution, dried over anhydrous Na$_2$SO$_4$, and concentrated under reduced pressure. The residue was purified by silica gel column chromatography, to give a yellow solid.

$^1$H NMR (500 MHz, CDCl$_3$) δ: 8.30 (s, 1H, N—H), 7.86 (s, 1H, Ar—H), 7.83 (d, 1H, Ar—H), 7.72 (s, 1H, Ar—H), 7.55 (d, 1H, Ar—H), 7.41 (d, 1H, Ar—H), 7.24 (d, 1H, Ar—H), 3.60 (s, 2H, PhCH2), 2.48 (b, 8H, 4×—CH2), 2.45 (s, 3H, —CH3), 2.28 (s, 3H, —CH3), 0.26 (s, 9H, 3×—CH$_3$).

Step 3: Preparation of 3-ethynyl-4-methyl-N-[4-((4-methylpiperazin-1-yl)methyl)-3-trifluoromethylphenyl]benzamide The product (1.59 g, 3.3 mmol) obtained from Step 2, potassium carbonate (1.82 g, 13.2 mmol) and 20 ml methanol were mixed in a reactor, and stirred at room temperature under the protection of an inert gas atmosphere for 3 hours. After completion of the reaction, methanol was removed on a rotary evaporator and the mixture was extracted with ethyl acetate and water. The organic layers were combined, washed with a saturated NaCl solution, and dried over anhydrous Na$_2$SO$_4$. The organic solution was concentrated on a rotary evaporator, and the residue was purified by silica gel column chromatography, to give a yellow oily liquid.

$^1$H NMR (500 MHz, CDCl$_3$) δ: 10.47 (s, 1H, N—H), 8.19 (s, 1H, Ar—H), 8.08 (s, 1H, Ar—H), 8.04 (d, 1H, Ar—H), 7.91 (d, 1H, Ar—H), 7.70 (d, 1H, Ar—H), 7.47 (d, 1H, Ar—H), 4.50 (s, 1H, ≡CH), 3.56 (s, 2H, PhCH2), 2.50 (s, 3H, —CH$_3$), 2.36 (b, 8H, 4×CH$_2$), 2.15 (s, 3H, —CH$_3$).

Step 4: Preparation of 3-((1H-pyrrolo[2,3-b]pyrazin-5-yl)ethynyl)-4-methyl-N-[4-((4-methylpiperazin-1-yl)methyl)-3-trifluoromethylphenyl]benzamide The product (126 mg, 0.3 mmol) obtained from Step 3,5-bromo-1H-pyrrolo[2,3-b]pyrazine (59 mg, 0.3 mmol), Pd(PPh$_3$)$_2$Cl$_2$ (63 mg, 0.006 mmol), CuI (18 mg, 0.09 mmol), 1 ml Et$_3$N and 5 ml DMF were added into a 10 ml sealed tube, and reacted with stirring at 80° C. for 8 hours under the protection of an inert gas atmosphere. After completion of the reaction, the mixture was extracted with ethyl acetate and water. The organic layers were combined, washed with a saturated NaCl solution, dried over anhydrous Na$_2$SO$_4$, and concentrated under reduced pressure. The residue was purified by silica gel column chromatography, to give a white solid.

$^1$H NMR (500 MHz, CDCl$_3$) δ: 8.91 (br, 1H, —NH), 8.46 (s, 1H, Ar—H), 8.02 (d, 1H, Ar—H), 7.98 (s, 1H, Ar—H), 7.87 (s, 1H, Ar—H), 7.85 (s, —NH, 1H), 7.78-7.80 (m, 1H, Ar—H), 7.69-7.70 (d, 1H, Ar—H), 7.60-7.62 (m, 1H, Ar—H), 7.35 (d, 1H, Ar—H), 6.72-6.73 (m, 1H, Ar—H), 3.61 (s, 2H, —CH$_2$), 2.60 (s, 3H, —CH$_3$), 2.54 (b, 8H, —CH$_2$), 2.33 (s, 3H, —CH$_3$).

ESI-MS m/z: [M+H]$^+$=533.1, calculated: 533.2.

Example 4

Preparation of 3-((2-amino-[1,2,4]triazolo[1,5-a]pyridin-7-yl)ethynyl)-4-methyl-N-[4-((4-methylpiperazin-1-yl)methyl)-3-trifluoromethylphenyl]benzamide

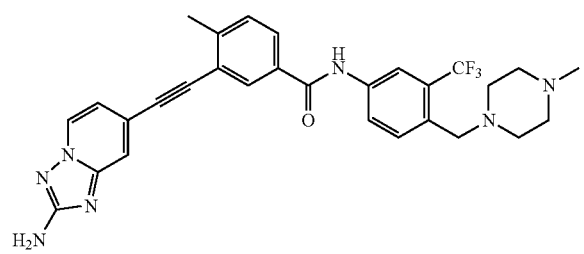 [SMILES: Cc1ccc(C(=O)Nc2ccc(CN3CCN(C)CC3)c(C(F)(F)F)c2)cc1C#Cc1ccn2nc(N)nc2c1]

The title compound was prepared using 2-amino-[1,2,4]triazolo[1,5-a]-7-bromopyridine and 3-ethynyl-4-methyl-N-[4-((4-methylpiperazin-1-yl)methyl)-3-trifluoromethylphenyl]benzamide as raw materials, according to the method described in Step 4 of Example 3.

$^1$HNMR (500 MHz, DMSO) δ: 10.52 (s, 1H, N—H), 8.59 (d, 1H, Ar—H), 8.20 (m, 2H, Ar—H), 8.06 (dd, 1H, Ar—H), 7.95 (dd, 1H, Ar—H), 7.71 (d, 1H, Ar—H), 7.60 (s, 1H,

Ar—H), 7.54 (d, 1H, Ar—H), 7.01 (d, 1H, Ar—H), 6.15 (s, 2H, —NH$_2$), 3.57 (s, 2H, —CH$_2$), 2.58 (s, 3H, —CH$_3$), 2.40 (b, 4H, —CH$_2$), 2.38 (b, 4H, —CH$_2$), 2.16 (s, 3H, —CH$_3$)
ESI-MS m/z: [M+H]$^+$=548.2, calculated: 548.2.

Example 5

Preparation of 3-((2-methylamino-[1,2,4]triazolo[1,5-a]pyridin-7-yl)ethynyl)-4-methyl-N-[4-((4-methylpiperazin-1-yl)methyl)-3-trifluoromethylphenyl]benzamide

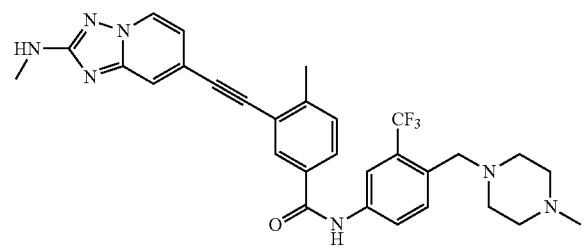

The title compound was prepared using 2-methylamino-[1,2,4]triazolo[1,5-a]-7-bromopyridine and 3-ethynyl-4-methyl-N-[4-((4-methylpiperazin-1-yl)methyl)-3-trifluoromethylphenyl]benzamide as raw materials, according to the method described in Step 4 of Example 3.
$^1$HNMR (300 MHz, DMSO) δ: 10.54 (s, 1H, N—H), 8.69 (d, 1H, Ar—H), 8.20 (s, 2H, Ar—H), 8.06 (d, 1H, Ar—H), 7.95 (d, 1H, Ar—H), 7.71 (d, 1H, Ar—H), 7.62 (s, 1H, N—H), 7.54 (d, 1H, Ar—H), 7.02 (d, 1H, Ar—H), 6.61 (d, 1H, Ar—H), 3.57 (s, 2H, —CH$_2$), 2.84 (d, 3H, —CH$_3$), 2.58 (s, 3H, —CH$_3$), 2.37 (m, 8H, —CH$_2$), 2.16 (s, 3H, —CH$_3$).
ESI-MS m/z: [M+H]$^+$=562.2, calculated: 562.2.

Example 6

Preparation of 3-((2-dimethylamino-[1,2,4]triazolo[1,5-a]pyridin-7-yl)ethynyl)-4-methyl-N-[4-((4-methylpiperazin-1-yl)methyl)-3-trifluoromethylphenyl]benzamide

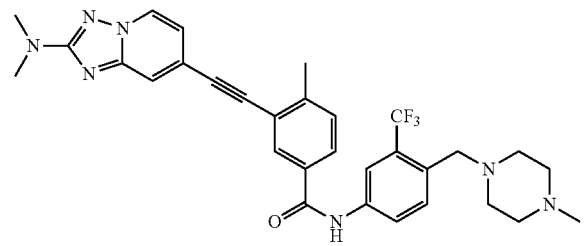

The title compound was prepared using 2-dimethylamino-[1,2,4]triazolo[1,5-a]-7-bromopyridine and 3-ethynyl-4-methyl-N-[4-((4-methylpiperazin-1-yl)methyl)-3-trifluoromethylphenyl]benzamide as raw materials, according to the method described in Step 4 of Example 3.
$^1$HNMR (300 MHz, DMSO) δ: 10.53 (s, 1H, N—H), 8.65 (d, 1H, Ar—H), 8.20 (s, 2H, Ar—H), 8.06 (d, 1H, Ar—H), 7.95 (d, 1H, Ar—H), 7.71 (d, 2H, Ar—H), 7.54 (d, 1H, Ar—H), 7.06 (d, 1H, Ar—H), 3.57 (s, 2H, —CH$_2$), 3.05 (s, 6H, —CH$_3$), 2.58 (s, 3H, —CH$_3$), 2.39 (m, 8H, —CH$_2$), 2.16 (s, 3H, —CH$_3$).
ESI-MS m/z: [M+H]$^+$=576.3, calculated: 576.2.

Example 7

Preparation of N-[2-methylamino-[1,2,4]triazolo[1,5-a]pyridin-7-yl)ethynyl)-4-methyl]phenyl-N'-[4-((4-methylpiperazin-t-yl)methyl)-3-trifluoromethylphenyl]urea

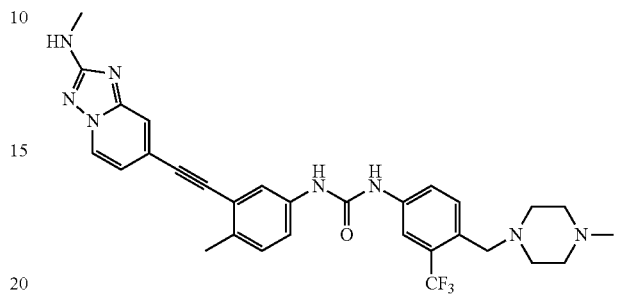

The title compound was prepared using 2-methylamino-[1,2,4]triazolo[1,5-a]-7-bromopyridine and N-(3-ethynyl-4-methylphenyl)-N'-(4-((4-methylpiperazin-1-yl)methyl)-3-trifluoromethylphenylurea as raw materials, according to the method described in Step 4 of Example 1.
$^1$H NMR (500 MHz, CDCl$_3$) δ: 8.61 (d, 1H, Ar—H), 8.51 (s, 1H, N—H), 8.02 (d, 1H, Ar—H), 7.70 (s, 1H, N—H), 7.68 (s, 1H, Ar—H), 7.62 (s, 1H, N—H), 7.55-7.66 (m, 4H, Ar—H), 7.46 (s, 1H, Ar—H), 7.17-7.19 (m, 1H, Ar—H), 3.61 (s, 2H, NCH$_2$), 2.85 (s, 3H, CH$_3$), 2.58 (s, 3H, CH$_3$), 2.55-2.53 (m, 8H, NCH$_2$CH$_2$N), 2.30 (s, 3H, CH$_3$).
ESI-MS m/z: [M+H]$^+$=577.2, calculated: 577.2.

Example 8

Preparation of N-[2-dimethylamino-[1,2,4]triazolo[1,5-a]pyridin-7-yl)ethynyl)-4-methyl]phenyl-N'-[4-((4-methylpiperazin-1-yl)methyl)-3-trifluoromethylphenyl]urea

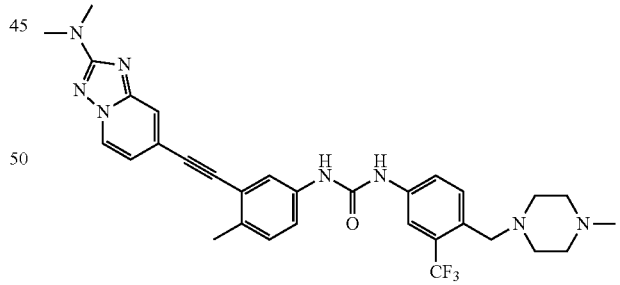

The title compound was prepared using 2-dimethylamino-[1,2,4]triazolo[1,5-a]-7-bromopyridine and N-(3-ethynyl-4-methylphenyl)-N'-(4-((4-methylpiperazin-1-yl)methyl)-3-trifluoromethylphenylurea as raw materials, according to the method described in Step 4 of Example 1.
$^1$H NMR (500 MHz, CDCl$_3$) δ: 8.60 (d, 1H, Ar—H), 8.51 (s, 1H, N—H), 8.02 (d, 1H, Ar—H), 7.68 (s, 1H, Ar—H), 7.62 (s, 1H, N—H), 7.53-7.65 (m, 4H, Ar—H), 7.46 (s, 1H, Ar—H), 7.17-7.19 (m, 1H, Ar—H), 3.61 (s, 2H, NCH$_2$), 3.05 (s, 6H, CH$_3$), 2.58 (s, 3H, CH$_3$), 2.56-2.51 (m, 8H, NCH$_2$CH$_2$N), 2.30 (s, 3H, CH$_3$).
ESI-MS m/z: [M+H]$^+$=591.2, calculated: 591.2.

Example 9

Preparation of 4-methyl-3-((1-methyl-5'-trifluoromethyl-1H,1'H-[2,2'-diimidazol]-4-yl)ethynyl)-N-[4-((4-methylpiperazin-1-yl)methyl)-3-trifluoromethylphenyl]benzamide

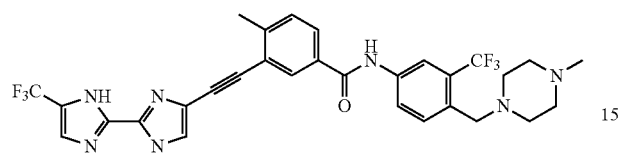

The title compound was prepared using 1-methyl-4-bromo-5'-trifluoromethyl-1H,1'H-2,2'-diimidazole and 3-ethynyl-4-methyl-N-[4-((4-methylpiperazin-1-yl)methyl)-3-trifluoromethylphenyl]benzamide as raw materials, according to the method described in Step 4 of Example 3.

$^1$H NMR (300 MHz, DMSO) δ: 10.54 (s, 1H, N—H), 8.16 (d, 2H, Ar—H), 8.05 (d, 1H, Ar—H), 7.96 (d, 1H, Ar—H), 7.70 (d, 1H, Ar—H), 7.56 (s, 1H, N—H), 7.51 (d, 1H, Ar—H), 7.02 (d, 1H, Ar—H), 6.74 (d, 1H, Ar—H), 4.13 (s, 2H, —CH$_2$), 3.57 (s, 3H, —CH$_3$), 2.55 (s, 3H, —CH$_3$), 2.47 (m, 8H, —CH$_2$), 2.24 (s, 3H, —CH$_3$).

ESI-MS m/z: [M+H]$^+$=630.2, calculated: 630.2.

Example 10

Preparation of 4-methyl-3-((1-methyl-1H,1'H-[2,2'-diimidazol]-4-yl)ethynyl)-N-[4-((4-methylpiperazin-1-yl)methyl)-3-trifluoromethylphenyl]benzamide

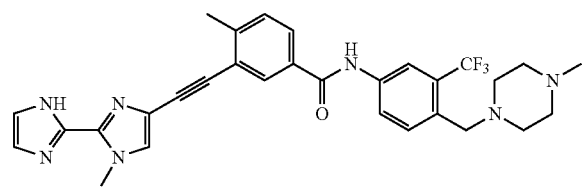 [SMILES: Cc1ccc(C(=O)Nc2ccc(CN3CCN(C)CC3)c(C(F)(F)F)c2)cc1C#Cc1cn(C)c(-c2ncc[nH]2)n1]

The title compound was prepared using 1-methyl-2-(1H-imidazol-2-yl)-4-bromoimidazole and 3-ethynyl-4-methyl-N-[4-((4-methylpiperazin-1-yl)methyl)-3-trifluoromethylphenyl]benzamide as raw materials, according to the method described in Step 4 of Example 3.

1HNMR (300 MHz, DMSO) δ: 12.92 (s, 1H, —NH), 10.54 (s, 1H, —NH), 8.28 (s, 1H, Ar—H), 8.16 (d, 1H, Ar—H), 8.05 (d, 1H, Ar—H), 7.96 (d, 1H, Ar—H), 7.70 (d, 1H, Ar—H), 7.51 (d, 1H, Ar—H), 6.98-7.05 (m, 3H, Ar—H), 4.13 (s, 2H, —CH$_2$), 3.56 (s, 3H, —CH$_3$), 2.56 (s, 3H, —CH$_3$), 2.47 (m, 8H, —CH$_2$), 2.26 (s, 3H, —CH$_3$).

ESI-MS m/z: [M+H]$^+$=562.2, calculated: 562.2.

Example 11

Preparation of 4-methyl-3-((1-methyl-5'-nitro-1H,1'H-[2,2'-diimidazol]-4-yl)ethynyl)-N-[4-((4-methylpiperazin-1-yl)methyl)-3-trifluoromethylphenyl]benzamide

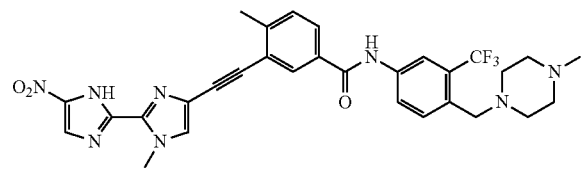 [SMILES: Cc1ccc(C(=O)Nc2ccc(CN3CCN(C)CC3)c(C(F)(F)F)c2)cc1C#Cc1cn(C)c(-c2ncc([N+](=O)[O-])[nH]2)n1]

The title compound was prepared using 1-methyl-2-(5-nitro-1H-imidazol-2-yl)-4-bromoimidazole and 3-ethynyl-4-methyl-N-[4-((4-methylpiperazin-1-yl)methyl)-3-trifluoromethylphenyl]benzamide as raw materials, according to the method described in Step 4 of Example 3.

$^1$HNMR (300 MHz, DMSO) δ: 13.02 (s, 1H, —NH), 10.52 (s, 1H, —NH), 8.26 (s, 1H, Ar—H) 8.16 (d, 1H, Ar—H), 8.10 (s, 1H, Ar—H), 8.05 (d, 1H, Ar—H), 7.96 (d, 1H, Ar—H), 7.70 (d, 1H, Ar—H), 7.51 (d, 1H, Ar—H), 7.02 (s, 1H, Ar—H), 4.13 (s, 2H, —CH$_2$), 3.56 (s, 3H, —CH$_3$), 2.56 (s, 3H, —CH$_3$), 2.47 (m, 8H, —CH$_2$), 2.26 (s, 3H, —CH$_3$)

ESI-MS m/z: [M+H]+=607.2, calculated: 607.2.

Example 12

Preparation of 4-methyl-3-((1-methyl-5'-methyl-1H,1'H-[2,2'-diimidazol]-4-yl)ethynyl)-N-[4-((4-hydroxyethylpiperazin-1-yl)methyl)-3-trifluoromethylphenyl]benzamide

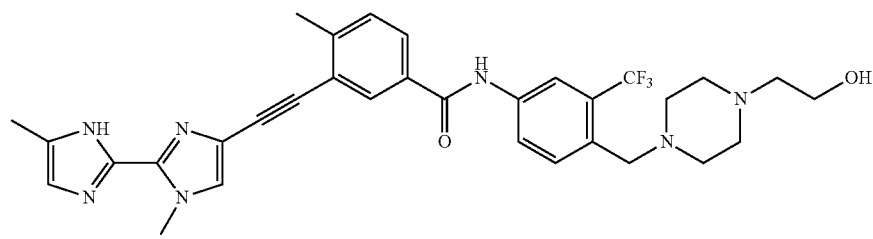 [SMILES: Cc1cnc(-c2nc(C#Cc3cc(C(=O)Nc4ccc(CN5CCN(CCO)CC5)c(C(F)(F)F)c4)ccc3C)cn2C)[nH]1]

The title compound was prepared using 4-(4-hydroxyethylpiperazin-1-ylmethyl)-3-trifluoromethylaniline, 3-iodo-4-methyl-benzoyl chloride, trimethylsilylacetylene and 1-methyl-2-(5-methyl-1H-imidazol-2-yl)-4-bromoimidazole as raw materials, according to the method described in Example 3.

1HNMR (300 MHz, DMSO) δ: 12.95 (s, 1H, —NH), 10.51 (s, 1H, —NH), 8.26 (s, 1H, Ar—H) 8.16 (d, 1H, Ar—H), 8.05 (d, 1H, Ar—H), 7.96 (d, 1H, Ar—H), 7.70 (d, 1H, Ar—H), 7.51 (d, 1H, Ar—H), 7.42 (d, 1H, Ar—H), 7.02 (s, 1H, Ar—H), 4.34 (s, 1H, —OH), 4.13 (s, 2H, —CH$_2$), 3.56 (s, 3H, —CH$_3$), 3.50 (s, 2H, —CH$_2$), 2.56 (s, 3H, —CH$_3$), 2.50 (b, 2H, —CH$_2$), 2.30-2.49 (m, 8H, —CH$_2$), 2.26 (s, 3H, —CH$_3$).

ESI-MS m/z: [M+H]$^+$=606.2, calculated: 606.2.

Example 13

Preparation of N-[4-methyl-3-((1-methyl-5'-trifluoromethyl-1H,1'H-[2,2'-diimidazol]-4-yl)ethynyl)phenyl]-N'—(R)-[4-((3-dimethylaminotetrahydropyrrol-1-yl)methyl)-3-fluorophenyl]urea

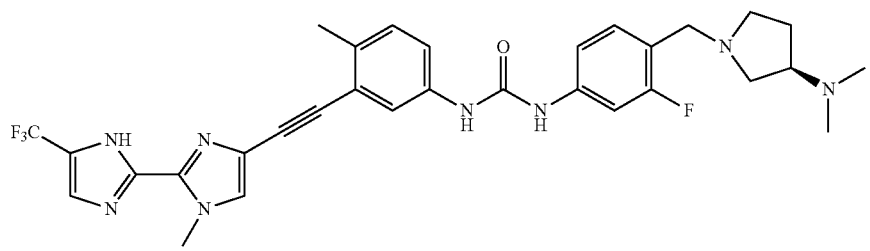 [SMILES: Cc1ccc(NC(=O)Nc2ccc(CN3CC[C@@H](N(C)C)C3)c(F)c2)cc1C#Cc1cn(C)c(-c2ncc(C(F)(F)F)[nH]2)n1]

The title compound was prepared using triphosgene, (R)-3-fluoro-4-(3-dimethylaminotetrahydropyrrol-1-yl)methylaniline, 3-iodo-4-methylaniline, trimethylsilylacetylene and 1-methyl-2-(5-trifluoromethyl-1H-imidazolyl)-4-bromoimidazole as raw materials, according to the method described in Example 1.

$^1$H NMR (500 MHz, CDCl$_3$) δ: 13.01 (s, 1H, —NH), 7.60-7.70 (m, 3H, Ar—H), 8.52 (s, 1H, N—H), 7.69 (s, 1H, N—H), 7.43 (d, 1H, Ar—H), 7.15-7.25 (m, 2H, Ar—H), 7.33 (s, 1H, Ar—H), 7.03 (s, 1H, Ar—H), 3.68 (s, 2H, —CH$_2$), 3.56 (s, 3H, CH$_3$), 2.69 (s, 3H, CH$_3$), 2.63-2.69 (m, 1H, —CH$_2$—), 2.55-2.62 (m, 1H, —CH$_2$—), 2.33-2.37 (m 1H, —CH), 2.16 (s, 6H, —CH$_3$), 1.93 (m, 2H, —CH$_2$—), 1.79 (m, 1H, —CH—), 1.68 (m, 1H, —CH—).

ESI-MS m/z: [M+H]+=609.2, calculated: 609.2.

Example 14

Preparation of N-[4-methyl-3-((1-methyl-5'-trifluoromethyl-1H,1'H-[2,2'-diimidazol]-4-yl)ethynyl)phenyl]-N'-[4-((4-methylpiperazin-1-yl)methyl)-3-trifluoromethylphenyl]urea

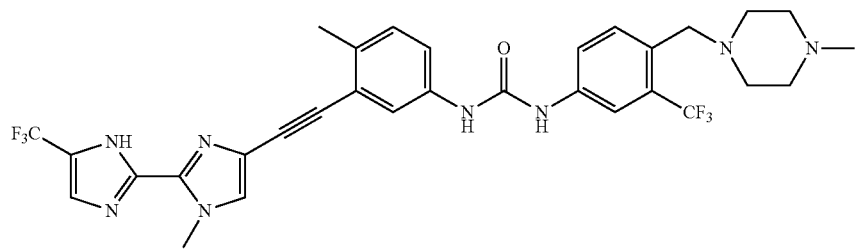 [SMILES: Cc1ccc(NC(=O)Nc2ccc(CN3CCN(C)CC3)c(C(F)(F)F)c2)cc1C#Cc1cn(C)c(-c2ncc(C(F)(F)F)[nH]2)n1]

The title compound was prepared using 1-methyl-2-(5-trifluoromethyl-1H-imidazol-2-yl)-4-bromoimidazole and N-(3-ethynyl-4-methylphenyl)-N'-(4-(4-methylpiperazin-1-yl)methyl)-3-trifluoromethylphenylurea as raw materials, according to the method described in Step 4 of Example 1.

¹H NMR (500 MHz, CDCl₃) δ: 12.93 (s, 1H, —NH), 8.61 (d, 1H, Ar—H), 8.52 (s, 1H, N—H), 8.02 (d, 1H, Ar—H), 7.70 (s, 1H, N—H), 7.66 (s, 1H, Ar—H), 7.62 (s, 1H, N—H), 7.56 (d, 1H, Ar—H), 7.46 (s, 1H, Ar—H), 7.35 (s, 1H, Ar—H), 7.17-7.19 (m, 1H, Ar—H), 7.03 (s, 1H, Ar—H), 3.61 (s, 2H, NCH₂), 3.58 (s, 3H, CH₃), 2.58 (s, 3H, CH₃), 2.52-2.56 (m, 8H, NCH₂CH₂N), 2.28 (s, 3H, CH₃)

ESI-MS m/z: [M+H]+=645.2, calculated: 645.2.

Example 15

Preparation of 3-trifluoromethyl-4-(4-hydroxyethylpiperazin-1-ylmethyl)-N-[3-(1-methyl-5'-trifluoromethyl-1H,1'H-[2,2'-diimidazol]-4-yl)ethynyl)-4-methylphenyl]benzamide

Example 16

Preparation of 3-[1-methyl-2-([1,2,4]-1H-triazol-3-yl)imidazol-5-yl]ethynyl-4-fluoro-N-[3-trifluoromethyl-5-(4-methylimidazol-1-yl)phenyl]benzamide

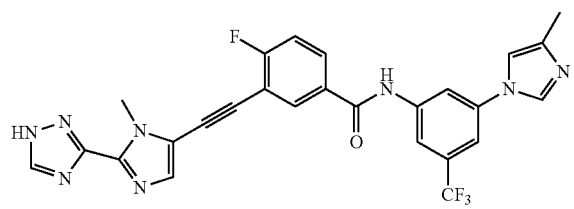

The title compound was prepared using 3-trifluoromethyl-5-(4-methylimidazol-1-yl)aniline, 3-iodo-4-fluorobenzoyl chloride, trimethylsilylacetylene and 1-methyl-2-([1,2,4]-

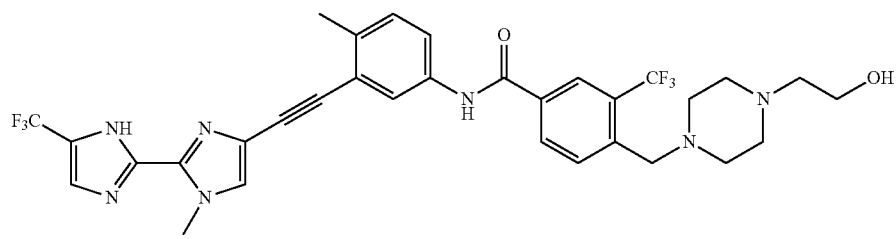 [SMILES: Cc1ccc(NC(=O)c2ccc(CN3CCN(CCO)CC3)c(C(F)(F)F)c2)cc1C#Cc1cn(C)c(-c2ncc(C(F)(F)F)[nH]2)n1]

The title compound was prepared using 3-iodo-4-methylaniline, 3-trifluoromethyl-4-(4-hydroxyethylpiperazin-1-yl)benzoyl chloride, trimethylsilyl acetyl ene and 1-methyl-2-(5-trifluoromethyl-1H-imidazol-2-yl)-4-bromoimidazole as raw materials, according to the method described in Example 3.

¹H NMR (500 MHz, CDCl₃) δ: 12.95 (s, 1H, —NH), 9.15 (s, 1H, —NH), 8.11 (d, 1H, Ar—H), 8.02 (d, 1H, Ar—H), 7.70 (s, 1H, Ar—H), 7.56 (s, 1H, Ar—H), 7.46 (s, 1H, Ar—H), 7.35 (s, 1H, Ar—H), 7.33 (s, 1H, Ar—H), 7.03 (s, 1H, Ar—H), 4.33 (s, 1H, OH), 3.61 (s, 2H, NCH₂), 3.58 (b, 2H, CH₂), 3.56 (s, 3H, CH₃), 3.51 (b, 2H, CH₂), 2.60 (s, 3H, CH₃), 2.33-2.53 (m, 8H, NCH₂CH₂N).

ESI-MS m/z: [M+H]+=660.2, calculated: 660.2.

1H-triazol-3-yl)-5-bromoimidazole as raw materials, according to the method described in Example 3.

1HNMR (500 MHz, DMSO-d6) δ: 13.18 (s, 1H, N—H), 9.18 (s, 1H, N—H), 8.40 (s, 1H, Ar—H), 8.33 (s, 1H, Ar—H), 8.25 (s, 1H, Ar—H), 7.89 (s, 1H, Ar—H), 7.78 (s, 1H, Ar—H), 7.69 (s, 1H, Ar—H), 7.45 (s, 1H, Ar—H), 7.32 (d, 2H, Ar—H), 7.28 (s, 1H, Ar—H), 3.52 (s, 3H, —CH₃), 2.24 (s, 3H, —CH₃).

ESI-MS [M+H]⁺=535.1, calculated: 535.1.

Example 17

Preparation of 4-fluoro-3-[1-methyl-2-([1,2,4]-1H-triazol-3-yl)imidazol-5-yl]ethynyl-N-[3-trifluoromethyl-5-(2-N-methylcarbamoylpyridin-4-yl)oxy]phenylbenzamide

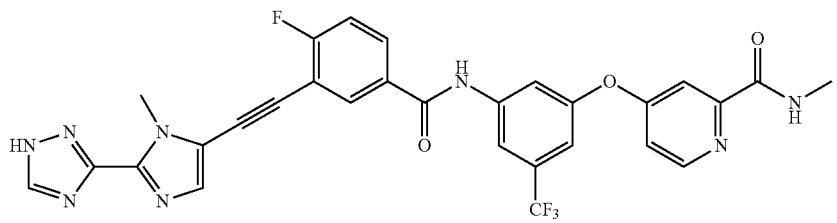 [SMILES: CNC(=O)c1cc(Oc2cc(NC(=O)c3ccc(F)c(C#Cc4cnc(-c5nc[nH]n5)n4C)c3)cc(C(F)(F)F)c2)ccn1]

The title compound was prepared using 3-trifluoromethyl-5-(2-(N-methylcarbamoylpyridin-4-yl)oxy)aniline, 3-iodo-4-fluorobenzoyl chloride, trimethylsilylacetylene and 1-methyl-2-([1,2,4]-1H-triazol-3-yl)-5-bromoimidazole as raw materials, according to the method described in Example ¹HNMR (500 MHz, DMSO-d6) δ: 12.92 (s, 1H, N—H), 9.18 (s, 1H, N—H), 8.55 (s, 1H, Ar—H), 8.35 (m, 1H, Ar—H), 8.23 (m, 1H, Ar—H), 8.05 (d, 2H, Ar—H), 7.85 (s, 1H, N—H), 7.67 (s, 1H, Ar—H), 7.40 (m, 1H, Ar—H), 7.35 (d, 2H, Ar—H), 7.28 (s, 1H, Ar—H), 0.714 (s, 1H, Ar—H), 3.69 (s, 3H, —CH₃), 2.86 (s, 3H, —CH₃).

ESI-MS m/z: [M+H]⁺=605.1, calculated: 605.1.

Example 18

Preparation of 4-methyl-3-((2-(5-trifluoromethyl-1H-imidazol-2-yl)pyridin-5-yl)ethynyl)-N-[4-((4-methylpiperazin-1-yl)methyl)-3-trifluoromethylphenyl]benzamide

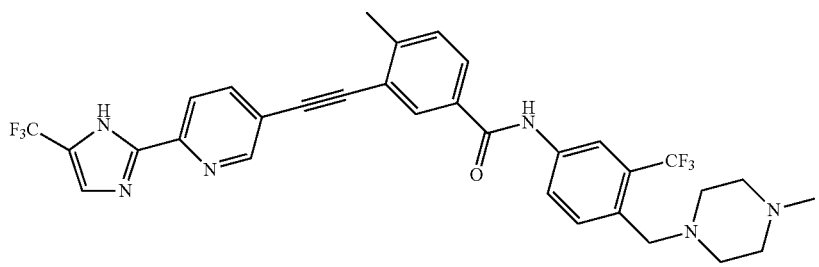 [SMILES: Cc1ccc(C(=O)Nc2ccc(CN3CCN(C)CC3)c(C(F)(F)F)c2)cc1C#Cc1ccc(-c2ncc(C(F)(F)F)[nH]2)nc1]

The title compound was prepared using 5-bromo-2-(5-trifluoromethyl-1H-imidazol-2-yl)pyridine and 3-ethynyl-4-methyl-N-[4-((4-methylpiperazin-1-yl)methyl)-3-trifluoromethylphenyl]benzamide as raw materials, according to the method described in Step 4 of Example 3.

¹HNMR (300 MHz, DMSO-d⁶) δ: 12.90 (s, 1H, N—H), 8.70 (s, 1H, —Ar—H), 8.06 (d, 1H, J=8.1 Hz, Ar—H), 8.05 (s, 1H, Ar—H), 8.04 (s, 1H, Ar—H), 7.95 (m, 2H, Ar—H), 7.84 (d, 1H, J=10.2, Ar—H), 7.80 (d, 1H, J=9.9 Hz, Ar—H), 7.66 (d, 1H, J=7.2 Hz, Ar—H), 7.60 (s, 1H, N—H), 7.37 (d, 1H, J=7.8 Hz, Ar—H), 3.57 (s, 2H, —CH₂), 2.52 (s, 3H, —CH₃), 2.60-2.30 (b, 8H, —CH₂), 2.24 (s, 3H, —CH₃).

ESI-MS m/z: [M+H]⁺=627.2, calculated: 627.2.

Example 19

Preparation of 4-methyl-3-((2-(1H-imidazol-2-yl)pyridin-5-yl)ethynyl)-N-[4-((4-methylpiperazin-1-yl)methyl)-3-trifluoromethylphenyl]benzamide

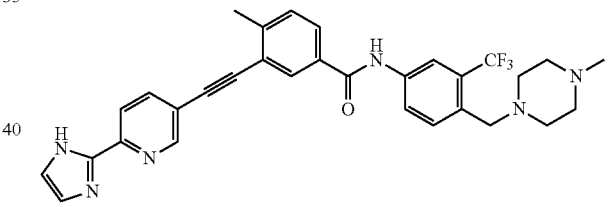

The title compound was prepared using 5-bromo-2-(1H-imidazol-2-yl)pyridine and 3-ethynyl-4-methyl-N-[4-((4-methylpiperazin-1-yl)methyl)-3-trifluoromethylphenyl]benzamide as raw materials, according to the method described in Step 4 of Example 3.

¹HNMR (500 MHz, DMSO-d₆) δ: 12.92 (s, 1H, —NH), 10.52 (s, 1H, —NH), 8.81 (s, 1H, Ar—H), 8.20 (s, 2H, Ar—H), 8.09 (s, 2H, Ar—H), 8.07 (d, 1H, J=8.4 Hz, Ar—H), 7.95 (q, 1H, $J_1$=8.0 Hz, $J_2$=1.8 Hz, Ar—H), 7.71 (d, 1H, J=8.4 Hz, Ar—H), 7.54 (d, 1H, J=8.2 Hz, Ar—H), 7.28 (s, 1H, Ar—H), 7.13 (s, 1H, Ar—H), 3.57 (s, 2H, —CH$_2$), 2.59 (s, 3H, —CH$_3$), 2.40 (b, 4H, —CH$_2$), 2.34 (b, 4H, —CH$_2$), 2.16 (s, 3H, CH$_3$).

ESI-MS m/z: [M+H]$^+$=559.1, calculated: 559.2.

Example 20

Preparation of 4-methyl-3-((2-(5-trifluoromethyl-1H-imidazol-2-yl)pyridin-5-yl)ethynyl)-N—[(R)-4-((3-dimethylaminotetrahydropyrrol-1-yl)methyl)-3-trifluoromethylphenyl]benzamide

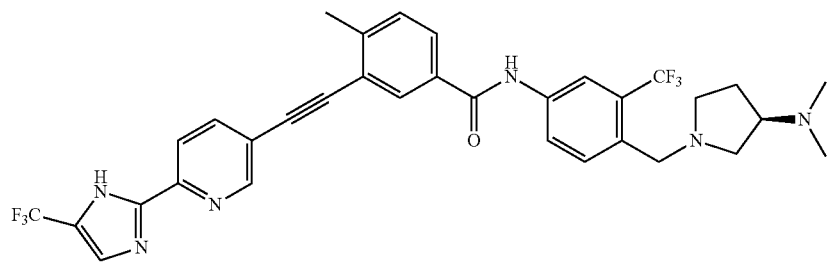 [SMILES: Cc1ccc(C(=O)Nc2ccc(CN3CC[C@@H](N(C)C)C3)c(C(F)(F)F)c2)cc1C#Cc1ccc(-c2ncc(C(F)(F)F)[nH]2)nc1]

The title compound was prepared using (R)-3-trifluoromethyl-4-(3-dimethylaminotetrahydropyrrol-1-yl)aniline, 3-iodo-4-methylbenzoyl chloride, trimethylsilylacetylene and 2-(5-trifluoromethyl-1H-pyrazol-2-yl)-5-bromopyridine as raw materials, according to the method described in Example 3.

$^1$HNMR (500 MHz, DMSO) δ: 10.66 (s, 1H, N—H), 8.92 (s, 1H, N—H), 8.21 (m, 2H, Ar—H), 8.10 (d, 1H, Ar—H), 8.09 (m, 2H, Ar—H), 8.07 (t, 1H, Ar—H), 7.98 (d, 1H, Ar—H), 7.81 (d, 1H, Ar—H), 7.71 (d, 1H, Ar—H), 7.58 (s, 1H, Ar—H), 3.69 (dd, 2H, —CH$_2$), 2.68 (s, 3H, —CH$_3$), 2.64-2.68 (m, 2H, —CH), 2.57-2.62 (m, 1H, —CH), 2.14 (s, 6H, —CH$_3$), 1.91 (m, 2H, —CH$_2$—), 1.77 (m, 1H, —CH$_2$—), 1.66 (m, 1H, —CH$_2$—).

ESI-MS m/z: [M+H]$^+$=641.2, calculated: 641.2.

Example 21

Preparation of 4-(4-methylpiperazin-1-ylmethyl)-N-[3-(2-(5-acetonitrile-1H-pyrrol-2-yl)pyridin-5-yl-ethynyl)-4-methyl]benzamide

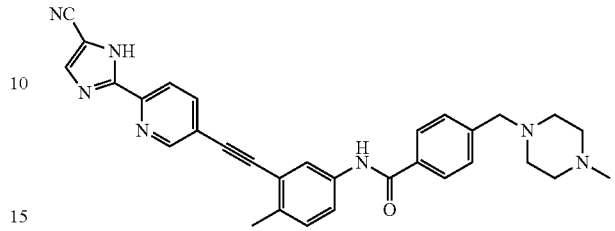

The title compound was prepared using 4-(4-methylpiperazin-1-ylmethyl)benzoyl chloride, 3-iodo-4-methylaniline, trimethylsilylacetylene and 2-(5-acetonitrile-1H-pyrrol-2-yl)-5-bromopyridine as raw materials, according to the method described in Example 3.

1HNMR (500 MHz, DMSO-d6) δ: 12.90 (s, 1H, —NH), 10.42 (s, 1H, —NH), 8.79 (s, 1H, Ar—H), 8.25 (s, 1H, Ar—H), 8.11 (s, 2H, Ar—H), 8.03 (d, 1H, J=8.4 Hz, Ar—H), 7.95 (q, 1H, $J_1$=8.4 Hz, $J_2$=1.8 Hz, Ar—H), 7.68 (d, 1H, J=8.4 Hz, Ar—H), 7.50 (d, 2H, J=8.2 Hz, Ar—H), 7.38 (s, 1H, Ar—H), 7.20 (s, 1H, Ar—H), 3.60 (s, 2H, —CH$_2$), 2.62 (s, 3H, Ar—CH$_3$), 2.45 (b, 4H, —CH$_2$), 2.40 (b, 4H, —CH$_2$), 2.14 (s, 1H, —CH$_3$).

ESI-MS m/z: [M+H]$^+$=516.2, calculated: 516.2.

Example 22

Preparation of 4-methyl-3-((2-(5-fluoro-1H-imidazol-2-yl)pyridin-5-yl)ethynyl)-N-[(S)-4-((3-dimethylaminotetrahydropyrrol-1-yl)methyl)-3-trifluoromethylphenyl]benzamide

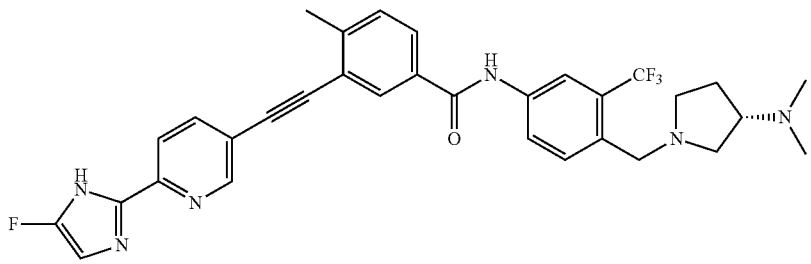 [SMILES: Cc1ccc(C(=O)Nc2ccc(CN3CC[C@H](N(C)C)C3)c(C(F)(F)F)c2)cc1C#Cc1ccc(-c2ncc(F)[nH]2)nc1]

The title compound was prepared using (S)-3-trifluoromethyl-4-(3-dimethylaminotetrahydropyrrol-1-yl)methylaniline, 3-iodo-4-methylbenzoyl chloride, trimethylsilylacetylene and 5-bromo-2-(5-fluoro-1H-imidazol-2-yl)pyridine as raw materials, according to the method described in Example 3.

¹HNMR (500 MHz, DMSO) δ: 10.86 (s, 1H, N—H), 8.76 (s, 1H, N—H), 8.19-8.22 (m, 2H, Ar—H), 8.10 (d, 1H, Ar—H), 8.06-8.09 (m, 2H, Ar—H), 8.07 (t, 1H, Ar—H), 7.99 (d, 1H, Ar—H), 7.82 (d, 1H, Ar—H), 7.71 (d, 1H, Ar—H), 7.36 (d, 1H, Ar—H), 3.67 (dd, 2H, —CH₂), 2.65 (s, 3H, —CH₃), 2.64-2.69 (m, 2H, —CH), 2.57-2.62 (m, 1H, —CH), 2.14 (s, 6H, —CH₃), 1.91 (m, 2H, —CH₂—), 1.77 (m, 1H, —CH₂—), 1.66 (m, 1H, —CH₂—).

ESI-MS m/z: [M+H]⁺=591.2, calculated: 591.2.

Example 23

Preparation of N-[3-(2-(5-acetonitrile-1H-imidazol-2-yl)pyridin-5-yl)ethynyl-4-methylphenyl]-N'-[3-trifluoromethyl-4-(4-methylpiperazin-1-ylmethyl)phenyl]urea

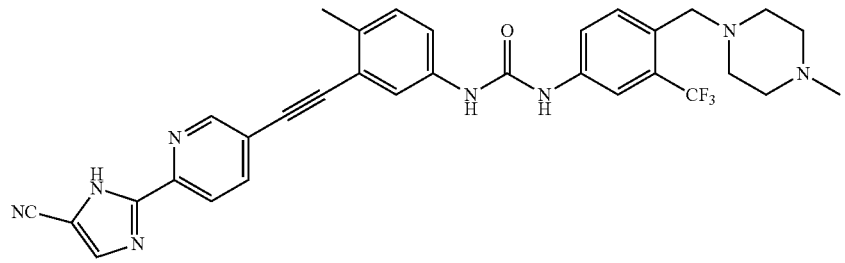 [SMILES: Cc1ccc(NC(=O)Nc2ccc(CN3CCN(C)CC3)c(C(F)(F)F)c2)cc1C#Cc1ccc(-c2ncc(C#N)[nH]2)nc1]

The title compound was prepared using N-[3-ethynyl-4-methylphenyl]-N'-[3-trifluoromethyl-4-(4-methylpiperazin-1-ylmethyl)phenyl]urea and 2-(5-acetonitrile-1H-imidazol-2-yl)-5-bromopyridine as raw materials, according to the method described in Step 4 of Example 1.

¹HNMR (500 MHz, DMSO-d6) δ: 12.90 (s, 1H, —NH), 10.42 (s, 1H, —NH), 8.79 (s, 1H, Ar—H), 8.25 (s, 1H, Ar—H), 8.11 (s, 2H, Ar—H), 8.03 (d, 1H, J=8.4 Hz, Ar—H), 7.95 (q, 1H, J₁=8.4 Hz, J₂=1.8 Hz, Ar—H), 7.68 (d, 1H, J=8.4 Hz, Ar—H), 7.50 (d, 2H, J=8.2 Hz, Ar—H), 7.38 (s, 1H, —NH), 7.20 (s, 1H, Ar—H), 3.60 (s, 2H, —CH₂), 2.62 (s, 3H, Ar—CH₃), 2.45 (b, 4H, —CH₂), 2.40 (b, 4H, —CH₂), 2.14 (s, 1H, —CH₃).

ESI-MS m/z: [M+H]⁺=599.1, calculated: 599.2.

Example 24

Preparation of 3-trifluoromethyl-5-(4-methylimidazol-1-yl)-N-[3-(2-(5-trifluoromethyl-1H-imidazol-2-yl)pyridin-5-yl)ethynyl-4-fluorophenyl]-benzamide

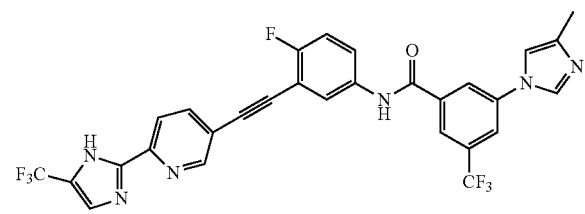 [SMILES: Cc1cn(-c2cc(C(=O)Nc3ccc(F)c(C#Cc4ccc(-c5ncc(C(F)(F)F)[nH]5)nc4)c3)cc(C(F)(F)F)c2)cn1]

The title compound was prepared using 3-trifluoromethyl-5-(4-methylimidazol-1-yl)benzoyl chloride, 3-iodo-4-fluoroaniline, trimethylsilylacetylene and 2-(5-trifluoromethylimidazol-2-yl)-5-bromopyridine as raw materials, according to the method described in Example 3.

¹HNMR (500 MHz, DMSO-d6) δ: 12.87 (s, 1H, N—H), 9.28 (s, 1H, Ar—H), 9.04 (s, 1H, N—H), 8.52 (s, 1H, Ar—H), 8.33 (s, 1H, Ar—H), 8.25 (s, 1H, Ar—H), 8.12 (d, 1H, Ar—H), 8.02 (d, 1H, Ar—H), 7.75 (s, 1H, Ar—H), 7.69 (s, 1H, Ar—H), 7.57 (s, 1H, Ar—H), 7.45 (s, 1H, Ar—H), 7.32 (d, 2H, Ar—H), 2.22 (s, 3H, —CH₃).

ESI-MS m/z: [M+H]⁺=599.0, calculated: 599.1.

Example 25

Preparation of 4-methyl-3-((2-(1,2,4-triazol-3-yl)pyridin-5-yl)ethynyl)-N-[4-((4-methylpiperazin-1-yl)methyl)-3-trifluoromethylphenyl]benzamide

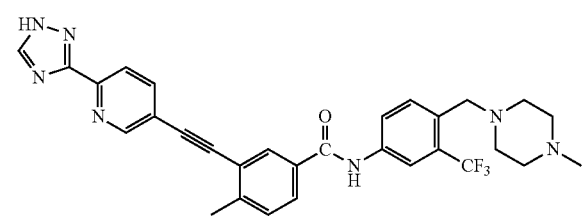 [SMILES: Cc1ccc(C(=O)Nc2ccc(CN3CCN(C)CC3)c(C(F)(F)F)c2)cc1C#Cc1ccc(-c2nc[nH]n2)nc1]

The title compound was prepared using 5-bromo-2-(1,2,4-triazol-3-yl)pyridine and 3-ethynyl-4-methyl-N-[4-((4-methylpiperazin-1-yl)methyl)-3-trifluoromethylphenyl]benzamide as raw materials, according to the method described in Step 4 of Example 3.

$^1$HNMR (500 MHz, DMSO) δ: 10.54 (s, 1H, N—H), 8.96 (s, 1H, N—H), 8.22 (t, 3H, Ar—H), 8.09 (m, 2H, Ar—H), 7.97 (d, 2H, Ar—H), 7.71 (d, 2H, Ar—H), 7.55 (d, 1H, Ar—H), 4.30 (s, 2H, —CH$_2$), 2.60 (s, 3H, —CH$_3$), 2.38 (m, 8H, —CH$_2$), 2.18 (s, 3H, —CH$_3$).

ESI-MS m/z: [M+H]$^+$=560.2, calculated: 560.2.

Example 26

4-methyl-3-[2-([1,2,4]-1H-triazol-3-yl)pyridin-5-yl]ethynyl-N-[(2-N-methylcarbamoylpyridin-4-yl)oxy]phenylbenzamide

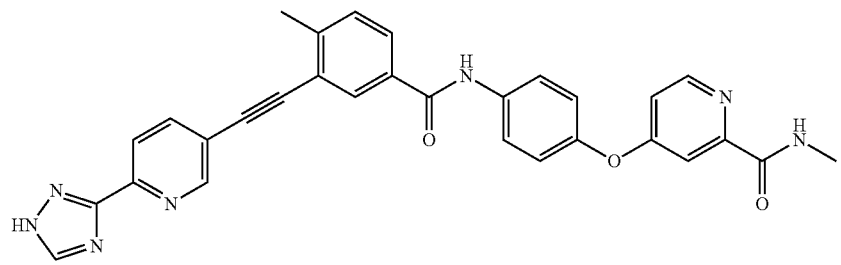 [SMILES: CNC(=O)c1cc(Oc2ccc(NC(=O)c3ccc(C)c(C#Cc4ccc(-c5nc[nH]n5)nc4)c3)cc2)ccn1]

The title compound was prepared using 4-(2-N-methylcarbamoylpyridin-4-yl)oxy]aniline, 3-iodo-4-methylbenzoyl chloride, trimethylsilylacetylene and 2-([1,2,4]-1H-triazol-3-yl)-5-bromopyridine as raw materials, according to the method described in Example 3.

$^1$HNMR (500 MHz, DMSO) δ: 10.45 (s, 1H, N—H), 8.76 (s, 1H, N—H), 8.21-8.22 (m, 3H, Ar—H), 7.95 (d, 1H, Ar—H), 7.85-7.933 (m, 3H, Ar—H), 7.87 (s, 1H, Ar—H), 7.69 (d, 11-1, Ar—H), 7.54 (d, 1H, N—H), 7.41 (d, 1H, Ar—H), 7.33-7.35 (m, 2H, Ar—H), 7.24 (d, 2H, Ar—H), 2.79 (s, 3H, —CH$_3$), 2.61 (s, 3H, —CH$_3$).

ESI-MS m/z: [M+H]$^+$=530.2, calculated: 530.2.

Example 27

3-((1H-pyrrolo[2,3-b]pyrazin-5-yl)ethynyl)-4-methyl-N-[4-((4-methylpiperazin-1-yl)methyl)-3-trifluoromethylphenyl]benzamide hydrochloride The compound (3-((1H-pyrrolo[2,3-b]pyrazin-5-yl)ethynyl)-4-methyl-N-[4-((4-methylpiperazin-1-yl)methyl)-3-trifluoromethylphenyl]benzamide) (30 mg) prepared in Example 3 was weighed, dissolved in 5 ml methanol, and a solution of hydrogen chloride in ethyl acetate was added dropwise to a pH of about 3. The mixture was stirred at room temperature for 3 hours. The volatiles were evaporated under reduced pressure, and the residue was dried under vacuum at 50° C. for 5 hours, to give the title compound.

$^1$H NMR (300 MHz, DMSO-d$_6$) δ: 12.34 (s, 1H), 10.61 (s, 1H), 10.25 (b, 1H), 8.56 (s, 1H), 8.26 (s, 2H), 8.14 (d, 1H), 7.96-8.01 (m, 2H), 7.73 (d, 1H), 7.56 (d, 1H), 6.67-6.69 (m, 1H), 3.70 (s, 2H), 3.37 (m, 4H), 2.89-3.06 (m, 4H), 2.77 (s, 3H), 2.61 (s, 3H).

$^1$H NMR (300 MHz, DMSO-d$_6$+D$_2$O) δ: 10.62 (s, 1H), 8.57 (s, 1H), 8.22 (s, 2H), 8.07 (d, 1H), 7.93-7.99 (m, 2H), 7.74 (d, 1H), 7.56 (d, 1H), 6.71 (d, 1H), 3.70 (s, 2H), 3.38-3.42 (m, 2H), 2.91-3.06 (m, 4H), 2.81 (s, 3H), 2.61 (s, 3H), 2.42 (m, 2H).

Experimental Example 1

In Vitro Evaluation of Cell Viability by the Compounds

In this example, MTT assay was used to detect in vitro inhibitory activity of the compounds prepared according to the above examples on the cells. Imatinib and AP24534 were used as controls. Imatinib was prepared according to the method described in CN1043531C and identified by 1H-NMR and MS. AP24534 was provided by Shanghai Xinkuo Chemical Technology Co., Ltd., China.

The used cells included K562 leukemia cells, Saos-2 human osteosarcoma cells, Ovcar-3 human ovarian cancer cells and MDA-MB-231 human breast cancer cells, which were all purchased from Nanjing KeyGen Biotech. Co., Ltd.

Experimental principle: the detection principle is that succinate dehydrogenase in mitochondria of living cells is capable of reducing exogenous MTT to water-insoluble blue-violet crystals formazan which deposits in cells, whereas dead cells do not have the function. Dimethyl sulfoxide (DMSO) is capable of dissolving formazan in cells, and absorbance value can be measured at a wavelength of 490 nm by an enzyme-linked immunometric meter, which reflects the number of living cells. Within a certain range of the number of cells, the amount of MTT crystals formed is proportional to the number of living cells.

Experimental Method:

1. Collecting the cells in logarithmic phase, adjusting the concentration of the cell suspension to about 1×10$^5$ cells/ml, and seeding into 96-well plates with 100 μl per well.

2. Culturing in a 37° C., 5% CO$_2$ incubator and keeping the cells adhering to the walls of the wells.

3. Adding different concentrations of drug (the drug has been subjected to suitable treatment, such as solubility, sterilization, etc.), and maintaining for an appropriate time period according to the experimental need, typically 48 hours.

4. Carefully removing the supernatant, gently washing with PBS and discarding the supernatant again.

5. Adding 180 μl fresh RPMI 1640 medium into each well, adding 20 μl MTT solution (5 mg/ml, that is, 0.5% MTT), and culturing for another 4 hours.

6. Terminating culturing and carefully discarding the medium in each well. 7. Adding 150 μl dimethyl sulfoxide into each well, shaking for 10 minutes at low speed in a shaker, to make crystals fully dissolved.

8. Measuring the absorbance of each well at 490 nm by an enzyme-linked immunometric meter.

9. Calculating inhibition rate at each concentration of the compound and the concentration inhibiting 50%, i.e., IC$_{50}$ values, according to the formula: Inhibition rate=1−(Absorbance value of sample well−Absorbance value of blank control well)/(Absorbance value of negative control well−Absorbance value of blank control well). The experimental results were shown in Table 1.

TABLE 1

| Tested compounds | Cell strains IC$_{50}$ (uM) | | | |
|---|---|---|---|---|
| | K562 Chronic myelogenous leukemia cells | Saos-2 Human osteosarcoma cells | Ovcar-3 Human ovarian cancer cells | MDA-MB-231 Human breast cancer cells |
| Example 1 | 4.13 | — | — | 2.79 |
| Example 2 | 2.06 | 0.27 | 3.09 | 0.11 |
| Example 3 | 6.33 | 0.38 | 2.85 | 0.18 |
| Example 4 | 13.51 | — | — | 1.06 |
| Example 5 | 6.79 | — | — | 2.15 |
| Example 6 | 4.16 | — | — | — |
| Example 7 | 5.07 | — | — | — |
| Example 8 | 0.42 | — | — | — |
| Example 9 | 0.33 | 1.16 | 6.50 | 5.08 |
| Example 10 | 1.92 | 0.87 | 3.19 | 1.42 |
| Example 11 | 3.14 | 2.68 | 10.05 | 0.36 |
| Example 12 | 2.31 | 5.73 | 4.06 | 1.27 |
| Example 13 | 0.52 | — | — | 0.29 |
| Example 14 | 0.16 | — | — | 1.21 |
| Example 15 | 0.37 | — | — | 0.56 |
| Example 16 | — | 1.16 | 4.72 | 1.27 |
| Example 17 | — | 0.64 | 3.98 | 0.98 |
| Example 18 | 1.43 | — | — | — |
| Example 19 | 4.52 | — | — | 3.01 |
| Example 20 | 2.21 | — | — | 4.72 |
| Example 21 | 3.59 | — | — | 2.06 |
| Example 22 | 4.07 | — | — | 1.15 |
| Example 23 | 3.31 | — | — | — |
| Example 24 | 0.94 | — | — | 1.17 |
| Example 25 | 3.58 | — | — | 2.86 |
| Example 26 | 5.91 | — | — | — |
| AP24534 | 4.80 | 0.38 | 1.21 | 0.42 |
| Imatinib | 8.42 | — | — | — |

"—" means undetected

Experimental Example 2

Evaluation of ABL1 (T315I) Kinase Activity by Some Compounds

In the experimental example, the compounds prepared according the examples of the present invention were tested for the ability to inhibit ABL (T315I) kinase activity. Imatinib was used as control.

A commercially available human ABL T315I mutant enzyme (Human ABL1 (T315I), active, catalog number #14-522, Millipore Corporation, USA) was used to test ABL (T315I) tyrosine kinase activity. Kinase activity was determined according to the manufacturer's instructions. Peptide substrate is Abltide (EAIYAAPFAKKK), purchased from Millipore Corporation, USA. Ion exchange chromatography paper P81 (ion exchange filter paper) was purchased from Whatman Company, UK. [γ-33P] ATP was purchased from Perkin Elmer Company.

Experimental protocol: Serially diluting the compound of the present invention from 1 μM initial concentration in three-fold fashion and formulating 10 concentrations (50.8 pM, 152.0 pM, 457.0 pM, 1.37 nM, 4.12 nM, 12.3 nM, 37.0 nM, 111.0 nM, 333.0 nM and 1.0 μM). 5.0 μM Abltide was added into each well and then human T315I mutant enzyme was added. [γ-33P] ATP was added at room temperature, with final concentration of 1.0 μM, and the reaction was performed for 120 minutes. 20 μl aliquots were transferred onto the ion exchange chromatography paper P81. The paper was thoroughly washed with a 0.75% phosphoric acid solution three times, and then washed with acetone once. Finally, γ-33P radioactivity was measured. The results were shown in Table 2 below.

TABLE 2

| Compound Numbers | IC$_{50}$ (nM) |
|---|---|
| Example 3 | 2.12 |
| Example 5 | 2.28 |
| Example 6 | 39.4 |
| Example 9 | 6.45 |
| Example 18 | 57.9 |
| Example 19 | 6.81 |
| AP24534 | 1.00 |
| Imatinib | >1000 |

As shown by the above experimental results, the compounds of the present invention have IC$_{50}$ values for inhibiting T315I mutant enzyme significantly better than Imatinib, and are comparable in magnitude with AP24534. The compounds of the present invention have powerful inhibitory effect on T315I mutant enzymes.

Experimental Example 3

In Vitro Evaluation of Bcr-Abl-Positive Cell Activity by Some Compounds 1.1 Compounds The compounds prepared in Example 3, Example 4 and Example 5 were illustratively selected for this experiment. The compounds of the present invention and imatinib were respectively dissolved in DMSO to 10 mM, diluted to 50 μM with complete medium, and then diluted to 10 μM with 0.1% DMSO in complete medium. The resulting solutions were 10-fold serially diluted and formulated into 10 concentrations. Imatinib was used as positive control.

1.2 Cells

MEG-01 human megakaryocyte leukemia cells and KU812 human peripheral blood basophilic leukocytes, purchased from ATCC Company, USA.

1.3 Reagents

Dimethyl sulfoxide (DMSO), purchased from Sigma Company, USA;

Luminescent cell viability assay kit (CellTiter-Glo®), purchased from Promega Corporation, USA;

Cell Titer-Glo® Substrate and Cell Titer-Glo® Buffer, purchased from Promega Corporation, USA;

IMEM medium, purchased from Gibco Company, USA;

RPMI 1640 medium, purchased from Gibco Company, USA;

Penicillin/streptomycin (Pen/Strep), purchased from Gibco Company, USA;

Fetal bovine serum (FBS), purchased from Gibco Company, USA;

0.25% trypsin-EDTA, purchased from Gibco Company, USA;

10 cm cell culture dish, purchased from Corning Corporation, USA;

50 ml centrifuge tube, purchased from Corning Corporation, USA;

384 Well Flat Clear Bottom White, purchased from Corning Corporation, USA;

Phosphate buffer saline (PBS), weekly prepared.

1.4 Instrument

PHERAstar Plus microplate reader, purchased from BMG Labtech Company, Germany.

2. Experimental Methods:

3.3 Cell Viability Assay Protocol

1) Collecting the cells in logarithmic phase, adjusting the concentration of the cell suspension to about 1×10$^5$ cells/ml, and seeding into 384-well plates with 40 μl per well, i.e., 4×10$^3$ cells/well. The peripheral wells were filled with sterile PBS;

2) Adding 10 µl of 5× concentration gradient of the tested compound, and adding 10 µl medium containing 0.5% DMSO into the blank control wells, in which the concentration of DMSO was 0.1%;

3) Incubating the cells in a 37° C./5% $CO_2$ incubator;

4) Adding 30 µl Cell Titer-Glo® Reagent 72 hours after adding the compound;

5) Incubating in a 37° C./5% $CO_2$ incubator for 10 minutes; and centrifuging at low speed and then measuring chemiluminescence values on a PHERAstar microplate reader.

6) Calculating cell viability (Cell Viability=($RLU_{sample}$/$RLU_{negative}$)×100%, wherein $RLU_{sample}$ was RLU (Relative Light Units) value of the well added with the compound and $RLU_{negative}$ was RLU value of the well without the compound (i.e., cell control, which was treated with the same concentration of DMSO)). Data were processed by using a four-parameter logistic fitting module in Graphpad Prism 4.0 software to calculate $IC_{50}$. $IC_{50}$ value represents the concentration of a compound inhibiting 50% of the cell growth, compared with the control group without adding the compounds. The experimental results were shown in Table 3 below.

TABLE 3

| Compounds | Cell strains $IC_{50}$ (nM) | |
|---|---|---|
| | MEG-01 | KU812 |
| Example 3 | 1.38 | 0.395 |
| Example 4 | 3.28 | 0.789 |
| Example 5 | 1.76 | 0.633 |
| Imatinib | 176 | 65.00 |

According to the above data, it can be seen that the compounds of the present invention have an activity on Bcr-Abl positive cell stains much better than Imatinib, and have stronger inhibitory effect.

From the above experimental results, it is concluded that the compounds of the present invention exhibit excellent effect on unmutated leukemia cells, especially have strong inhibition on Bcr-Abl positive cells, and meanwhile significantly inhibit the T315I mutant enzyme. Therefore, the compounds of the present invention are broad-spectrum Bcr-Abl inhibitors.

Experimental Example 4

Pharmacokinetic Studies

1. Materials
1.1 Compounds

The compound prepared in Example 27 of the present invention was illustratively selected for this experiment. The pharmaceutical formulation for oral administration was made by dissolving the compound in physiological saline to prepare 3 mg/ml of suspension. The pharmaceutical formulation for caudal vein injection was made by using a mixed solution of DMSO, polyoxyethylene castor oil and physiological saline in the volume ratio of 1:30:69 to prepare 2.5 mg/ml of solution.

1.2 Animals

Male SD rats, each group of three, weighing 150 g-250 g, were provided by Shanghai SIPPR-BK Laboratory Animal Co. Ltd., China. The tested rats were acclimatized to the environment for 2-4 days prior to the experiment, and fasted for 8-12 hours before administration. The rats drank water freely 2 hours after administration, and were fed food 4 hours after administration.

1.3 Reagents

Methanol (HPLC grade): Spectrum Company;
Acetonitrile (HPLC grade): Spectrum Company;
Other reagents were of analytical grade commercially available.

1.4 Instruments

AB Sciex API 4000 Triple Quad Mass Spectrometer, equipped with electrospray ionization Source (ESI), LC-20AD dual pumps; SIL-20AC Autosampler; CTO-20AC column oven; DGU-20A3R degasser; Analyst QS A01.01 chromatography workstation; Milli-Q Water Purification Systems (Millipore Inc.); Qilinbeier Vortex-5 oscillator; HITACHI CF16R XII Tabletop high-speed refrigerated centrifuge.

2. Experimental Methods

1) Taking blank plasma (zero-hour sample) after the SD rats were fasted but allowed drinking water freely for 12 hours;

2) Administering to three rats in Step 1) the compound prepared in Example 27 at 15 mg/kg by gavage (Intragastric administration, IG);

administering to another three rats in Step 1) the compound prepared in Example 27 at 3 mg/kg by caudal vein (Intravenous administration, IV);

3) Collecting sequentially blood from retinal venous plexus of the rats at 10 min, 30 min, 1 h, 2 h, 4 h, 6 h, 8 h, 10 h, 24 h after gavage administration, placing into the heparin-coated EP tubes, taking the upper plasma after centrifuging for 5 min at 8000 rpm/min, and storing at −20° C. until LC-MS/MS analysis;

4) Calculating the pharmacokinetic parameters using WinNonlin software according to the blood concentration—time data obtained from Step 3), shown in Table 4;

5) Collecting sequentially blood from retinal venous plexus of the rats at 5 min, 15 min, 30 min, 1 h, 2 h, 4 h, 8 h, 24 h after caudal vein administration, placing into the heparin-coated EP tubes, taking the upper plasma after centrifuging for 5 min at 8000 rpm/min, and storing at −20° C. until LC-MS/MS analysis;

6) Calculating the pharmacokinetic parameters using WinNonlin software according to the blood concentration—time data obtained from Step 5), shown in Table 4.

TABLE 4

| | Pharmacokinetic parameters | | | | | | |
|---|---|---|---|---|---|---|---|
| | $T_{1/2}$ (h) | $T_{max}$ (h) | $C_{max}$ (ng/ml) | $AUC_{(0-t)}$ (h * ng/ml) | $AUC_{(0-\infty)}$ (h * ng/ml) | $MRT_{(0-\infty)}$ (h) | F (%) |
| Example 27 I.G. 15 mg/kg | 4.10 | 7.33 | 375.77 | 5367.4 | 5224.2 | 7.71 | 32.6 |
| Example 27 I.V. 3 mg/kg | 4.93 | | 1265.10 | 3297.84 | 3380.39 | 4.92 | |

As shown from Table 4, the compounds of the present invention have better pharmacokinetic data, wherein the plasma elimination half-life ($T_{1/2}$) is 4.1 hours, the peak concentration ($C_{max}$) is 375.77 ng/ml, and oral bioavailability (F) is 32.6%. It was reported that when AP24534 (Ponatinib) was orally administered at 15 mg/kg, the peak concentration (Cmax) was 204.8 ng/ml, oral bioavailability (F) is 18.2% (Wei-Sheng Huang et al., Discovery of 3-[2-(Imidazo[1,2-b]pyridazin-3-yl)ethynyl]-4-methyl-N-{4-[(4-methyl-piperazin-1-yl)-methyl]-3-(trifluoromethyl)phenyl}benzamide (AP24534), a Potent, Orally Active Pan-Inhibitor of Breakpoint Cluster Region-Abelson (BCR-ABL) Kinase Including the T315I Gatekeeper Mutant, J. Med. Chem. 2010 (53) 4701-4719). Therefore, the compounds of the present invention have high oral bioavailability and better peak plasma concentration, and have good prospects for clinical application.

Although the present invention has been described in details above, the skilled person in the art would appreciate that various modifications and alterations might be made without departing from the spirit and scope of the present invention. The scope of the invention is not limited to the foregoing detailed description and is defined by the appended claims.

What is claimed is:

1. A compound of general formula I,

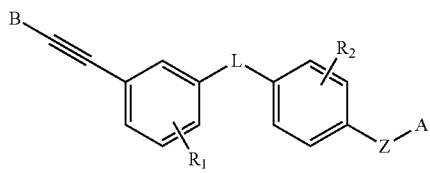

(I)

or a pharmaceutically acceptable salt, isomer, N-oxide, solvate, or crystal thereof,
wherein
L is selected from —C(O)NH—, —NHC(O)NH—, and —NHC(O)—;
Z is selected from $(CH_2)_n$ or O, wherein n is selected from 0, 1, 2, 3, and 4;
A is selected from 5-, 6-, 7- and 8-membered nitrogen-containing heterocyclic groups;
$R_1$ is selected from H, alkyl, alkoxy, halo-substituted alkyl, halo-substituted alkoxy, —OH, —$NH_2$, halogen, and —CN;
$R_2$ is selected from H, alkyl, alkoxy, halo-substituted alkyl, halo-substituted alkoxy, —OH, —$NH_2$, halogen, and —CN; and
B is selected from the following structures:

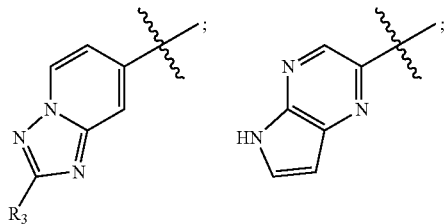

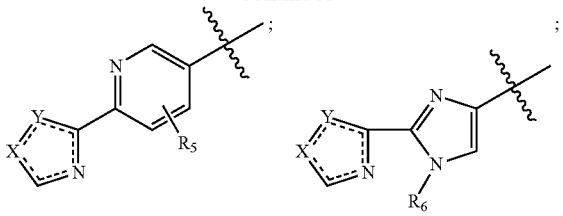

wherein $R_3$ is selected from H, amino, mono-alkylamino, and di-alkylamino;
X is selected from $C(R_4)$ and NH, and Y is selected from N and NH, wherein when X is $C(R_4)$, Y is NH and

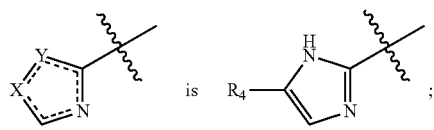

is when X is NH, Y is N and

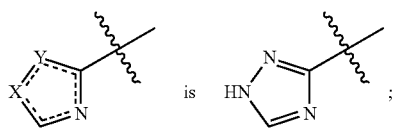

is wherein $R_4$ is selected from H, $NO_2$, halogen, alkyl, halo-substituted alkyl, and —CN;
$R_5$ is selected from H, alkyl, alkoxy, halo-substituted alkyl, halo-substituted alkoxy, —OH, —$NH_2$, halogen, and —CN; and
$R_6$ is selected from H, and alkyl.

2. The compound according to claim 1, or the pharmaceutically acceptable salt, isomer, N-oxide, solvate, or crystal thereof, wherein the compound is the compound of general formula Ia,

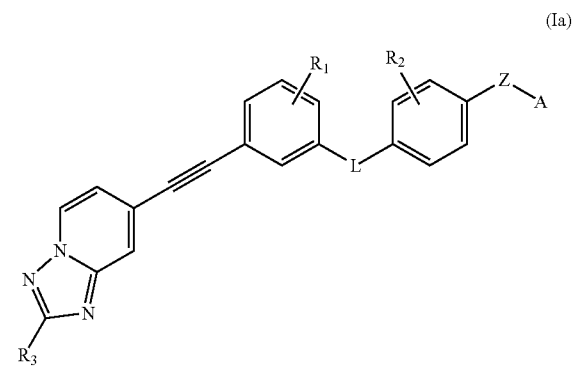

(Ia)

wherein
L is selected from —C(O)NH—, —NHC(O)NH—, and —NHC(O)—;
Z is selected from $(CH_2)_n$ or O, wherein n is selected from 0, 1, 2, 3, and 4;
A is selected from 5-, 6-, 7- and 8-membered nitrogen-containing heterocyclic groups;

R₁ is selected from H, alkyl, alkoxy, halo-substituted alkyl, halo-substituted alkoxy, —OH, —NH₂, halogen, and —CN;

R₂ is selected from H, alkyl, alkoxy, halo-substituted alkyl, halo-substituted alkoxy, —OH, —NH₂, halogen, and —CN; and R₃ is selected from H, amino, mono-alkylamino, and di-alkylamino.

3. The compound according to claim 1, or the pharmaceutically acceptable salt, isomer, N-oxide, solvate, or crystal thereof, wherein the compound is the compound of general formula Ib,

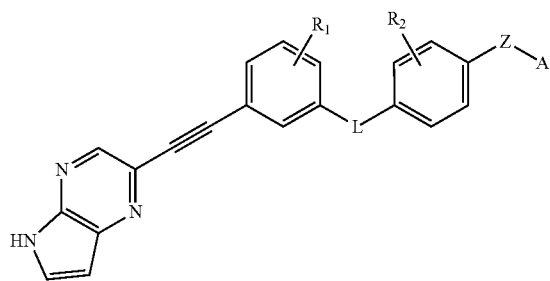

(Ib)

wherein

L is selected from —C(O)NH—, —NHC(O)NH—, and —NHC(O)—;

Z is selected from (CH₂)ₙ or O, wherein n is selected from 0, 1, 2, 3, and 4;

A is selected from 5-, 6-, 7- and 8-membered nitrogen-containing heterocyclic groups;

R₁ is selected from H, alkyl, alkoxy, halo-substituted alkyl, halo-substituted alkoxy, —OH, —NH₂, halogen, and —CN; and R₂ is selected from H, alkyl, alkoxy, halo-substituted alkyl, halo-substituted alkoxy, —OH, —NH₂, halogen, and —CN.

4. The compound according to claim 1, or the pharmaceutically acceptable salt, isomer, N-oxide, solvate, or crystal thereof, wherein the compound is the compound of general formula Id,

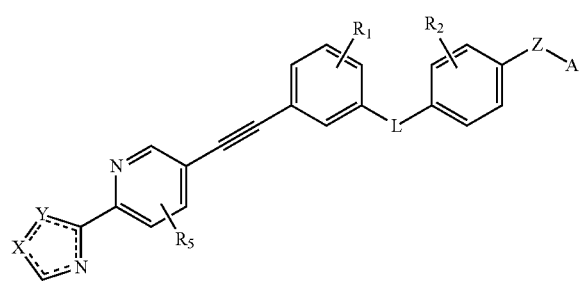

(Id)

wherein

L is selected from —C(O)NH—, —NHC(O)NH—, and —NHC(O)—;

Z is selected from (CH₂)ₙ or O, wherein n is selected from 0, 1, 2, 3, and 4;

A is selected from 5-, 6-, 7- and 8-membered nitrogen-containing heterocyclic groups;

R₁ is selected from H, alkyl, alkoxy, halo-substituted alkyl, halo-substituted alkoxy, —OH, —NH₂, halogen, and —CN;

R₂ is selected from H, alkyl, alkoxy, halo-substituted alkyl, halo-substituted alkoxy, —OH, —NH₂, halogen, and —CN;

X is selected from C(R₄) and NH, and Y is selected from N and NH, wherein when X is C(R₄), Y is NH and

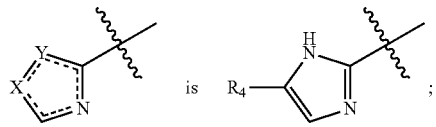

when X is NH, Y is N and

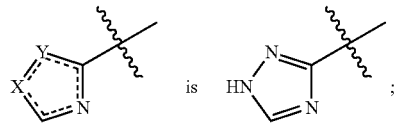

wherein R₄ is selected from H, NO₂, halogen, alkyl, halo-substituted alkyl, and —CN; and R₅ is selected from H, alkyl, alkoxy, halo-substituted alkyl, halo-substituted alkoxy, —OH, —NH₂, halogen, and —CN.

5. The compound according to claim 1, or the pharmaceutically acceptable salt, isomer, N-oxide, solvate, or crystal thereof, wherein the compound is the compound of general formula Ie,

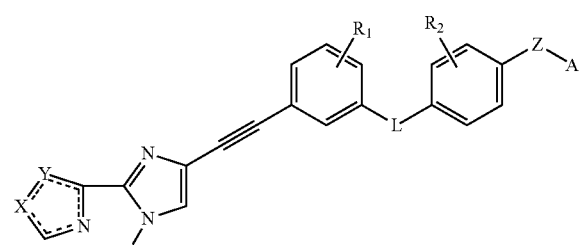

(Ie)

wherein

L is selected from —C(O)NH—, —NHC(O)NH—, and —NHC(O)—;

Z is selected from (CH2)n or O, wherein n is selected from 0, 1, 2, 3, and 4;

A is selected from 5-, 6-, 7- and 8-membered nitrogen-containing heterocyclic groups;

R1 is selected from H, alkyl, alkoxy, halo-substituted alkyl, halo-substituted alkoxy, —OH, —NH2, halogen, and —CN;

R2 is selected from H, alkyl, alkoxy, halo-substituted alkyl, halo-substituted alkoxy, —OH, —NH2, halogen, and —CN;

X is selected from C(R₄) and NH, and Y is selected from N and NH; wherein when X is C(R₄), Y is NH and

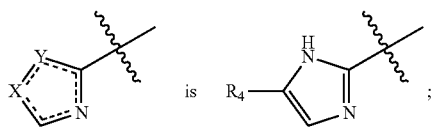 is 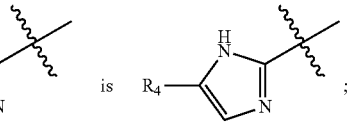;

when X is NH, Y is N and

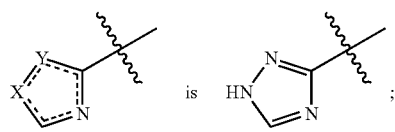 is 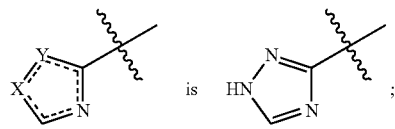;

wherein R$_4$ is selected from H, NO$_2$, halogen, alkyl, halo-substituted alkyl, and —CN; and R6 is selected from H, and alkyl.

6. The compound according to claim 1, or the pharmaceutically acceptable salt, isomer, N-oxide, solvate, or crystal thereof, wherein R$_1$ is selected from H, C$_{1-6}$ alkyl, C$_{1-6}$ alkoxy, halo-substituted C$_{1-6}$ alkyl, halo-substituted C$_{1-6}$ alkoxy, —OH, —NH$_2$, halogen, and —CN;

R$_2$ is selected from H, C$_{1-6}$ alkyl, C$_{1-6}$ alkoxy, halo-substituted C$_{1-6}$ alkyl, halo-substituted C$_{1-6}$ alkoxy, —OH, —NH$_2$, halogen, and —CN; and A is selected from 5-, and 6-membered nitrogen-containing heterocyclic groups.

7. The compound according to claim 2, or the pharmaceutically acceptable salt, isomer, N-oxide, solvate, or crystal thereof, wherein R$_3$ is selected from H, C$_{1-6}$ alkylamino, mono-alkylamino, and di C$_{1-6}$ alkylamino.

8. The compound according to claim 5, or the pharmaceutically acceptable salt, isomer, N-oxide, solvate, or crystal thereof, wherein X is selected from C(R$_4$) and NH, and Y is selected from N and NH, wherein when X is C(R$_4$), Y is NH and

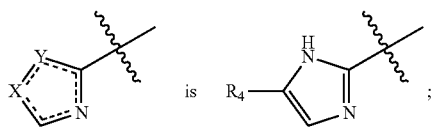 is 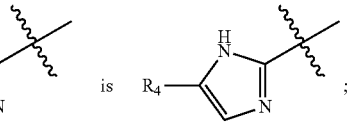;

when X is NH, Y is N and

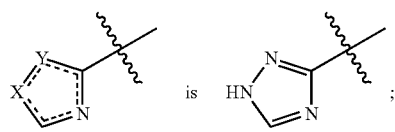 is 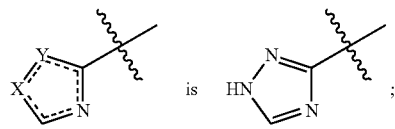;

wherein R$_4$ is selected from H, NO$_2$, halogen, C$_{1-6}$ alkyl, halo-substituted C$_{1-6}$ alkyl, —CN.

9. The compound according to claim 1, or the pharmaceutically acceptable salt, isomer, N-oxide, solvate, or crystal thereof, wherein the compound is selected from the group consisting of the following compounds:

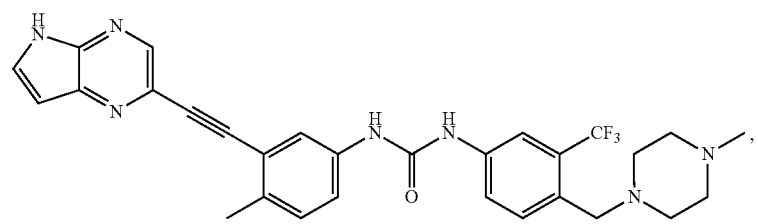

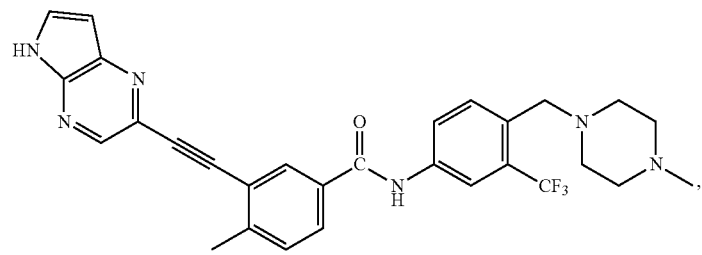

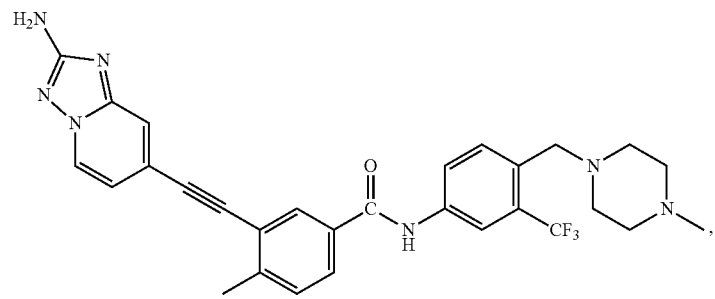

-continued
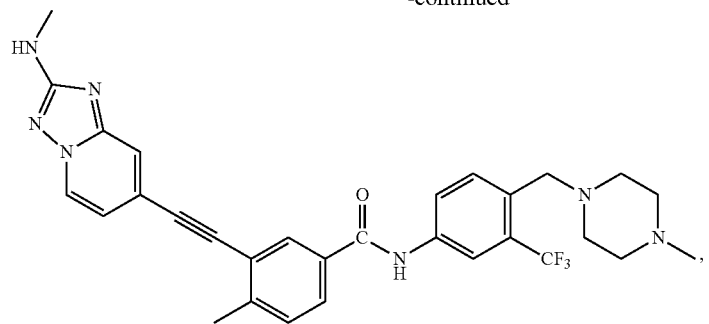
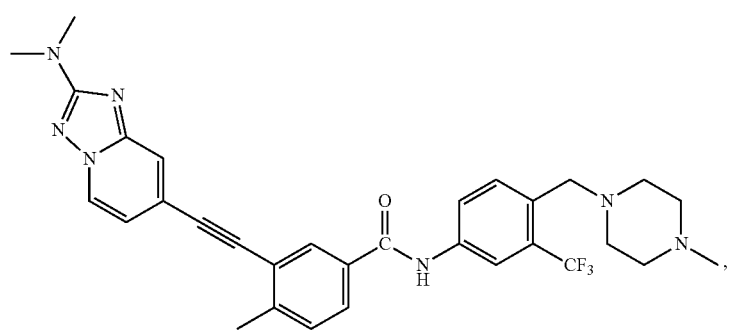
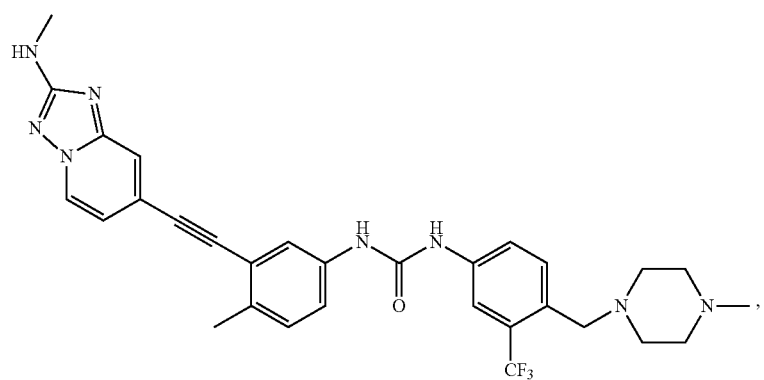
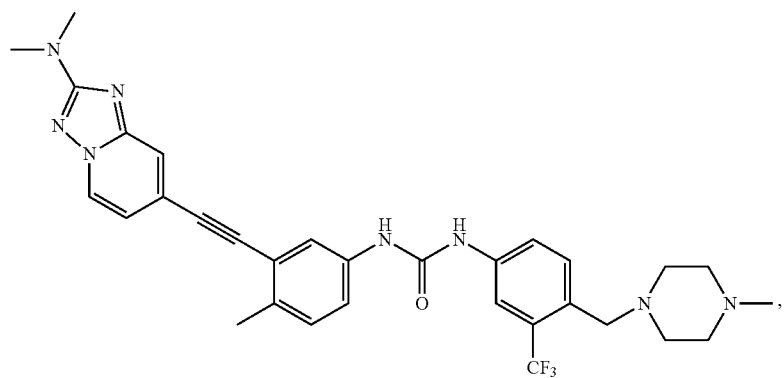
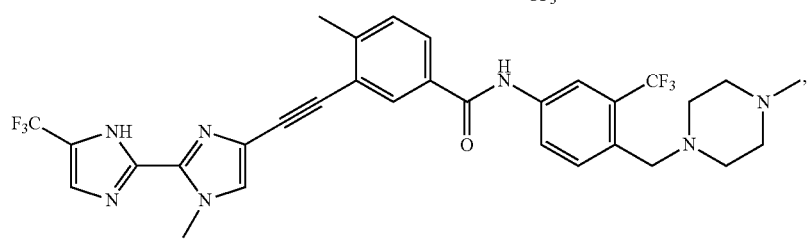

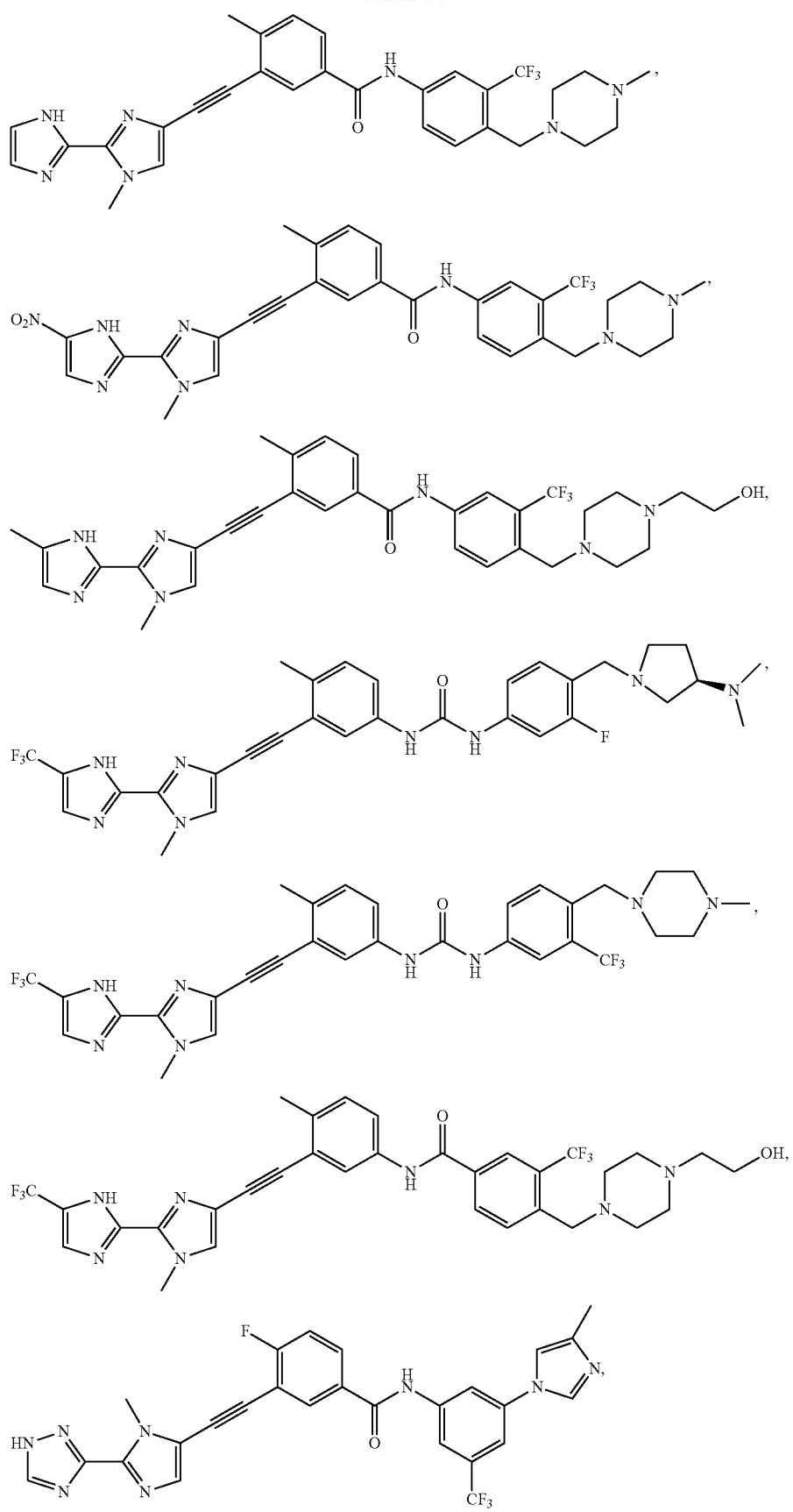

-continued
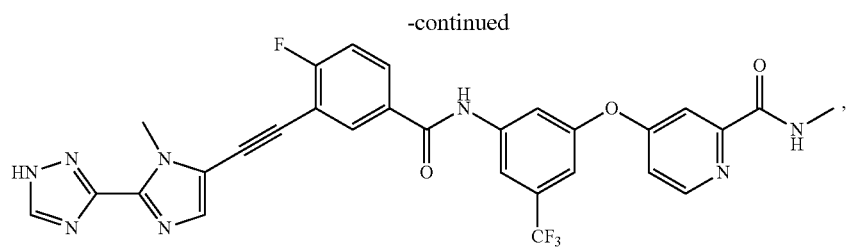
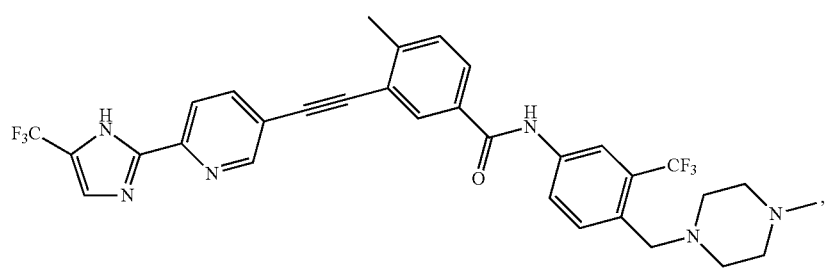
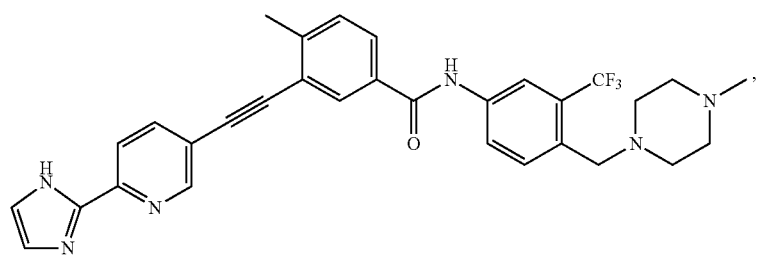
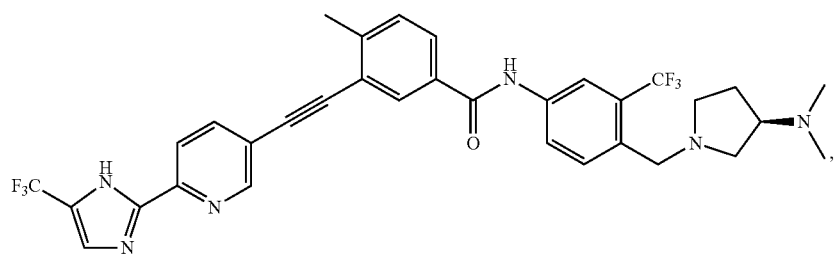
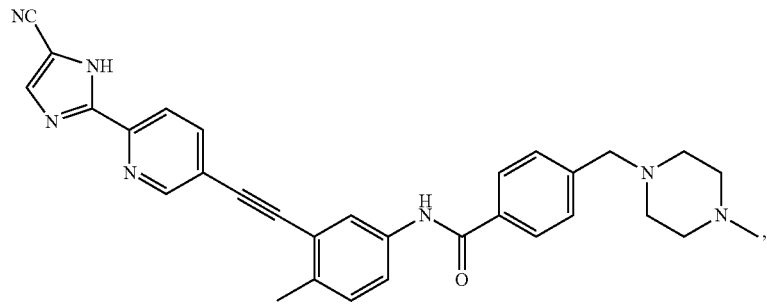
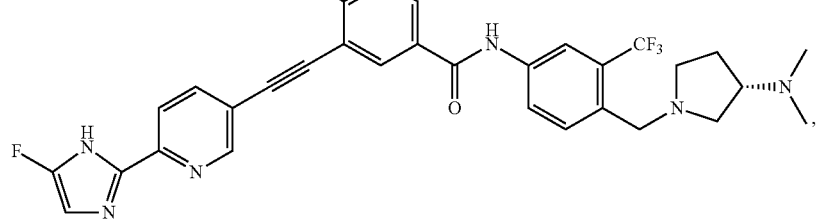

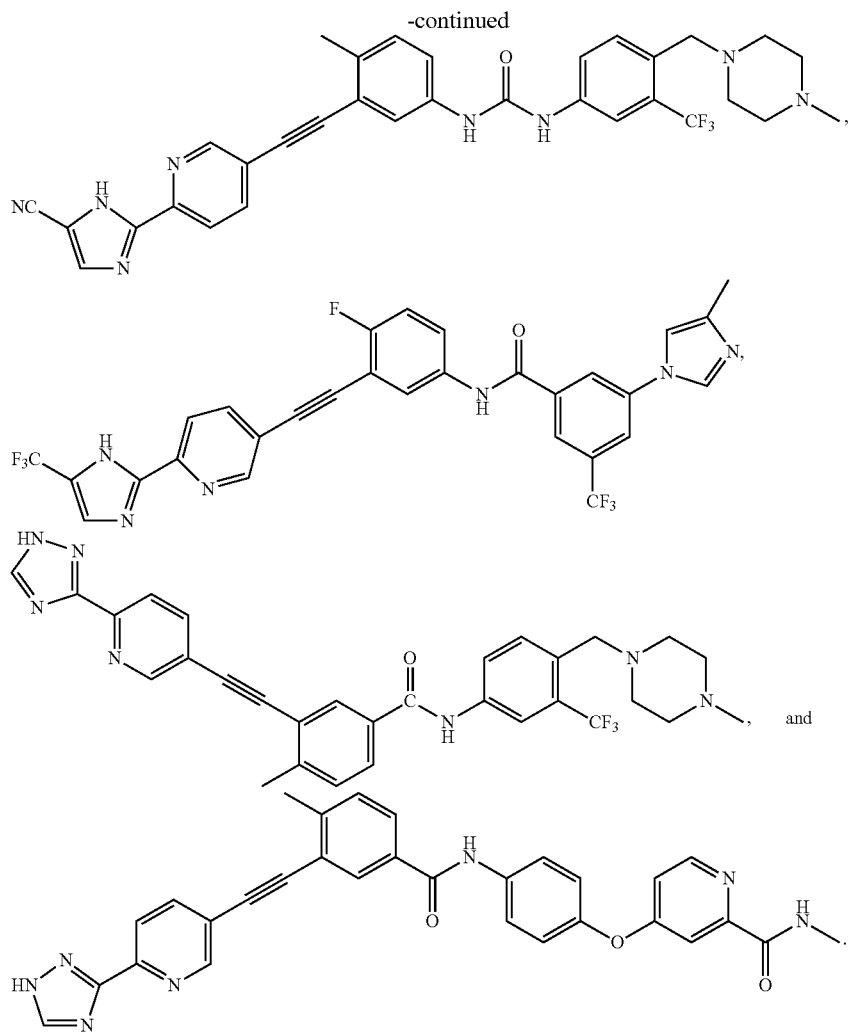

10. A pharmaceutical composition comprising the compound according to claim 1, or the pharmaceutically acceptable salt, isomer, N-oxide, solvate, or crystal thereof, and a pharmaceutically acceptable carrier.

11. A method of treating a tumor, comprising administering to a patient in need thereof a therapeutically effective amount of the compound according to claim 1, or the pharmaceutically acceptable salt, isomer, N-oxide, solvate, or crystal thereof.

12. The compound according to claim 2, wherein A is selected from piperazinyl, tetrahydropyrrolyl, or substituted piperazinyl and tetrahydropyrrolyl, wherein the substituent(s) is(are) selected from alkyl, hydroxy, hydroxyalkyl, alkoxy, amino, mono-alkylamino, di-alkylamino, aminoacyl, alkylaminoacyl, arylaminoacyl, heteroarylaminoacyl, halogen, halo-substituted alkyl, and halo-substituted alkoxy.

13. The compound according to claim 3, wherein A is selected from piperazinyl, tetrahydropyrrolyl, or substituted piperazinyl and tetrahydropyrrolyl, wherein the substituent(s) is(are) selected from alkyl, hydroxy, hydroxyalkyl, alkoxy, amino, mono-alkylamino, di-alkylamino, aminoacyl, alkylaminoacyl, arylaminoacyl, heteroarylaminoacyl, halogen, halo-substituted alkyl, and halo-substituted alkoxy.

14. The compound according to claim 4, wherein A is selected from piperazinyl, tetrahydropyrrolyl, or substituted piperazinyl and tetrahydropyrrolyl, wherein the substituent(s) is(are) selected from alkyl, hydroxy, hydroxyalkyl, alkoxy, amino, mono-alkylamino, di-alkylamino, aminoacyl, alkylaminoacyl, arylaminoacyl, heteroarylaminoacyl, halogen, halo-substituted alkyl, and halo-substituted alkoxy.

15. The compound according to claim 5, wherein A is selected from piperazinyl, tetrahydropyrrolyl, or substituted piperazinyl and tetrahydropyrrolyl, wherein the substituent(s) is(are) selected from alkyl, hydroxy, hydroxyalkyl, alkoxy, amino, mono-alkylamino, di-alkylamino, aminoacyl, alkylaminoacyl, arylaminoacyl, heteroarylaminoacyl, halogen, halo-substituted alkyl, and halo-substituted alkoxy.

16. A pharmaceutical composition comprising the compound according to claim 9, or the pharmaceutically acceptable salt, isomer, N-oxide, solvate, or crystal thereof, and a pharmaceutically acceptable carrier.

17. A method of treating a tumor, comprising administering to a patient in need thereof a therapeutically effective amount of the compound according to claim 9, or the pharmaceutically acceptable salt, isomer, N-oxide, solvate, or crystal thereof.

18. A method of treating a tumor, comprising administering to a patient in need thereof a therapeutically effective amount of the pharmaceutical composition according to claim 10.

* * * * *